US012729217B2

(12) United States Patent
Richard et al.

(10) Patent No.: US 12,729,217 B2
(45) Date of Patent: Sep. 8, 2026

(54) METHOD OF SYNTHESIZING SINGLE-STRANDED NUCLEOTIDE SEQUENCE, BLOCKED NUCLEOSIDE TRIPHOSPHATES AND RELATED METHODS

(71) Applicant: Agency for Science, Technology and Research, Singapore (SG)

(72) Inventors: Jean-Alexandre Richard, Singapore (SG); Xi Lin, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 996 days.

(21) Appl. No.: 17/427,479

(22) PCT Filed: Jan. 31, 2020

(86) PCT No.: PCT/SG2020/050048

§ 371 (c)(1),
(2) Date: Jul. 30, 2021

(87) PCT Pub. No.: WO2020/159447

PCT Pub. Date: Aug. 6, 2020

(65) Prior Publication Data

US 2023/0148152 A1 May 11, 2023

(30) Foreign Application Priority Data

Jan. 31, 2019 (SG) ............................ 10201900936P

(51) Int. Cl.
*C07H 1/00* (2006.01)
*C07H 19/10* (2006.01)
*C07H 21/00* (2006.01)

(52) U.S. Cl.
CPC ............... *C07H 1/00* (2013.01); *C07H 19/10* (2013.01); *C07H 21/00* (2013.01)

(58) Field of Classification Search
CPC .......... C07H 1/00; C07H 19/06; C07H 19/10; C07H 19/16; C07H 19/20; C07H 21/00; C12Q 2525/186; C12Q 1/6806
See application file for complete search history.

(56) References Cited

U.S. PATENT DOCUMENTS

| | | | | |
|---|---|---|---|---|
| 5,808,045 | A | 9/1998 | Hiatt et al. | |
| 5,872,244 | A | 2/1999 | Hiatt et al. | |
| 2011/0014611 | A1 | 1/2011 | Ju et al. | |
| 2020/0216891 | A1* | 7/2020 | Francais ................ | C07H 19/06 |

FOREIGN PATENT DOCUMENTS

| | | | |
|---|---|---|---|
| WO | 2008042067 | A2 | 4/2008 |
| WO | 2016128731 | A1 | 8/2016 |
| WO | 2017185026 | A1 | 10/2017 |
| WO | 2018102554 | A1 | 6/2018 |
| WO | 2019051250 | A1 | 3/2019 |

OTHER PUBLICATIONS

Metzker et al., Published Oct. 11, 1994, Nucleic Acid Research, vol. 22, pp. 4259-4267 (Year: 1994).*

Mathews et al., Published Aug. 9, 2016, Organic & Bimolecular Chemistry, vol. 14, pp. 8278-8288 (Year: 2016).*

Stutz et al., Published Sep. 25, 2000, Helvetica, vol. 83, Issue 9, pp. 2477-2503 (Year: 2000).*

Lin et al., Published Jul. 22, 2016, Organic Letters, vol. 18, Issue 15, pp. 3870-3873 (Year: 2016).*

Notification of Transmittal of International Search Report and the Written Opinion for International Application No. PCT/SG2020/050048 "Method of Synthesizing Single-Stranded Nucleotide Sequence, Blocked Nucleoside Triphosphates and Related Methods" dated Jun. 26, 2020.

Jensen M.A., et al, "Template-Independent Enzymatic Oligonucleotide Synthesis (TiEOS): Its History, Prospects, and Challenges", Biochemistry. Mar. 27, 2018; 57(12): 1821-1832.

Foldesi A., et al., The fluoride cleavable 2-(cyanoethoxy)methyl (CEM) group as reversible 3'-O-terminator for DNA sequencing-by-synthesis—synthesis, incorporation, and cleavage. Nucleosides Nucleotides & Nucleic Acids, Apr. 4, 2007, vol. 26, No. 3, pp. 271-275.

Knapp D. C. , et al. , Fluoride-Cleavable, Fluorescently Labelled Reversible Terminators: Synthesis and Use in Primer Extension. Chemistry—A European Journal, Feb. 3, 2011 , vol. 17, No. 10, pp. 2903-2915.

Ruparel H., et al. , Design and Synthesis of a 3'-O-allyl Photocleavable Fluorescent Nucleotide as a Reversible Terminator for DNA Sequencing by Synthesis. PNAS, Apr. 13, 2005, vol. 102, No. 17, pp. 5932-5937.

Search Report for Application No. SG 11202107271T "Method of Synthesizing Single-Stranded Nucleotide Sequence, Blocked Nucleoside Triphosphates and Related Methods" date of completion: May 23, 2022.

* cited by examiner

*Primary Examiner* — Renee Claytor
*Assistant Examiner* — Jaret J Crews
(74) *Attorney, Agent, or Firm* — Hamilton, Brook, Smith & Reynolds, P.C.

(57) ABSTRACT

There is provided a method of synthesizing a single-stranded nucleotide sequence, the method comprising adding a blocked nucleoside triphosphate to an initiator nucleotide sequence to incorporate a corresponding blocked nucleotide thereto in the presence of a polymerase, wherein the blocked nucleoside triphosphate has one of the general formulae (I), (II), (III), (IV), (V) and (VI).

18 Claims, 21 Drawing Sheets

Specification includes a Sequence Listing.

Post stained with SYBR Gold

FAM only, 20% PAGE, 150 V, 80 min

Post stained with SYBR Gold

15% Urea PAGE
150V, 7A, 53 minutes (blue dye reaching edge)

Post stained with SYBR Gold

15% Urea PAGE
150V, 7A, 53 minutes (blue dye reaching edge)

Post stained with SYBR Gold

Post stained with SYBR Gold

Rxn 1 -- 5'-FAM-20mer + 100% dATP
Rxn 2 -- 5'-FAM-20mer + 25% dATP+ 75% triphosphate
Rxn 3 -- 5'-FAM-20mer + 2.5% dATP+ 97.5% triphosphate
Rxn 4 -- 5'-FAM-20mer + 0.25% dATP+ 99.75% triphosphate
Rxn 5 -- 5'-FAM-20mer + 100% triphosphate
Rxn 6 -- 5'-FAM-20mer + 100% triphosphate (no TdT)
Rxn 7 -- 10bp DNA ladder

METHOD OF SYNTHESIZING SINGLE-STRANDED NUCLEOTIDE SEQUENCE, BLOCKED NUCLEOSIDE TRIPHOSPHATES AND RELATED METHODS

RELATED APPLICATIONS

This application is the U.S. National Stage of International Application No. PCT/SG2020/050048, filed Jan. 31, 2020, which designates the U.S., published in English, and claims priority under 35 U.S.C. § 119 or 365(c) to SG Application No. 10201900936P, filed Jan. 31, 2019. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

a) File name: 59751000001_SequenceListing.txt; created Mar. 11, 2022, 707 Bytes in size.

TECHNICAL FIELD

The present disclosure relates broadly to a method of synthesizing a single-stranded nucleotide sequence. The present disclosure also relates to blocked nucleoside triphosphates for said method and a method of preparing said blocked nucleoside triphosphates.

BACKGROUND

Nucleic acids are expected to become the molecule of the $21^{st}$ century because of the wide range of applications for oligonucleotide therapeutics, deoxyribonucleic acid (DNA) materials, synthetic biology tools and data storage.

In the last 30 years, the supply of nucleic acids has been secured by automated chemical synthesis using phosphoramidite chemistry. However, the nature of the chemistry currently provides reliable access to oligonucleotides up to only 60-100 bases. Furthermore, reactions based on such chemistry also generate a huge amount of chemical waste. Therefore, in order to improve the process of synthesizing nucleic acids, it is important to devise new synthetic technologies that can allow access to oligonucleotides and genes in a more sustainable and cost-effective way.

Many investigations on nucleic acids synthesis have been conducted, one of which is the enzymatic synthesis of oligonucleotides biocatalyzed by template-independent terminal deoxynucleotidyl transferase (TdT). Such a method requires design strategies ensuring that only one base at the time is introduced on the elongating nucleic acid chain. Although it was found that the modification of the base (Scheme 1) may ensure that this requirement is met, the approach is hardly scalable because of the difficult synthetic access of the reversible terminators.

Scheme 1. Nucleotide reversible terminators modified on nucleobase

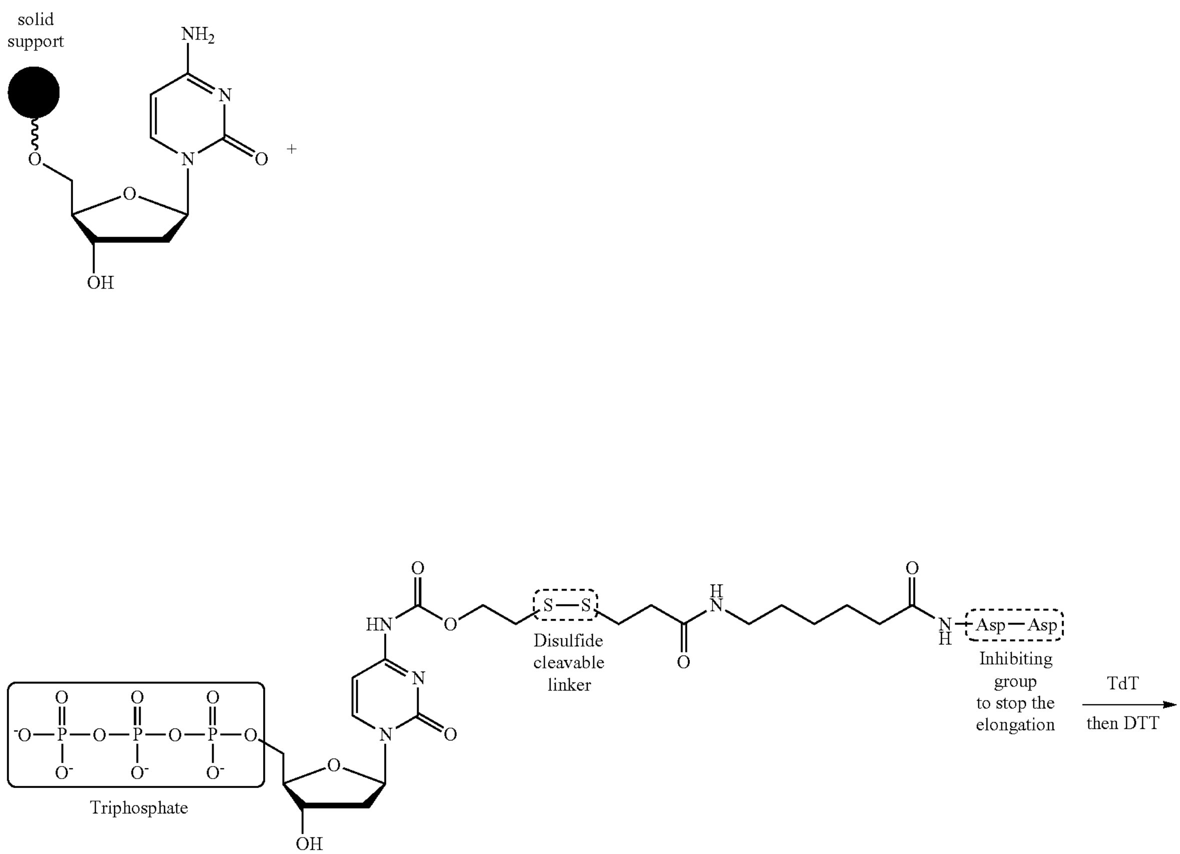

-continued

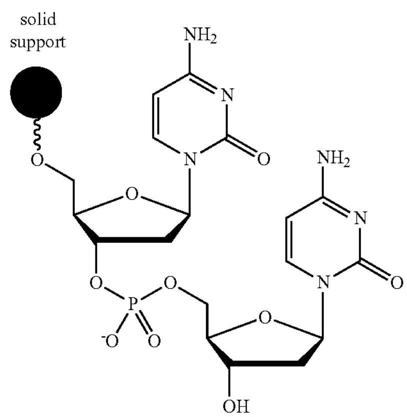

Another approach to nucleic acid synthesis which avoids the use of complex reversible terminators is the blocking of the 3'-position by a removable protecting group. This approach was widely used in the context of DNA sequencing (e.g., Illumina sequencing-by-synthesis technology) and was similarly developed for the template-independent synthesis of oligonucleotides. In this approach, reversible terminators blocked at the 3'-position by protecting groups such as 3'-$ONH_2$, 3'-O-azidomethylene, 3'-acetate and 2-nitrobenzyl groups have been explored (Scheme 2).

However, there are several drawbacks of working with such protecting groups. Firstly, they can have stability issues (for e.g. especially acetate), therefore making it difficult to achieve reliable DNA synthesis results. Secondly, deprotection of these groups are generally difficult and can require the use of harsh reaction conditions (Scheme 2). For instance, deprotection of the —$ONH_2$ group protecting group) requires a strong oxidizing agent such as sodium nitrite which can potentially damage the DNA strand. Other problems arising from the use of these groups include the formation of undesired side products due to incomplete deprotection/unblocking under reductive or photochemical conditions, like during the deprotection of azidomethyl and 2-nitrobenzyl groups, respectively.

Scheme 2. Drawbacks of working with nucleotide reversible terminators in the art

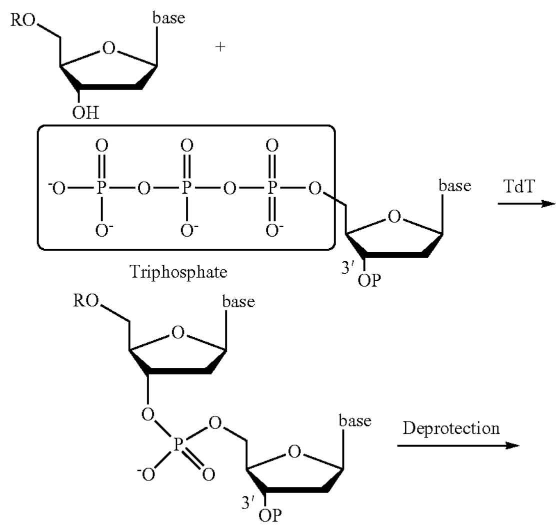

-continued

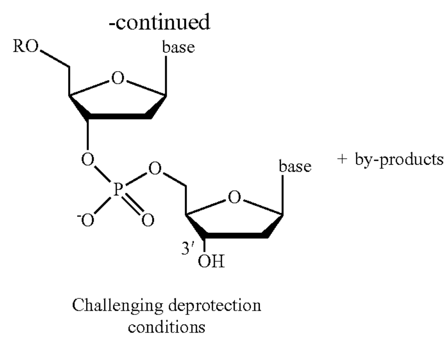

Challenging deprotection conditions

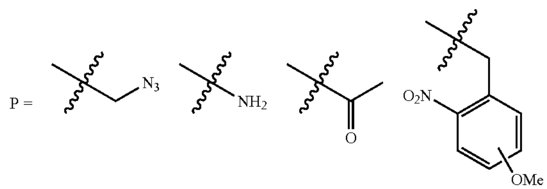

In view of the above, there is a need to address or at least ameliorate the above-mentioned problems. In particular, there is a need to provide a method for synthesizing single stranded nucleotide sequence and blocked nucleoside triphosphates that address or at least ameliorate the above-mentioned problems.

SUMMARY

In one aspect, there is provided a method of synthesizing a single-stranded nucleotide sequence, the method comprising:

(i) adding a blocked nucleoside triphosphate to an initiator nucleotide sequence to incorporate a corresponding blocked nucleotide thereto in the presence of a polymerase, wherein the blocked nucleoside triphosphate has one of the general formulae (I), (II), (III), (IV), (V) and (VI):

(I)

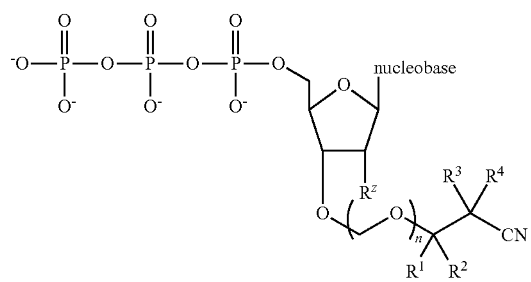

(II)

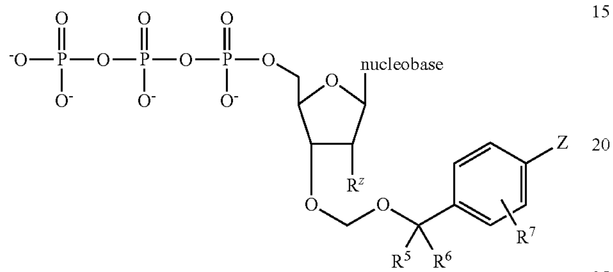

(III)

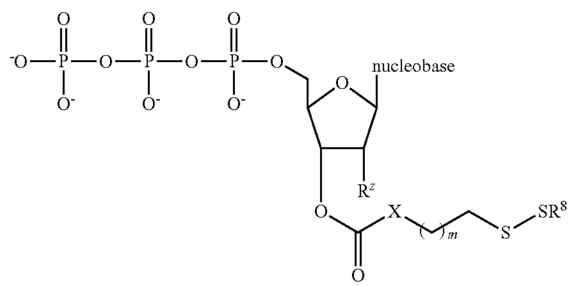

(IV)

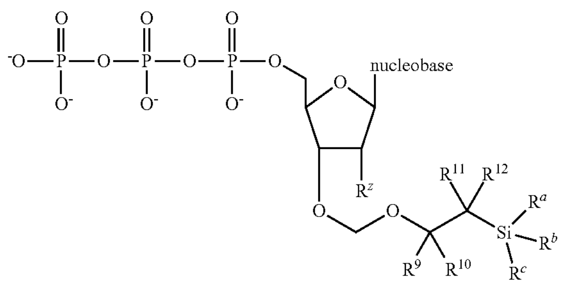

(V)

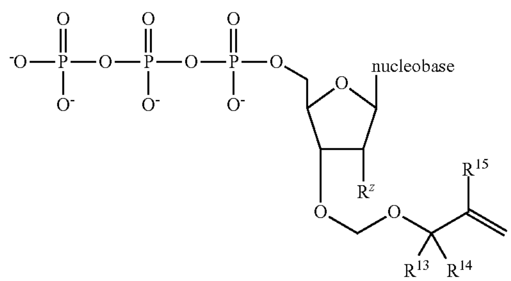

-continued (VI)

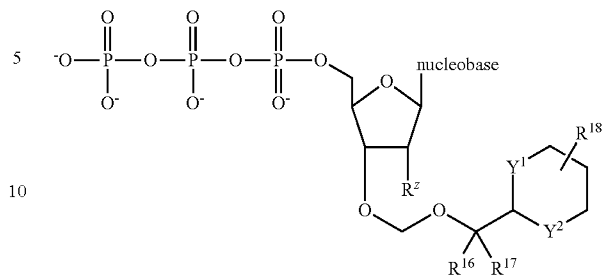

wherein n=0 or 1;

m=0 to 20;

$R^z$ is H or OH;

$R^1$, $R^2$, $R^3$, $R^4$, $R^5$, $R^6$, $R^a$, $R^b$ and $R^c$ are each independently selected from hydrogen, alkyl, alkenyl, aryl and heteroaryl;

$R^7$ is selected from hydrogen, alkyl, halogen, —$OR^{19}$, —$NR^{20}R^{21}$ and —$SR^{22}$, wherein $R^{19}$, $R^{20}$, $R^{21}$ and $R^{22}$ are independently selected from hydrogen, alkyl, alkenyl, aryl and heteroaryl;

$R^8$, $R^9$, $R^{10}$, $R^{11}$, $R^{12}$, $R^{13}$, $R^{14}$, $R^{15}$, $R^{16}$, $R^{17}$ and $R^{18}$ are independently selected from hydrogen, alkyl, alkenyl, aryl and heteroaryl;

X is a heteroatom selected from O, S and NH;

$Y^1$ and $Y^2$ are independently selected from S and Se; and

Z is a chemical moiety that is capable of being released under suitable conditions to trigger removal of the adjacent benzyl linker.

In one embodiment, Z is $NO_2$.

In one embodiment, $R^a$, $R^b$ and $R^c$ are each methyl.

In one embodiment, the method further comprises (ii) removing a removable terminating group from the incorporated blocked nucleotide to obtain a corresponding nucleotide that is unblocked at the 3'-O position.

In one embodiment, the method further comprises (iii) adding a blocked nucleoside triphosphate of any one of the general formulae (I), (II), (III), (IV), (V) and (VI) to the 3'-O position of the unblocked nucleotide obtained in step (ii) in the presence of a polymerase; and (iv) optionally repeating step (ii) and/or (iii) one or more times until a single-stranded nucleotide sequence of a desired length is obtained.

In one embodiment, the polymerase is a template independent polymerase.

In one embodiment, the polymerase comprises terminal deoxynucleotidyl transferase (TdT) and/or polymerase theta (POLQ).

In one embodiment, the step (ii) of removing the removable terminating group is adapted to be carried out in aqueous conditions.

In one embodiment, each step of the method is adapted to be carried out in aqueous conditions.

In one embodiment, the nucleobase is selected from the group consisting of adenine (A), cytosine (C), guanine (G), thymine (T), uracil (U), uric acid, isocytosine, isoguanine, 2-aminopurine, 2,6-diaminopurine, 5-fluorouracil, 5-bromouracil, 5-chlorouracil, 5-iodouracil, hypoxanthine, xanthine, acetylcytosine, 5-(carboxyhydroxylmethyl)uracil, 5-carboxymethylaminomethyl-2-thiouridine, 5-carboxymethylaminonethyluracil, dihydrouracil, beta-D-galactosylqueosine, inosine, N-6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5-methoxycarboxymethyluracil, 5-methoxyuracil, 2-methylthio-N-6-isopentenyladenine, uracil-5-oxy acetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil and 3-(3-amino-3-N-2-carboxypropyl) uracil.

In one embodiment, the method is substantially devoid of the formation of side products that are reactive to the nucleobases of the nucleotide sequence.

In one embodiment, the single-stranded nucleotide sequence comprises a single-stranded deoxynucleotide sequence.

In one embodiment, the initiator nucleotide sequence comprises a single-stranded deoxynucleotide sequence or part thereof.

In one embodiment, the blocked nucleoside triphosphate comprises a deoxyribonucleoside triphosphate.

In one embodiment, the blocked nucleoside triphosphate comprises a deoxyribonucleoside triphosphate selected from the group consisting of deoxyadenosine triphosphate, deoxycytidine triphosphate, deoxyguanosine triphosphate and deoxythymidine triphosphate.

In one embodiment, the blocked nucleoside triphosphate is selected from the following:

(1A)

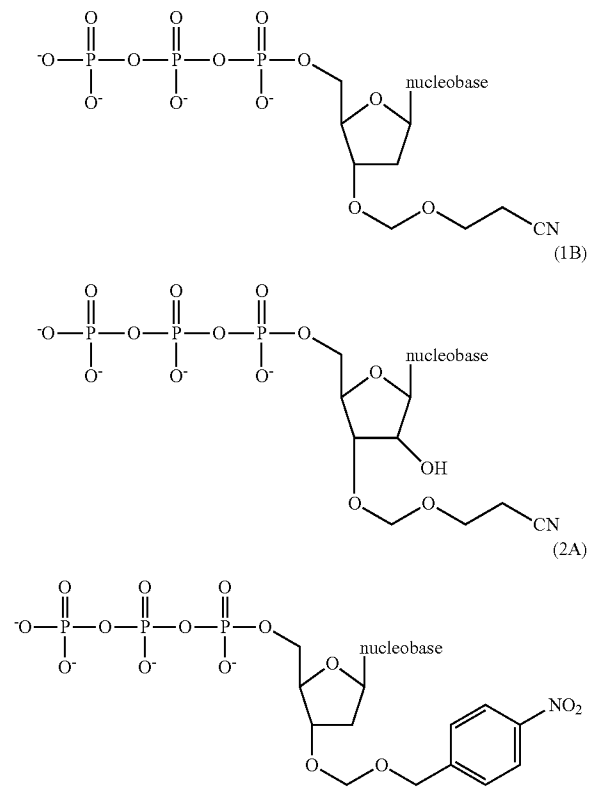

(1B)

(2A)

-continued (2B)

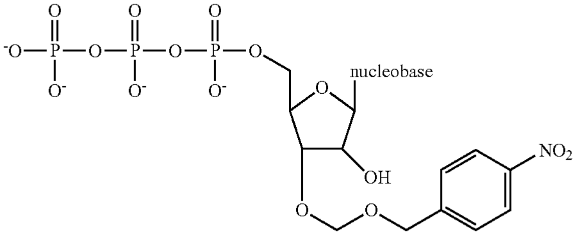

(3A)

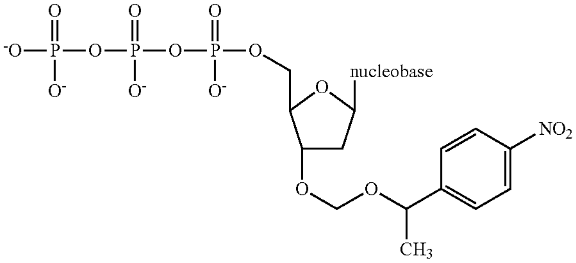

(3B)

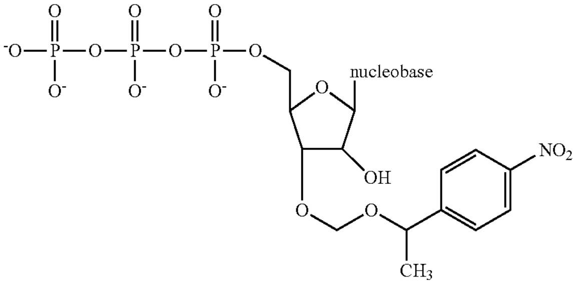

(4A)

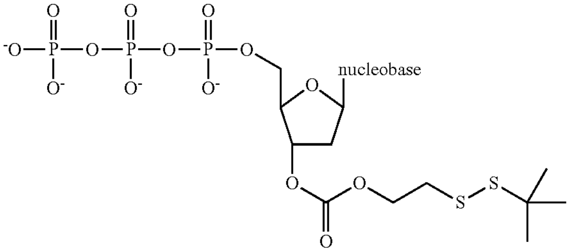

(4B)

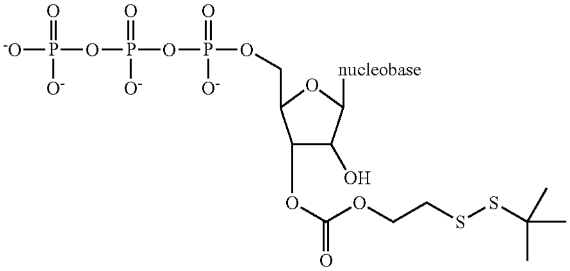

-continued (5A)

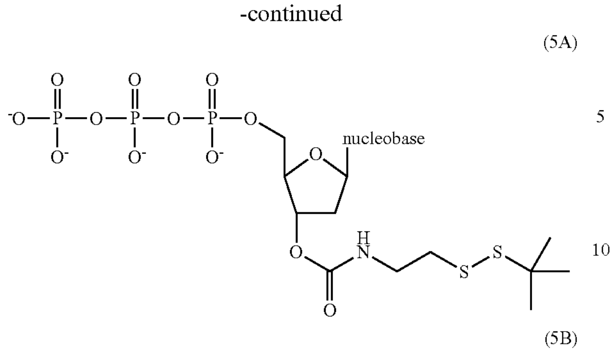

(5B)

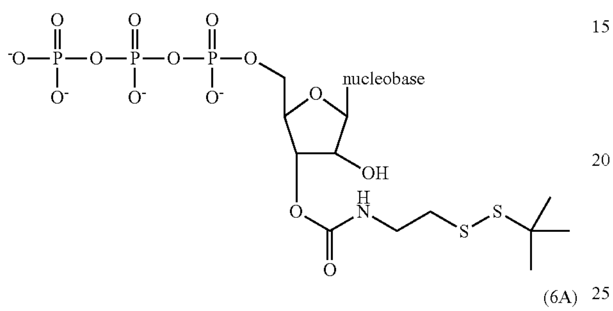

(6A)

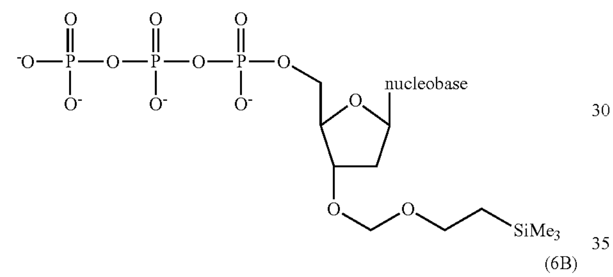

(6B)

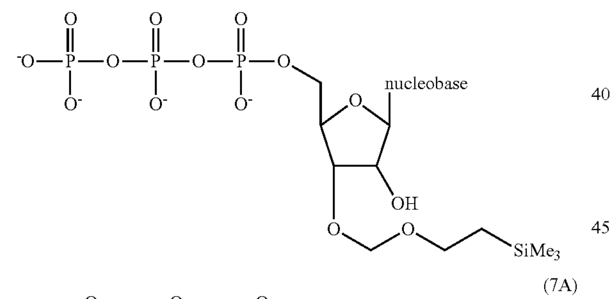

(7A)

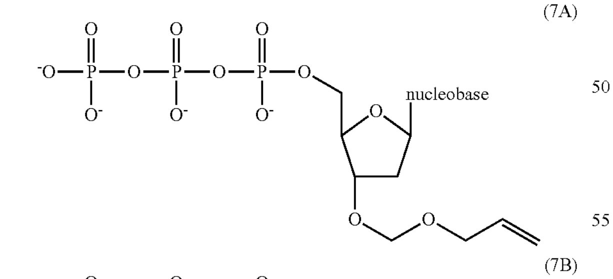

(7B)

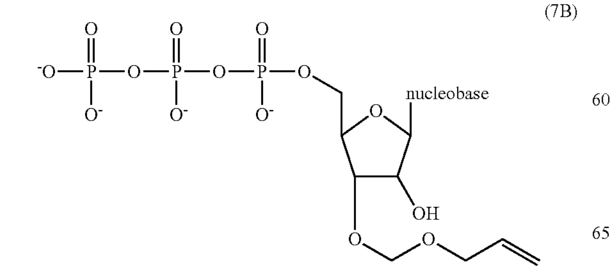

-continued (8A)

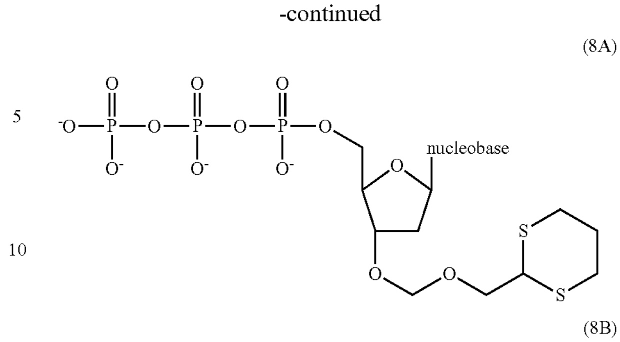

(8B)

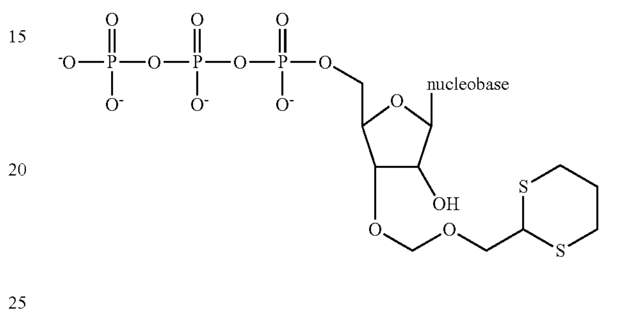

(9A)

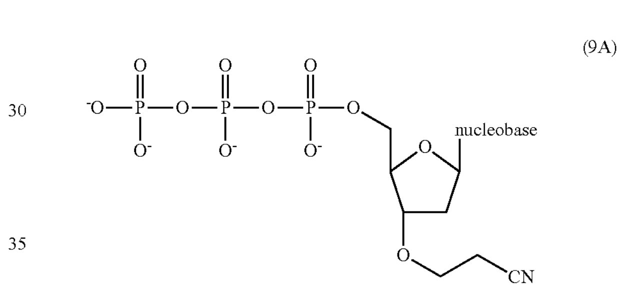

(9B)

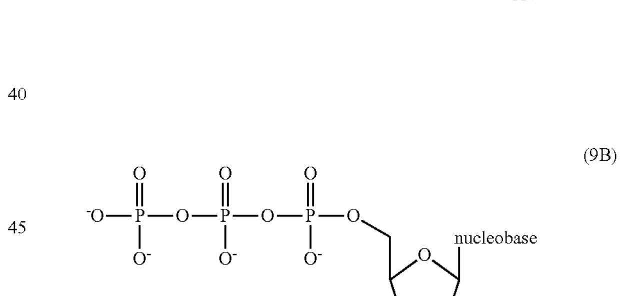

, wherein nucleobase is selected from the group consisting of adenine (A), cytosine (C), guanine (G), uracil (U) and thymine (T).

In one embodiment, step (i) and/or (iii) comprises forming a phosphodiester linkage between the initiator nucleotide sequence and the blocked nucleoside triphosphate.

In one embodiment, step (i) and/or (iii) comprises release of a pyrophosphate.

In one aspect, there is provided a blocked nucleoside triphosphate for the method as disclosed herein, the blocked nucleoside triphosphate having any one of the general formulae (I), (II), (III), (IV), (V) and (VI):

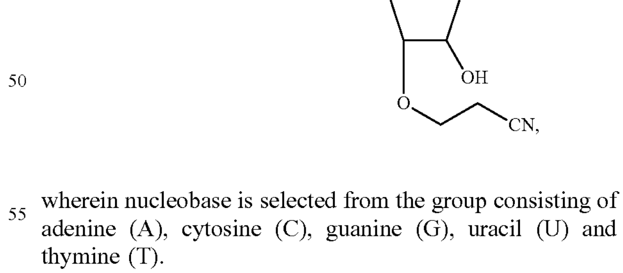

(I)

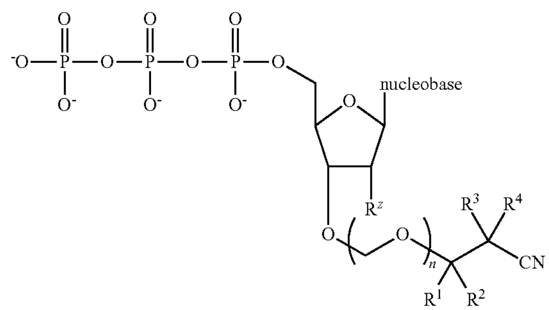

(II)

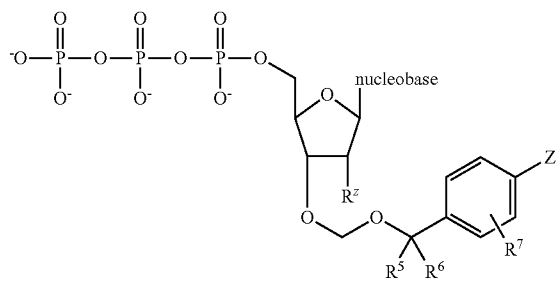

(III)

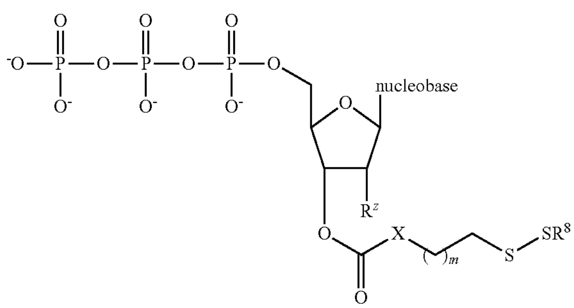

(IV)

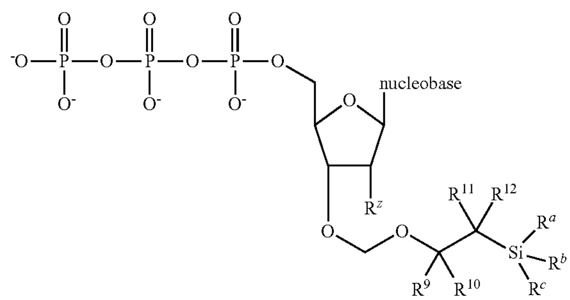

(V)

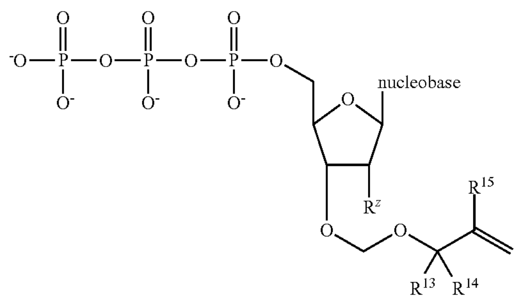

-continued (VI)

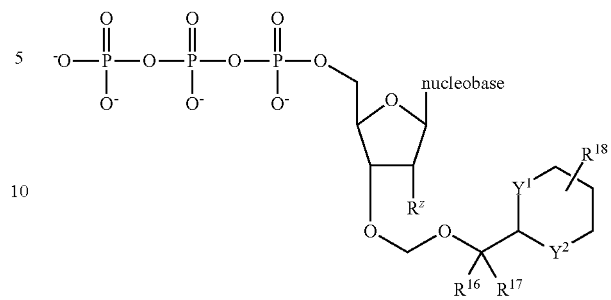

wherein n=0 or 1;

m=0 to 20;

$R^z$ is H or OH;

$R^1$, $R^2$, $R^3$, $R^4$, $R^5$, $R^6$, $R^a$, $R^b$ and $R^c$ are each independently selected from hydrogen, alkyl, alkenyl, aryl and heteroaryl;

$R^7$ is selected from hydrogen, alkyl, halogen, —$OR^{19}$, —$NR^{20}R^{21}$ and —$SR^{22}$, wherein $R^{19}$, $R^{20}$, $R^{21}$ and $R^{22}$ are independently selected from hydrogen, alkyl, alkenyl, aryl and heteroaryl;

$R^8$, $R^9$, $R^{10}$, $R^{11}$, $R^{12}$, $R^{13}$, $R^{14}$, $R^{15}$, $R^{16}$, $R^{17}$ and $R^{18}$ are independently selected from hydrogen, alkyl, alkenyl, aryl and heteroaryl;

X is a heteroatom selected from O, S and NH;

$Y^1$ and $Y^2$ are independently selected from S and Se;

Z is a chemical moiety that is capable of being released under suitable conditions to trigger removal of the adjacent benzyl linker; and with the proviso that when n=0, $R^1$ and $R^2$ are both not hydrogen.

In one embodiment, Z is $NO_2$.

In one embodiment, $R^a$, $R^b$ and $R^c$ are each methyl.

In one embodiment, the blocked nucleoside triphosphate is selected from the following:

(1A)

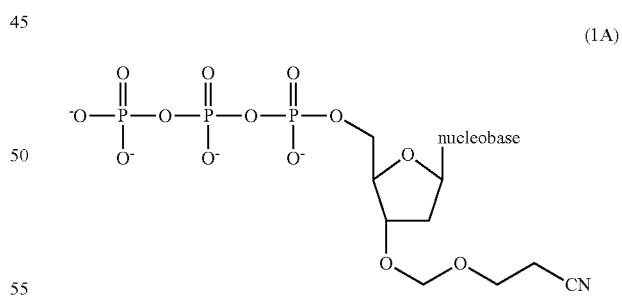

(1B)

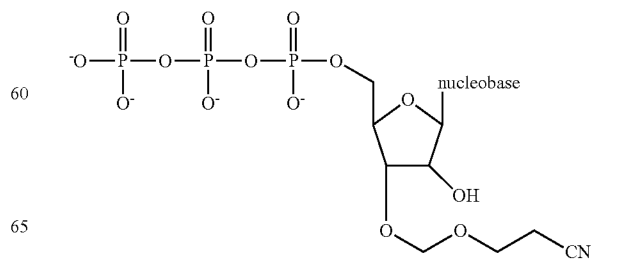

-continued
(2A)
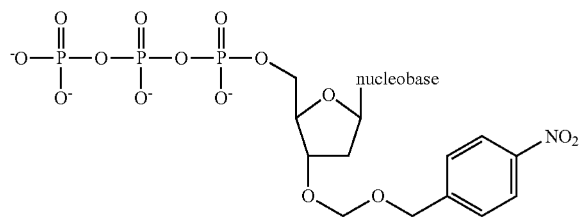
(2B)
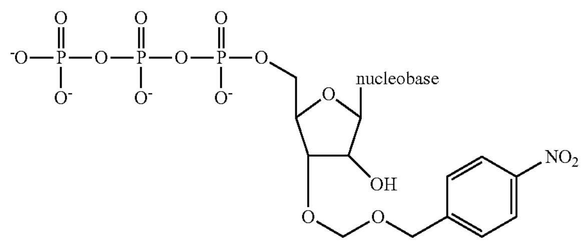
(3A)
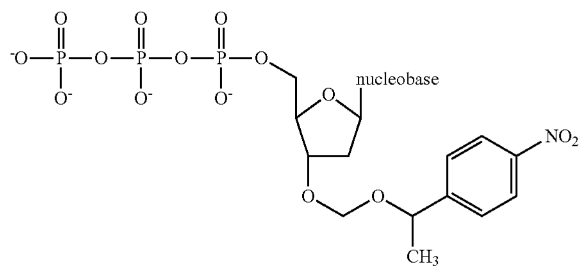
(3B)
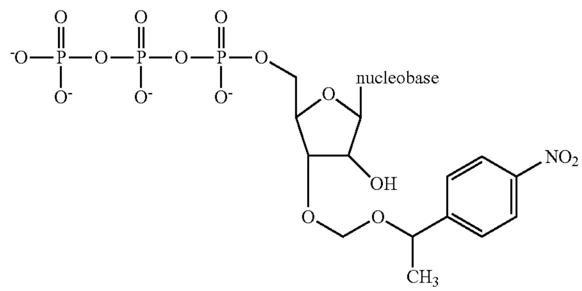
(4A)
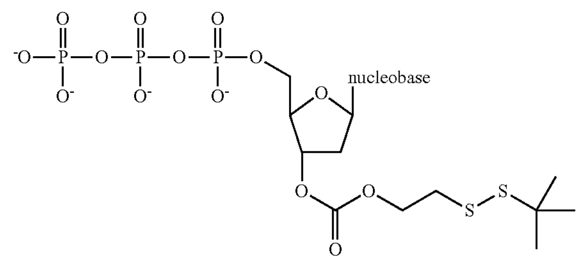
-continued
(4B)
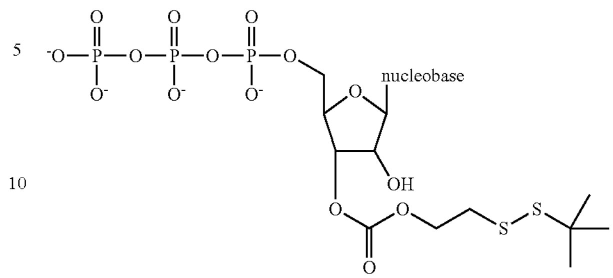
(5A)
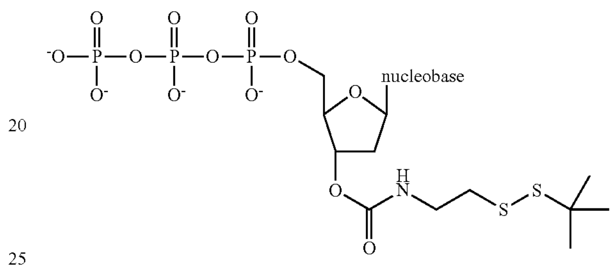
(5B)
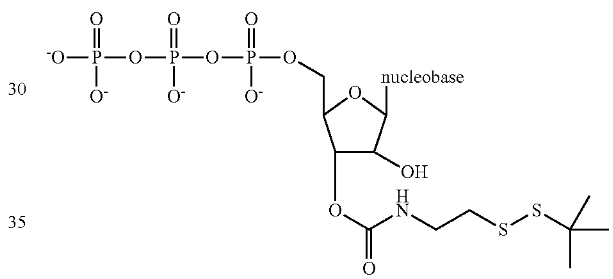
(6A)
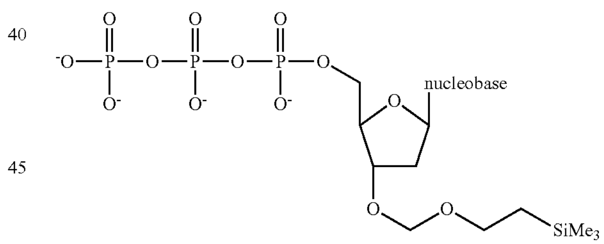
(6B)
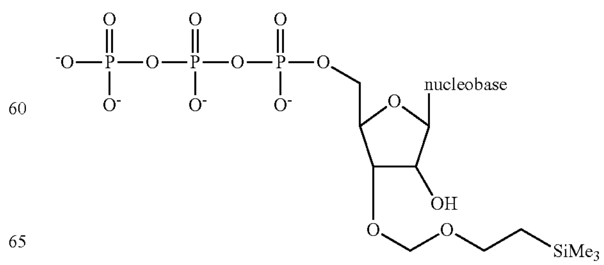

-continued (7A)

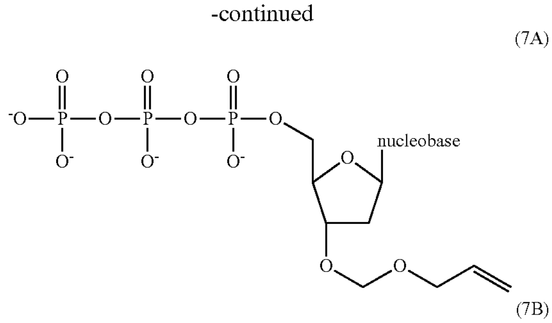

(7B)

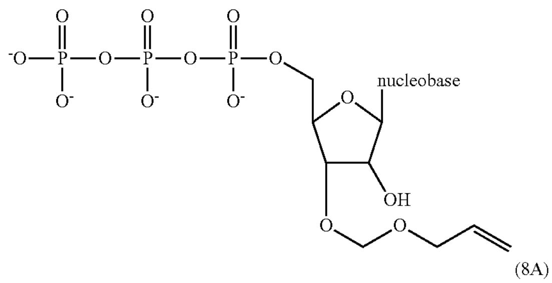

(8A)

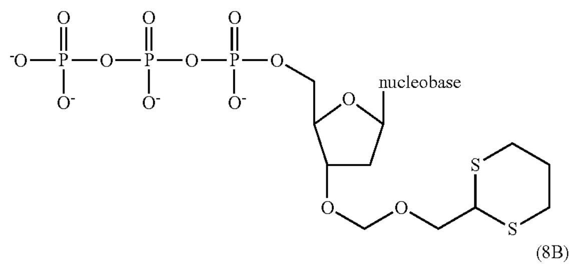

(8B)

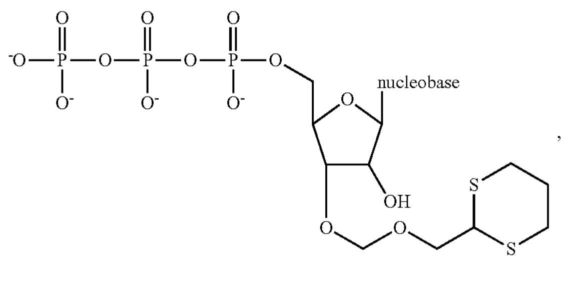

, wherein nucleobase is selected from the group consisting of adenine (A), cytosine (C), guanine (G), uracil (U) and thymine (T).

In one aspect, there is provided a method of preparing a blocked nucleoside triphosphate as disclosed herein, the method comprising:

(i) providing a nucleoside having general formula (VII):

(VII)

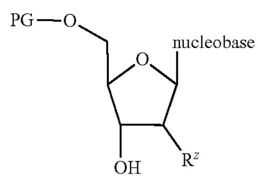

wherein $R^z$ is H or OH and PG is a protecting group;

(ii) introducing a removable terminating group (RT) to the nucleoside having general formula (VII) to obtain a nucleoside having general formula (IX):

(IX)

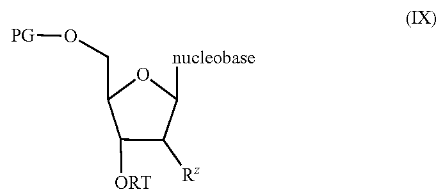

wherein $R^z$ is H or OH and RT is selected from any one of the general formulae (VIIIa), (VIIIb), (VIIIc), (VIIId), (VIIIe) and (VIIIf):

(VIIIa)

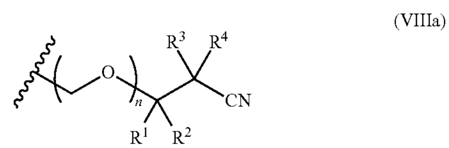

(VIIIb)

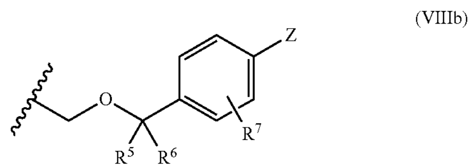

(VIIIc)

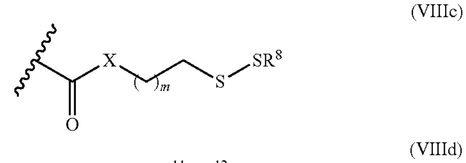

(VIIId)

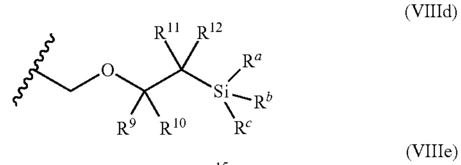

(VIIIe)

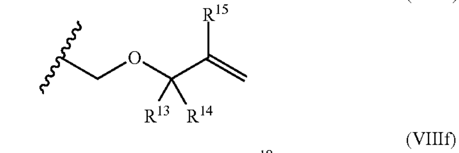

(VIIIf)

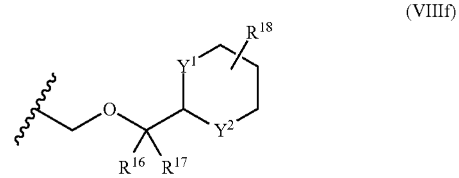

wherein n=0 or 1;

m=0 to 20;

$R^1$, $R^2$, $R^3$, $R^4$, $R^5$, $R^6$, $R^a$, $R^b$ and $R^c$ are each independently selected from hydrogen, alkyl, alkenyl, aryl and heteroaryl;

$R^7$ is selected from hydrogen, alkyl, halogen, —$OR^{19}$, —$NR^{20}R^{21}$ and —$SR^{22}$, wherein $R^{19}$, $R^{20}$, $R^{21}$ and $R^{22}$ are independently selected from hydrogen, alkyl, alkenyl, aryl and heteroaryl;

$R^8$, $R^9$, $R^{10}$, $R^{11}$, $R^{12}$, $R^{13}$, $R^{14}$, $R^{15}$, $R^{16}$, $R^{17}$ and $R^{18}$ are independently selected from hydrogen, alkyl, alkenyl, aryl and heteroaryl;

X is a heteroatom selected from O, S and NH;

$Y^1$ and $Y^2$ are independently selected from S and Se;

Z is a chemical moiety that is capable of being released under suitable conditions to trigger removal of the adjacent benzyl linker; and with the proviso that when n=0, $R^1$ and $R^2$ are both not hydrogen;

(iii) removing the protecting group (PG) from the nucleoside having general formula (IX) to obtain a nucleoside having general formula (X):

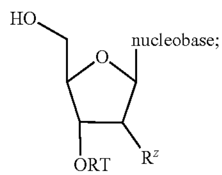

(X)

and (iv) converting the hydroxy group in the nucleotide having general formula (X) to triphosphate group to obtain a blocked nucleoside triphosphate as disclosed herein.

In one embodiment, Z is $NO_2$.

In one embodiment, $R^a$, $R^b$ and $R^c$ are each methyl.

In one embodiment, the protecting group is selected from the group consisting of dimethoxytrityl (DMT), tert-butyldimethylsilyl (TBS), 9-phenylxanthen-9-yl and 9-(p-tolyl)-xanthen-9-yl, tri-iso-propylsilyloxy-methyl (TOM), trimethylsilyl (TMS) and triisopropylsilyl (TIPS).

Definitions

The term "alkyl" as a group or part of a group refers to a straight or branched aliphatic hydrocarbon group having 1 to 12 carbon atoms, 1 to 10 carbon atoms, 1 to 6 carbon atoms, or 1, 2, 3, 4, 5, 6, 7, 8, 9, 10, 11 or 12 carbon atoms. Examples of suitable straight and branched $C_1$-$C_6$ alkyl substituents include methyl, ethyl, n-propyl, 2-propyl, isopropyl, n-butyl, isobutyl, sec-butyl, t-butyl, hexyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl and the like. The group may be a terminal group or a bridging group.

The term "alkenyl" as a group or part of a group denotes an aliphatic hydrocarbon group containing at least one carbon-carbon double bond and which may be straight or branched having 2 to 12 carbon atoms, 2 to 10 carbon atoms, 2 to 6 carbon atoms, or 2, 3, 4, 5, 6, 7, 8, 9, 10, 11 or 12 carbon atoms in the chain. The group may contain a plurality of double bonds and the orientation about each double bond is independently E or Z. Exemplary alkenyl groups include, but are not limited to, ethenyl, vinyl, allyl, 1-methylvinyl, 1-propenyl, 2-propenyl, 2-methyl-1-propenyl, 2-methyl-1-propenyl, 1-butenyl, 2-butenyl, 3-butentyl, 1,3-butadienyl, 1-pentenyl, 2-pententyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, 1-heptenyl, 2-heptentyl, 3-heptenyl, 1-octenyl, 1-nonenyl, 1-decenyl. The group may be a terminal group or a bridging group.

The term "aryl" as a group or part of a group denotes (i) an optionally substituted monocyclic, or fused polycyclic, aromatic carbocycle (ring structure having ring atoms that are all carbon) preferably having from 5 to 20, or 5, 6, 7, 8, 9, 10, 11, 12, 13, 14, 15, 16, 17, 18, 19 or 20 carbon atoms per ring. Examples of aryl groups include but are not limited to phenyl, tolyl, xylyl, naphthyl, anthracenyl, phenanthrenyl, fluorenyl, indenyl or indanyl and the like.

The term "heteroaryl" as a group or part of a group refers to groups containing an aromatic ring (preferably a 5- or 6-membered aromatic ring) having one or more carbon atoms (for example 1 to 6 carbon atoms) in the ring replaced by a heteroatom. Suitable heteroatoms may include nitrogen (N) or (NH), oxygen (O) and sulfur (S). Examples of heteroaryl include but are not limited to thiophene, benzothiophene, benzofuran, benzimidazole, benzoxazole, benzothiazole, benzisothiazole, naphtha[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenantridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl and the like. The group may be a terminal group or a bridging group.

The term "halogen" represents chlorine, fluorine, bromine or iodine. The term "halo" represents chloro, fluoro, bromo or iodo.

The terms "coupled" or "connected" as used in this description are intended to cover both directly connected or connected through one or more intermediate means, unless otherwise stated.

The term "associated with", used herein when referring to two elements refers to a broad relationship between the two elements. The relationship includes, but is not limited to a physical, a chemical or a biological relationship. For example, when element A is associated with element B, elements A and B may be directly or indirectly attached to each other or element A may contain element B or vice versa.

The term "adjacent" used herein when referring to two elements refers to one element being in close proximity to another element and may be but is not limited to the elements contacting each other or may further include the elements being separated by one or more further elements disposed therebetween.

The term "and/or", e.g., "X and/or Y" is understood to mean either "X and Y" or "X or Y" and should be taken to provide explicit support for both meanings or for either meaning.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. For example, when "comprising" is used, reference to a "one" feature is also intended to be a reference to "at least one" of that feature. Terms such as "consisting", "consist", and the like, may in the appropriate context, be considered as a subset of terms such as "comprising", "comprise", and the like. Therefore, in embodiments disclosed herein using the terms such as "comprising", "comprise", and the like, it will be appreciated that these embodiments provide teaching for corresponding embodiments using terms such as "consisting", "consist", and the like.

Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. The intention of the above specific disclosure is applicable to any depth/breadth of a range.

Additionally, when describing some embodiments, the disclosure may have disclosed a method and/or process as a particular sequence of steps. However, unless otherwise required, it will be appreciated that the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

Furthermore, it will be appreciated that while the present disclosure provides embodiments having one or more of the features/characteristics discussed herein, one or more of these features/characteristics may also be disclaimed in other alternative embodiments and the present disclosure provides support for such disclaimers and these associated alternative embodiments.

DESCRIPTION OF EMBODIMENTS

Exemplary, non-limiting embodiments of a method of synthesizing a single-stranded nucleotide sequence, blocked nucleoside triphosphates for said method and a method of preparing said blocked nucleoside triphosphates are disclosed hereinafter.

There is provided a method of synthesizing a single-stranded nucleotide sequence, the method comprising: (i) adding a blocked nucleoside triphosphate to an initiator nucleotide sequence to incorporate a corresponding blocked nucleotide thereto in the presence of a polymerase. In various embodiments, the method comprises adding the blocked nucleoside triphosphate to the initiator nucleotide sequence in the 3' direction (e.g. to the 3' position of the initiator nucleotide sequence).

In various embodiments, the blocked nucleoside triphosphate is blocked at its 3'-O position with a terminating group, blocking group or protecting group. In some embodiments, the terms terminating group, blocking group or protecting group may be interchangeably used. In various embodiments, the terminating group, blocking group or protecting group is removable.

In various embodiments, the blocked nucleoside triphosphate has one of the general formulae (I), (II), (III), (IV), (V) and (VI):

(I)

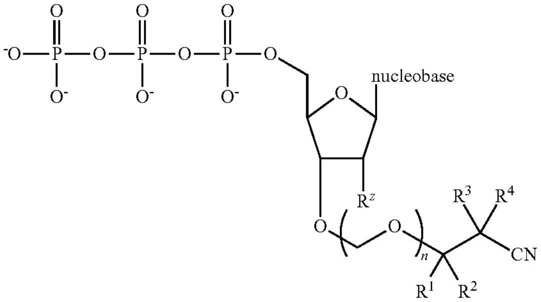

(II)

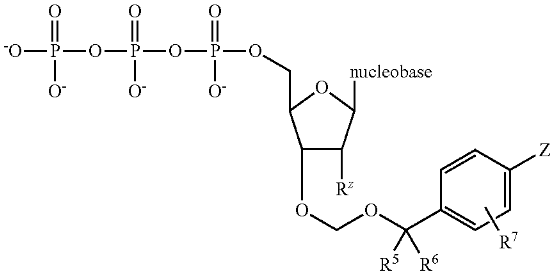

(III)

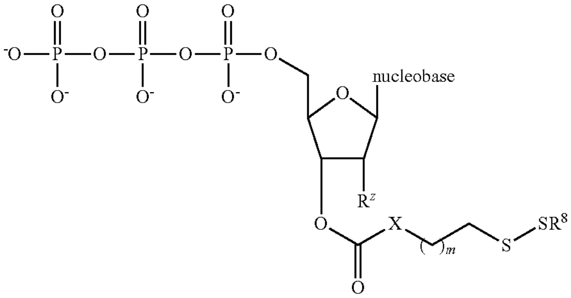

(IV)

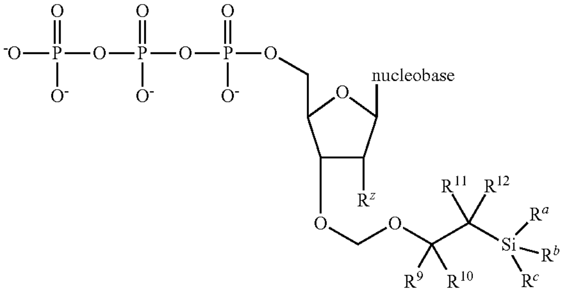

(V)

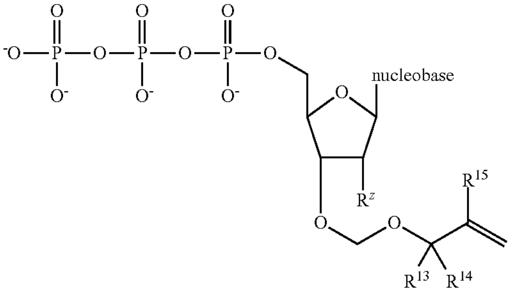

-continued (VI)

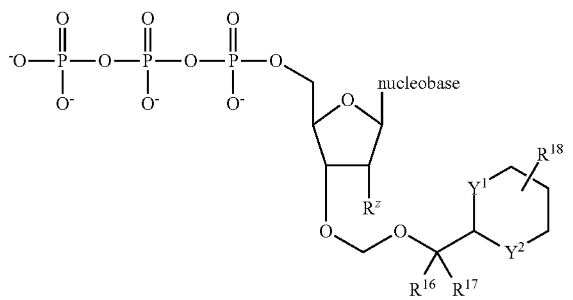

wherein n=0 or 1;

m=0 to 20;

$R^z$ is H or OH;

$R^1$, $R^2$, $R^3$, $R^4$, $R^5$, $R^6$, $R^a$, $R^b$ and $R^c$ are each independently selected from hydrogen, alkyl, alkenyl, aryl and heteroaryl; $R^7$ is selected from hydrogen, alkyl, halogen, —$OR^{19}$, —$NR^{20}R^{21}$ and —$SR^{22}$, wherein $R^{19}$, $R^{20}$, $R^{21}$ and $R^{22}$ are independently selected from hydrogen, alkyl, alkenyl, aryl and heteroaryl; $R^8$, $R^9$, $R^{10}$, $R^{11}$, $R^{12}$, $R^{13}$, $R^{14}$, $R^{15}$, $R^{16}$, $R^{17}$ and $R^{18}$ are independently selected from hydrogen, alkyl, alkenyl, aryl and heteroaryl; X is a heteroatom selected from O, S and NH; $Y^1$ and $Y^2$ are independently selected from S and Se; and Z is a chemical moiety that is capable of being released under suitable conditions to trigger removal of the adjacent benzyl linker.

In various embodiments, m is 0, 1, 2, 3, 4, 5, 6, 7, 8, 9, 10, 11, 12, 13, 14, 15, 16, 17, 18, 19 or 20. In various embodiments, one of the hydrogen atoms connected to the carbon atom at the 2' position of the ribose moiety is optionally replaced with OH. In various embodiments, $R^1$, $R^2$, $R^3$, $R^4$, $R^5$ and $R^6$ are each independently selected from hydrogen, methyl, ethyl, n-propyl, 2-propyl, isopropyl, n-butyl, isobutyl, sec-butyl, t-butyl, pentyl or hexyl.

In various embodiments, at least one of $R^3$ and $R^4$ is H. In various embodiments, $R^3$ and $R^4$ are H.

In various embodiments, $R^7$ is selected from hydrogen, alkyl, halogen, —$OR^{19}$, —$NR^{20}R^{21}$ and —$SR^{22}$, wherein $R^{19}$, $R^{20}$, $R^{21}$ and $R^{22}$ are independently selected from hydrogen and alkyl. In various embodiments, $R^7$ is selected from hydrogen, alkyl, halogen, hydroxy, alkoxy, amine, thioalkyl and alkylthiol. In various embodiments, $R^7$ is alkyl selected from methyl, ethyl, n-propyl, 2-propyl, isopropyl, n-butyl, isobutyl, sec-butyl, t-butyl, pentyl or hexyl. In various embodiments, $R^7$ is halogen selected from chloro, fluoro, bromo or iodo. In various embodiments, $R^7$ is alkoxy selected from methoxy, ethoxy, n-propoxy, 2-propoxy, isopropoxy, n-butoxy, isobutoxy, sec-butoxy, t-butoxy, pentoxyl or heoxy. In various embodiments, $R^7$ is amine selected from primary amine or secondary amine. For example, $R^7$ may be methylamine, dimethylamine, ethylamine, diethylamine, propylamine, isopropylamine, di-n-propylamine, butylamine, cyclohexylamine, pentylamine or the like. In various embodiments, $R^7$ is thioalkyl selected from thiomethyl, thioethyl, thiopropyl, thiobutyl, thiopentyl, thiohexyl or the like.

In various embodiments, $R^8$, $R^9$, $R^{10}$, $R^{11}$, $R^{12}$, $R^{13}$, $R^{14}$, $R^{15}$, $R^{16}$, $R^{17}$ and $R^{18}$ are independently selected from hydrogen, alkyl, aryl and heteroaryl. In various embodiments, $R^8$, $R^9$, $R^{10}$, $R^{11}$, $R^{12}$, $R^{13}$, $R^{14}$, $R^{15}$, $R^{16}$, $R^{17}$ is alkyl selected from methyl, ethyl, n-propyl, 2-propyl, isopropyl, n-butyl, isobutyl, sec-butyl, t-butyl, pentyl or hexyl. In various embodiments, $R^8$, $R^9$, $R^{10}$, $R^{11}$, $R^{12}$, $R^{13}$, $R^{14}$, $R^{15}$, $R^{16}$, $R^{17}$ is aryl or heteroaryl selected from phenyl, tolyl, xylyl, naphthyl, furanyl, pyrrolyl, imidazolyl, pyrazolyl, pyridinyl or pyrimidinyl.

In various embodiments, $R^a$, $R^b$ and $R^c$ are each an alkyl e.g. each a methyl.

In various embodiments, Z is a nitrogen containing moiety or Z comprises a N atom. In various embodiments, Z is selected from the group consisting of nitro ($NO_2$), NHOH, nitric oxide (NO), $N_3$, $NR_2O$ (e.g. N-dialkyl oxide), amide, diazo, where R is independently selected from one or more of the groups defined for $R^1$ to $R^{18}$ above. In various embodiments, by reduction of $NO_2$, NHOH, NO, $N_3$, $NR_2O$ (N-dialkyl oxide), hydrolysis of amide group (chemically or by using a peptidase enzyme), cleavage of a diazo group (chemically or by using an azoreductase enzyme) or an oxidation event, the release of the desired $NR_2$ group (for instance by using a linker where an oxidation leads to the linker decomposition unveiling the $NR_2$ group) may be achieved.

In various embodiments, instead of $NR_2$ it may also be an oxygen (OH) being released through ester hydrolysis (chemically or by using an esterase enzyme), carbonate hydrolysis, oxidation of carbonyl moiety (chemically with peracid or by using a Baeyer-Villiger monooxygenase enzyme) or removal of any phenol protecting group. In various embodiments therefore, Z is an ester, carbonate or phenol protecting group. Z may also be a sulfur atom, in other words, Z may be designed in such a way to facilitate an event leading to the release of an $NR_2$, OH or SH moiety which in turn triggers the removal of the benzyl linker and recovery of 3'-OH nucleoside. In various embodiments, Z is a chemical moiety that is capable of being converted to —$NH_2$ under reductive and/or oxidative conditions.

In various embodiments, the blocked nucleoside triphosphate has one of the general formulae (II-1) and (IV-1):

(11-1)

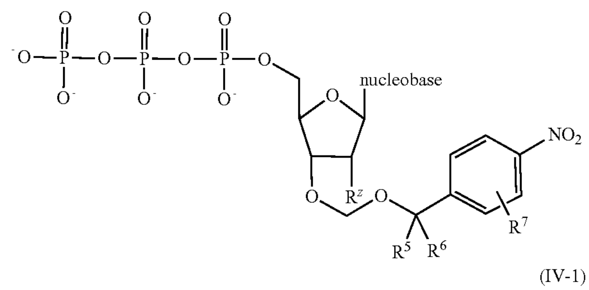

(IV-1)

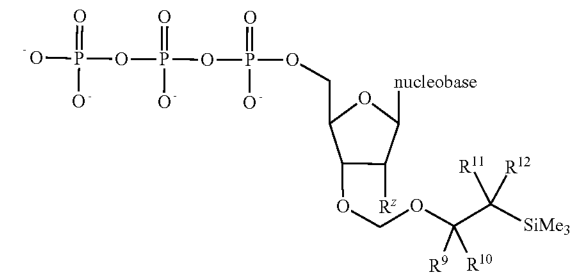

In various embodiments, the removable terminating group is bigger or much bigger than those of conventional reversible terminators which typically have their 3'-positions blocked with very small protecting groups like —OAc, —$OCH_2N_3$ or —$ONH_2$ in order to be tolerated by the polymerase.

Advantageously, as embodiments of the removable terminating group are efficiently incorporated by the polymerase, the removable terminating group stabilizes the complex comprising the polymerase and triphosphate monomer, thereby enabling efficient enzymatic elongation.

In various embodiments, the blocked nucleoside triphosphate comprises a deoxyribonucleoside triphosphate. The deoxyribonucleoside triphosphate may be selected from the group consisting of deoxyadenosine triphosphate, deoxycytidine triphosphate, deoxyguanosine triphosphate and deoxythymidine triphosphate.

In various embodiments, the blocked nucleoside triphosphate is selected from one of the structures as shown in Scheme 3.

2-cyanoethyl ether (herein termed "CE")-RT analogues:

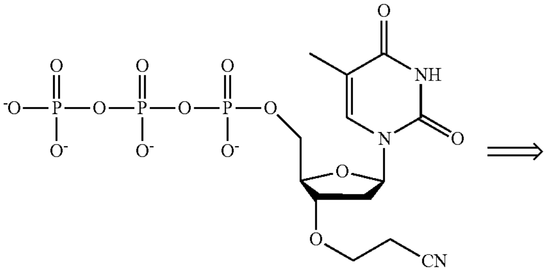

CE-dTTP

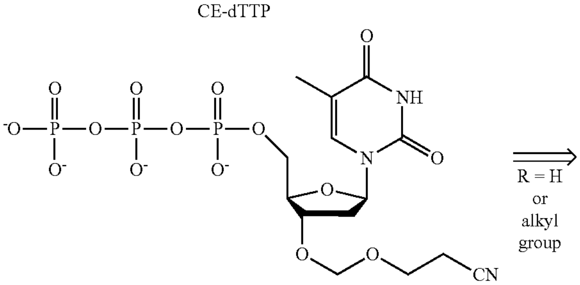

CEM-dTTP

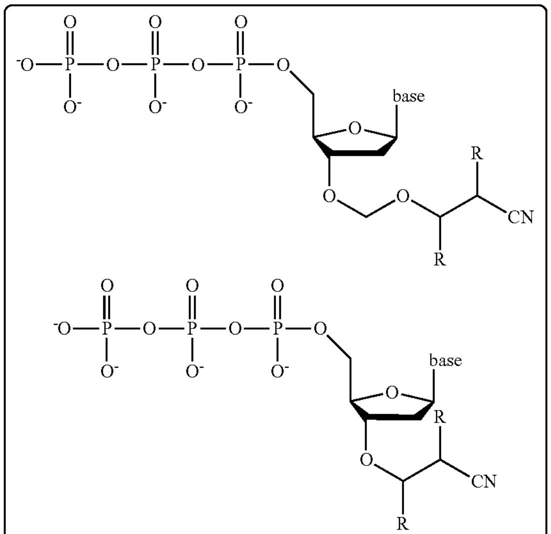

Markush based on CE- and CEM-dNTP

Other bases for CE-RTs:

CE-dTTP

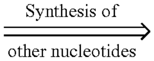

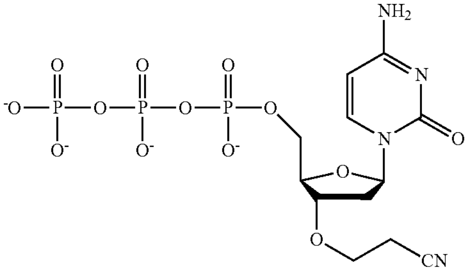

CE-dCTP

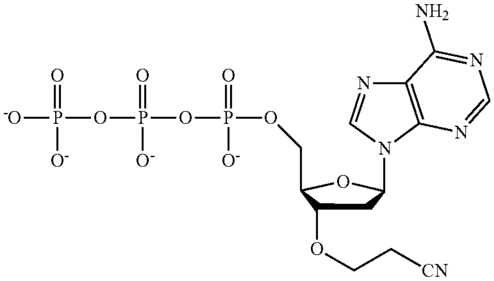

CE-dATP

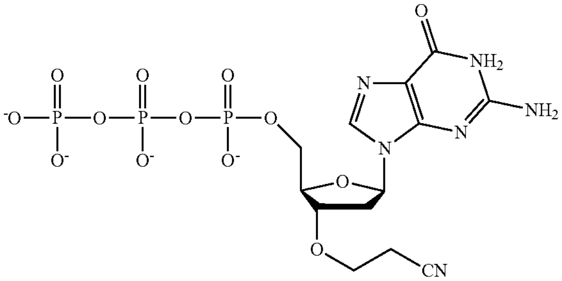

CE-dGTP 4-nitrobenzyloxy-methyl (herein termed "PNBA")-RT analogues:

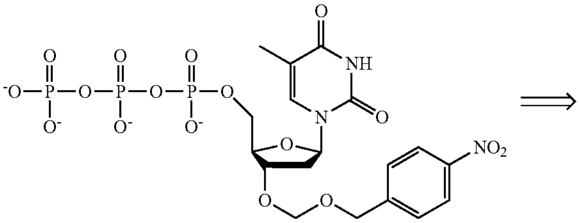

PNBA-dTTP

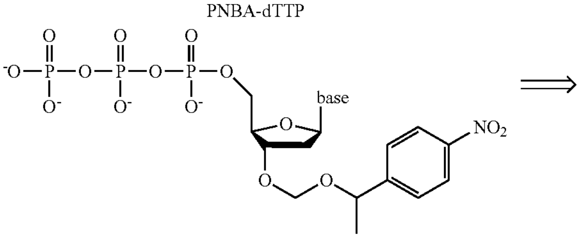

Me-PNBA-dNTP

-continued

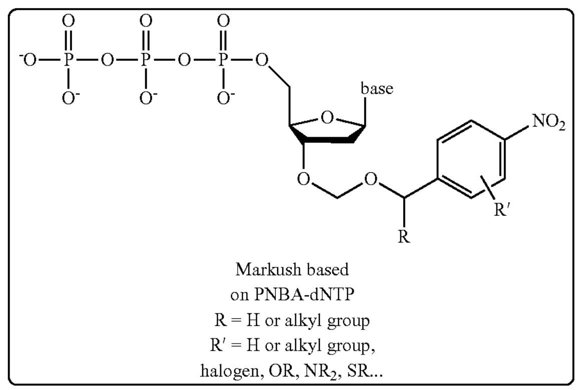

Markush based on PNBA-dNTP
R = H or alkyl group
R′ = H or alkyl group, halogen, OR, $NR_2$, SR...

Disulfide carbonate (herein termed "DT")-RT analogues:

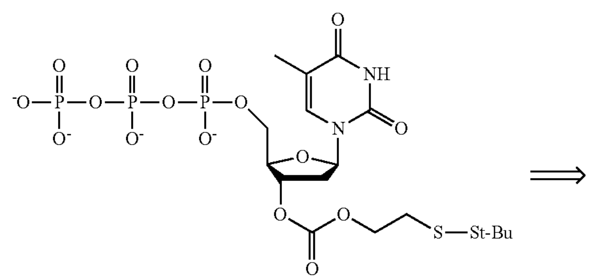

DTO-dTTP

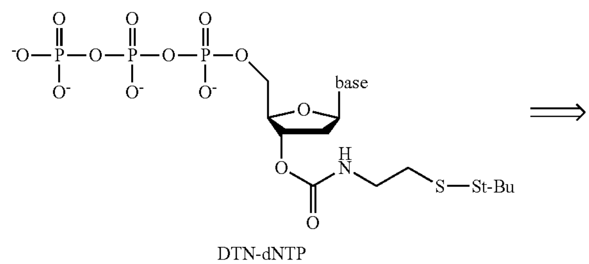

DTN-dNTP

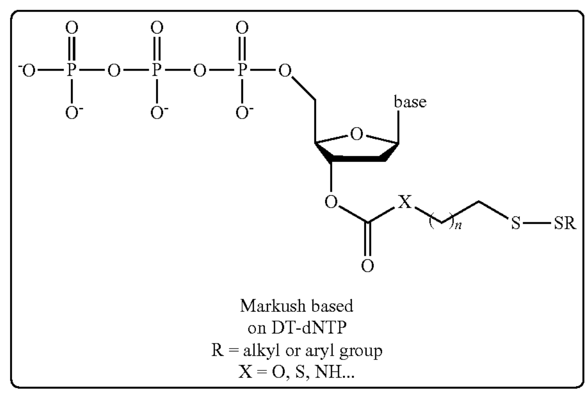

Markush based on DT-dNTP
R = alkyl or aryl group
X = O, S, NH...

Analogues of 2-(trimethylsilyl)ethoxymethyl (herein termed "SEM"), (allyloxy)methyl (herein termed "AL" or "ALM") and dithianemethyl acetal (herein termed "DMA"):

Scheme 3. Blocked nucleoside triphospate chemical structures and analogues

SEM-dTTP
AL-dTTP
DMA-dTTP

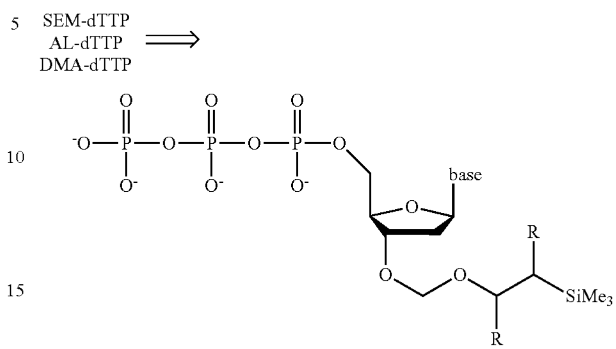

Markush based on SEM-dNTP
R = alkyl or aryl group

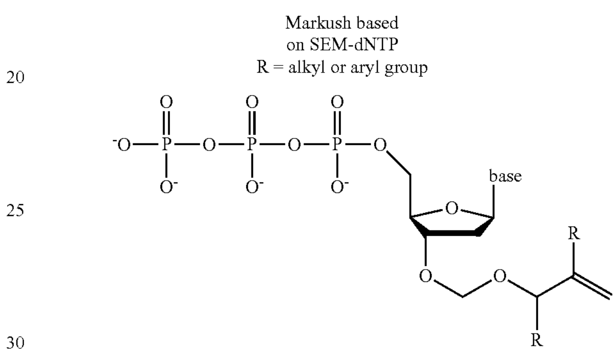

Markush based on AL-dNTP
R = alkyl or aryl group

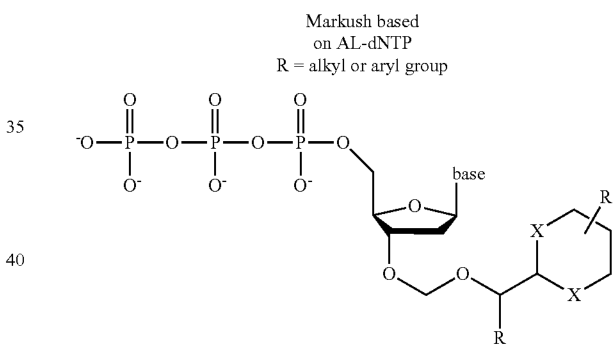

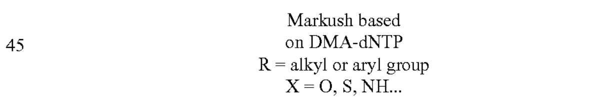

Markush based on DMA-dNTP
R = alkyl or aryl group
X = O, S, NH...

In various embodiments, the blocked nucleoside triphosphate is selected from the following:

(1A)

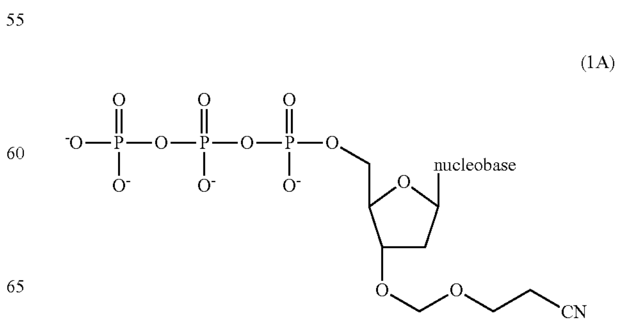

-continued
(1B)
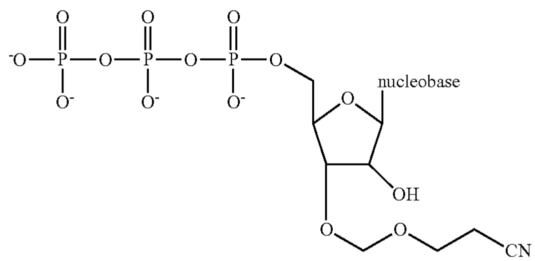
(2A)
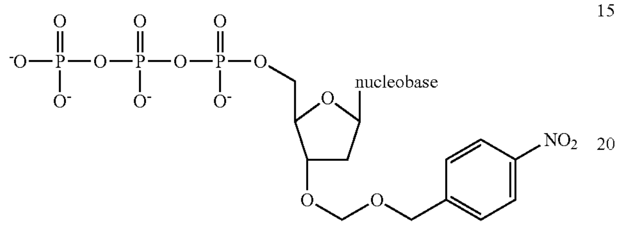
(2B)
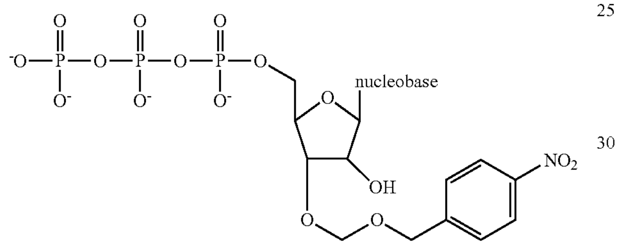
(3A)
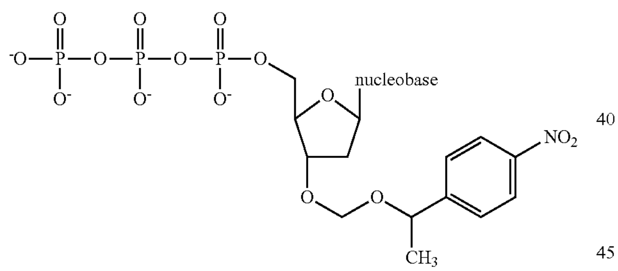
(3B)
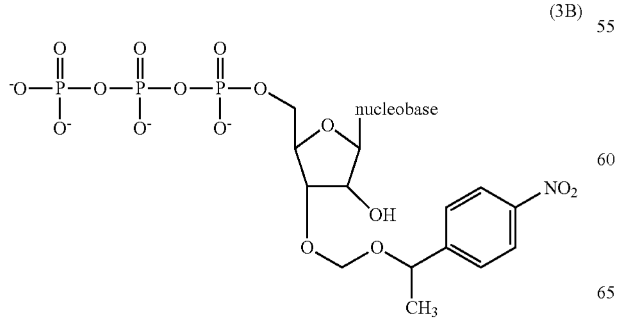
-continued
(4A)
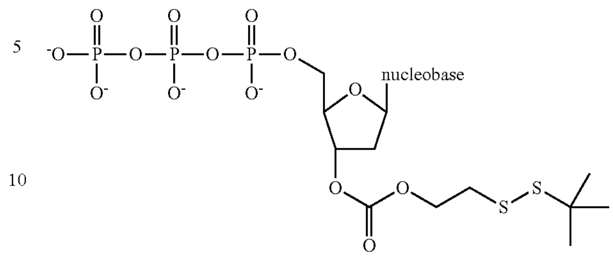
(4B)
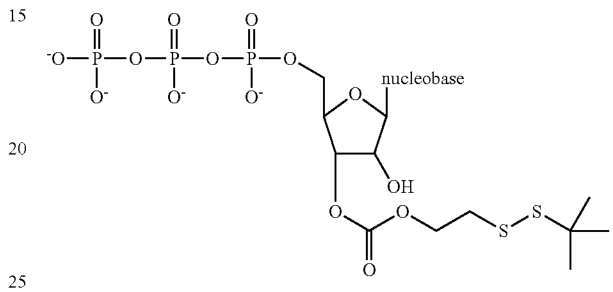
(5A)
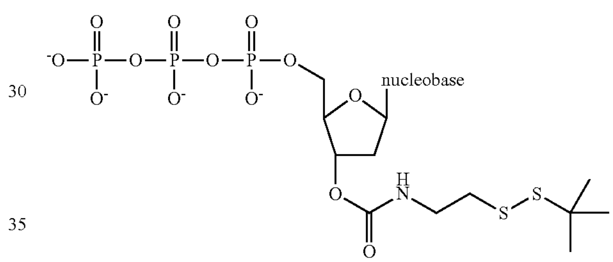
(5B)
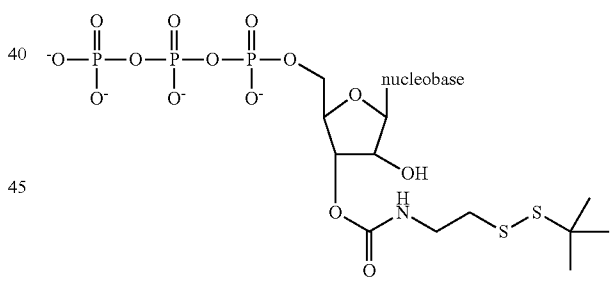
(6A)
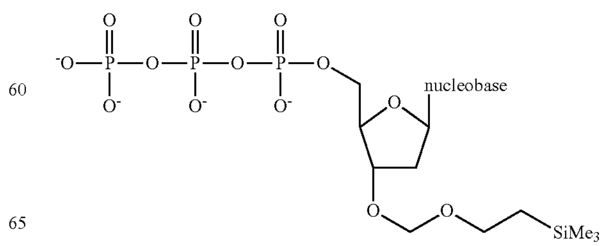

-continued (6B)

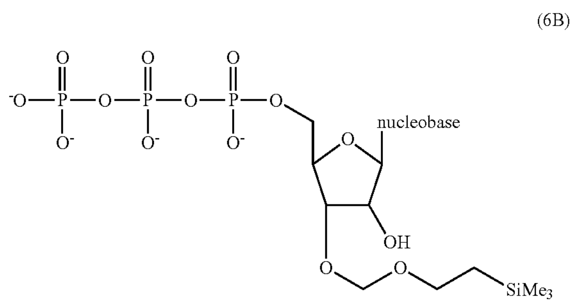

(7A)

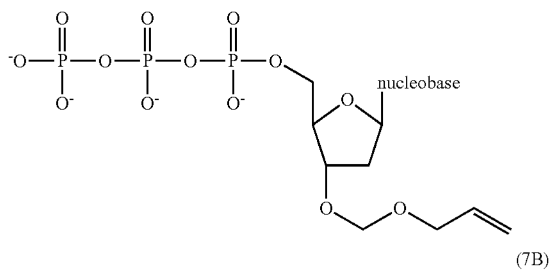

(7B)

(8A)

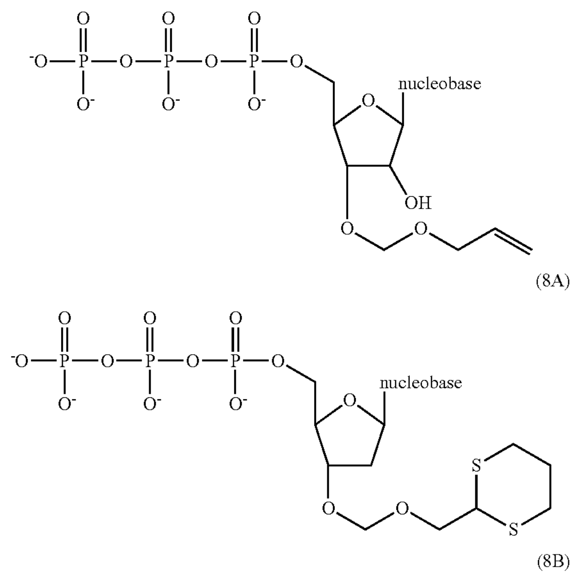

(8B)

(9A)

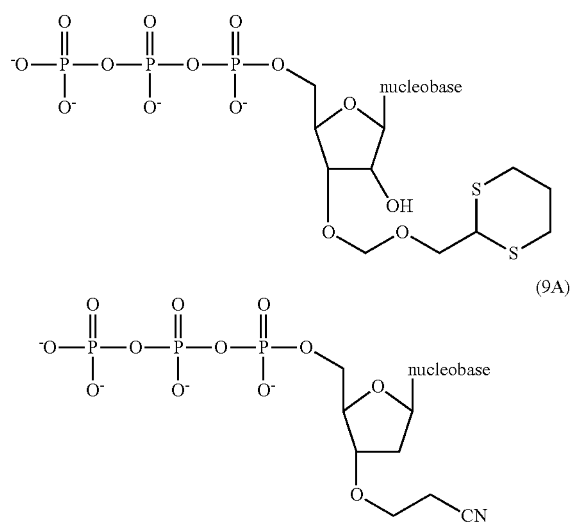

-continued (9B)

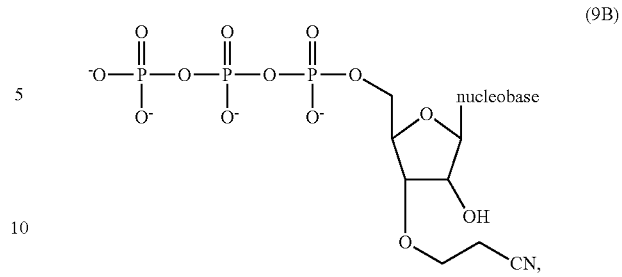

wherein nucleobase is selected from the group consisting of adenine (A), cytosine (C), guanine (G), uracil (U) and thymine (T).

In various embodiments, the method further comprises (ii) removing the removable terminating group from the incorporated blocked nucleotide to obtain a corresponding nucleotide unblocked at the 3'-O position.

In various embodiments, the method further comprises (iii) adding a blocked nucleoside triphosphate of any one of the general formulae (I), (II), (III), (IV), (V) and (VI) to the 3'-O position of the unblocked nucleotide obtained in step (ii) in the presence of a polymerase. In various embodiments, the method further comprises (iii-2) adding a natural nucleoside triphosphate to the 3'-O position of the unblocked nucleotide obtained in step (ii) in the presence of a polymerase. The natural nucleoside triphosphate may be deoxynucleotidyl triphosphate or deoxynucleoside triphosphates selected from deoxyadenosine triphosphate, deoxycytidine triphosphate, deoxyguanosine triphosphate and deoxythymidine triphosphate. The natural nucleoside triphosphate may be ribonucleoside triphosphate selected from riboadenosine triphosphate, ribocytidine triphosphate, riboguanosine triphosphate and ribouridine triphosphate.

In various embodiments, the method further comprises optionally repeating step (ii) and/or step (iii) one or more times until a single-stranded nucleotide sequence of a desired length is obtained.

In various embodiments, step (ii) and step (iii) make up a single cycle. In each cycle, step (ii) and step (iii) may be repeated in a stepwise serial manner until a single stranded nucleotide sequence of a desired length is obtained. The cycle comprising step (ii) and step (iii) may be repeated at least once, at least twice, at least thrice, at least four times, at least five times, at least six times, at least seven times, at least eight times, at least nine times or at least ten times. Advantageously, embodiments of the blocked nucleoside triphosphates disclosed herein are recognized by template independent polymerases and cleavage/removal of the removable terminating/blocking groups may be performed under a wide range of reaction conditions. In various embodiments, the cleaving/removal of the removable terminating/blocking groups enables a process elongating/extending/lengthening the initiator nucleotide sequence through a series of iteration cycles, thereby leading to successful enzymatic synthesis of single-stranded nucleotide sequence.

In various embodiments, the polymerase is a template independent polymerase. In various embodiments, the template independent polymerase is an engineered template independent polymerase, a recombinant template independent polymerase, a wild-type template independent polymerase or the like. In various embodiments, the polymerase is a template independent polymerase selected from a deoxyribonucleic acid (DNA) polymerase or a ribonucleic acid (RNA) polymerase. In various embodiments, the polymerase comprises a deoxyribonucleic acid (DNA) polymerase. The deoxyribonucleic acid (DNA) polymerase may be terminal deoxynucleotidyl transferase (TdT) and/or polymerase theta (POLQ). The TdT may be an engineered, a recombinant or a wild-type TdT. In various embodiments, TdT is a commercially available TdT. Other polymerases that may be used include modified enzymes and natural enzymes.

In various embodiments, the step (ii) of removing the removable terminating group is performed in one or more of the conditions: aqueous, organic, basic, reductive, acidic, metal-catalyzed, enzyme-catalyzed and electrochemically controlled.

In various embodiments, the removal of a removable terminating group from a blocked nucleoside triphosphate having general formula (I) is carried under basic conditions at a temperature ranging from about 5° C. to about 100° C., from about 10° C. to about 95° C., from about 15° C. to about 90° C., from about 20° C. to about 85° C., from about 25° C. to about 80° C., from about 30° C. to about 75° C., from about 35° C. to about 70° C., or from about 40° C. to about 65° C. The basic conditions may comprise aqueous solutions containing one or more base(s) that include but is not limited to ammonium hydroxide ($NH_4OH$).

In various embodiments, the removal of a removable terminating group from a blocked nucleoside triphosphate having general formula (II) is carried under reductive conditions at a temperature ranging from about 0° C. to about 50° C., from about 5° C. to about 45° C., from about 10° C. to about 40° C., from about 15° C. to about 35° C., from about 20° C. to about 30° C., or about 25° C. The reductive conditions may comprise aqueous solutions containing one or more reducing agent(s) that include but is not limited to dithiothreitol (DTT) and tris(2-carboxyethyl)phosphine (TCEP).

In various embodiments, the removal of a removable terminating group from a blocked nucleoside triphosphate having general formula (III) is carried under basic conditions or mildly basic conditions at a pH range of from about 7 to about 14, from about 8 to about 13, from about 9 to about 12, or from about 10 to about 11. In various embodiments, the removal of a removable terminating group from a blocked nucleoside triphosphate having general formula (III) is carried in aqueous solutions of fluoride sources that include but is not limited to tetra-n-butylammonium fluoride (TBAF) and potassium fluoride (KF).

In various embodiments, the removal of a removable terminating group from a blocked nucleoside triphosphate having general formula (IV) is carried out in the presence of transition metal(s) or transition metal salt(s) that include but is not limited to palladium, ruthenium, rhodium, platinum and their salts thereof.

In various embodiments, the removal of a removable terminating group from a blocked nucleoside triphosphate having general formula (V) is carried out under reductive conditions such as in the presence of a reductive enzyme. The reactive conditions may also be electrochemically controlled in an electrochemical system. In various embodiments, the removal of a removable terminating group from a blocked nucleoside triphosphate having general formula (V) may be further carried out under acidic conditions at a pH range of from about 0 to about 7, from about 1 to about 6, from about 2 to about 5, or from about 3 to about 4.

In various embodiments, the removal of a removable terminating group from a blocked nucleoside triphosphate having general formula (VI) is carried out under oxidative conditions or mildly oxidative conditions at a temperature ranging from about 0° C. to about 50° C., from about 5° C. to about 45° C., from about 10° C. to about 40° C., from about 15° C. to about 35° C., from about 20° C. to about 30° C., or about 25° C. In various embodiments, the method is substantially devoid of the use of an oxidizing agent such as sodium nitrite. In various embodiments, the removal of a removable terminating group from a blocked nucleoside triphosphate disclosed herein (e.g. having general formula (VI)) is carried out with sodium periodate, followed by subjecting to mild basic conditions at a pH of about 8, in the presence of a base. Examples of the base include but are not limited to potassium carbonate ($K_2CO_3$) and aniline ($PhNH_2$).

In various embodiments, the step (ii) of removing the removable terminating group is adapted to be carried out or is carried out in/under aqueous conditions. Advantageously, embodiments of the blocked nucleoside triphosphate disclosed herein may undergo reversible deprotection in aqueous medium, thus reducing/eliminating the need for extra washing steps. In various embodiments therefore, the blocked nucleoside triphosphate disclosed herein allows single-stranded nucleotide sequences to be synthesized more efficiently in a simple manner as compared to conventional reversible terminators which generally require organic solvents for deprotection, therefore paving the way for a practical enzymatic synthesis of nucleic acids. Accordingly, in various embodiments, the step (ii) of removing the removable terminating group is not performed in a fully organic medium (e.g. water-free TBAF in THF medium).

Even more advantageously, at least the step (i) of adding a blocked nucleoside triphosphate to an initiator nucleotide sequence to incorporate a corresponding blocked nucleotide thereto in the presence of a polymerase and step (ii) of removing the removable terminating group are capable of being performed or are performed in aqueous conditions. Still even more advantageously, the whole/entire nucleotide sequence synthesis cycle may be performed solely in/under aqueous solutions i.e. the methods do not require a single step to be performed in an organic medium. In various embodiments, each step of the method is adapted to be carried out in aqueous conditions. Unlike conventional methods which generally require organic solvents in synthesis of nucleotide sequences, embodiments of the method disclosed herein allows the entire synthesis including all steps (i) to (iv) to be performed solely in aqueous solution, thereby making the presently disclosed method an environmentally benign and friendly process. As it will be appreciated, it is generally more challenging to make the entire method (from synthesis to deprotection) work in water as compared to the case where at least one step is allowed to be carried out in a fully organic medium (e.g. deprotection step) and the present inventors have surprisingly shown that this is possible for the presently disclosed reversible terminators.

In various embodiments, the method is substantially devoid of the formation of side products or by-products that are reactive to the nucleobases of the nucleotide sequence. Advantageously, embodiments of the method avoid the possibility of forming reactive side products such as strong electrophiles and nucleophiles that reacts with and/or damages nucleobases of the nucleotide sequence, thereby leading to production of spurious side products. In various embodiments therefore, the removal of the removable terminating group from the blocked nucleoside triphosphate disclosed herein is clean and complete and therefore, does not release side products that are reactive. In various embodiments, the removal of the removable terminating group from the blocked nucleoside triphosphate disclosed herein releases side products that are chemically inert and/or unreactive. In various embodiments, the method is substantially devoid of the addition/use of a scavenger for the purpose of removing/deactivating such reactive side products (e.g. such as those capable of scavenging $CH_2NH_2^+$ and/or $CH_2O$).

In various embodiments, removal of the removable terminating group from blocked nucleoside triphosphates disclosed herein (e.g. of general formula (IV) or (V)), does not result in a release of undesirable side products such as reactive electrophiles.

The nucleobase may be selected from the group consisting of adenine (A), cytosine (C), guanine (G), thymine (T), uracil (U), uric acid, isocytosine, isoguanine, 2-aminopurine, 2,6-diaminopurine, 5-fluorouracil, 5-bromouracil, 5-chlorouracil, 5-iodouracil, hypoxanthine, xanthine, acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N-6-isopentenyladenine, 1-methylguanine, 1-methylinosine, 2,2-dimethylguanine, 2-methyladenine, 2-methylguanine, 3-methylcytosine, 5-methylcytosine, $N_6$-adenine, 7-methylguanine, 5-methylaminomethyluracil, methoxyaminomethyl-2-thiouracil, beta-D-mannosylqueosine, 5'-methoxycarboxymethyluracil 5-methoxyuracil, 2-methylthio-N-6-isopentenyladenine, uracil-5-oxy acetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil and 3-(3-amino-3-N-2-carboxypropyl) uracil. Other unnatural nucleobases may also be used, such as those disclosed in Hamashima, K. et al. (*Curr. Opin. Chem. Biol.* 2018, 46, 108-114), the contents of which are fully incorporated by reference. For example, UBPs (unnatural base pairs) such as Ds, Px and Pa disclosed in Hamashima, K. et al may be used. It will also be appreciated that XNAs (Xeno nucleic acids) where the base remains the same, but the sugar backbone is modified, may also be used.

In various embodiments, the single-stranded nucleotide sequence comprises a single-stranded deoxynucleotide sequence and/or ribonucleotide sequence. Accordingly, in various embodiments, the method is a method of synthesizing a single-stranded DNA and/or RNA or part thereof. In various embodiments, the ribose/sugar moiety of any one of formulae (I), (II), (III), (IV), (V) and (VI) is a ribose (where the carbon atom at the 2' position comprises an OH group coupled thereto)

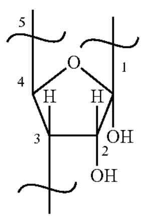

or a deoxyribose (wherein the carbon atom at the 2' position comprises two H coupled thereto)

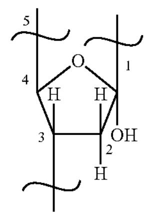

In various embodiments, the initiator nucleotide sequence comprises a single-stranded initiator nucleic acid sequence or part thereof. In various embodiments, the initiator nucleotide sequence comprises one or more nucleotides. In various embodiments, the initiator nucleotide sequence comprises a nucleotide sequence having from about 1 to about 50 nucleotides (e.g. 20-mer nucleotide sequence). The initiator nucleotide sequence may comprise nucleotide sequence such as deoxynucleotide sequence and ribonucleotide sequence. In various embodiments, the initiator nucleotide sequence is a primer sequence. Advantageously, the initiator nucleotide sequence may be a free or a stand-alone nucleotide/nucleic acid sequence that is not hybridized to another nucleotide sequence/nucleic acid sequence or nucleotide template, for e.g. DNA/RNA template. Accordingly, in various embodiments, the method disclosed herein is substantially devoid of a step of hybridizing the initiator nucleotide sequence/nucleic acid sequence to a template.

In various embodiments, the method of synthesizing a single stranded nucleotide sequence disclosed herein is designed for both solid-phase synthesis and solution-phase synthesis.

In various embodiments, step (i) and/or (iii) comprises forming a phosphodiester linkage between the initiator nucleotide sequence and the blocked nucleoside triphosphate. In various embodiments, step (i) and/or (iii) comprises release of a pyrophosphate. There is provided a blocked nucleoside triphosphate for the method of synthesizing a single stranded nucleotide sequence disclosed herein, the blocked nucleoside triphosphate having any one of the general formulae (I), (II), (III), (IV), (V) and (VI) as described herein, wherein n=0 or 1; m=0 to 20; $R^1$, $R^2$, $R^3$, $R^4$, $R^5$ and $R^6$ are each independently selected from hydrogen and alkyl; $R^7$ is selected from hydrogen, alkyl, halogen, $—OR^{19}$, $—NR^{20}R^{21}$ and $—SR^{22}$, wherein $R^{19}$, $R^{20}$, $R^{21}$ and $R^{22}$ are independently selected from hydrogen and alkyl; $R^8$, $R^9$, $R^{10}$, $R^{11}$, $R^{12}$, $R^{13}$, $R^{14}$, $R^{15}$, $R^{16}$, $R^{17}$ and $R^{18}$ are independently selected from hydrogen, alkyl, aryl and heteroaryl; X is a heteroatom selected from O, S and NH; and $Y^1$ and $Y^2$ are each a heteroatom independently selected from O, S and NH, and with the proviso that when n=0, $R^1$ and $R^2$ are both not hydrogen. The blocked nucleoside triphosphate may have one or more features previously described above. Advantageously, embodiments of the reversible terminators/blocked nucleoside trisphosphates disclosed herein work well with and/or well tolerated with polymerases such as TdT. This is despite some of the reversible terminators/blocked nucleoside trisphosphate disclosed herein having bulking/bulky groups (e.g. 4-BOM), which were previously thought to prevent the enzyme to work efficiently. Even more advantageously, removal of the terminating/protecting group in embodiments of the terminators/blocked nucleoside trisphosphate disclosed herein may also be carried out under mild reaction conditions (e.g. mild aqueous conditions), for example, 4-BOM may be removed by a nitroreductase (NTR) enzyme and could lead to a fully enzymatic synthesis of oligonucleotides.

There is also provided a method of preparing a blocked nucleoside triphosphate disclosed herein, the method comprising (i) providing a nucleoside having general formula (VII):

(VII)

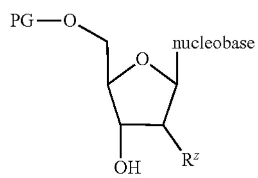

wherein $R^z$ is H or OH and PG is a protecting group;

(ii) introducing a removable terminating group (RT) to the nucleoside having general formula (VII) to obtain a nucleoside having general formula (IX):

(IX)

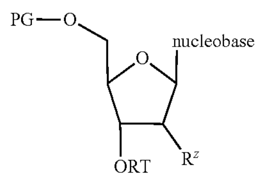

wherein $R^z$ is H or OH and RT is selected from any one of the general formulae (VIIIa), (VIIIb), (VIIIc), (VIIId), (VIIIe) and (VIIIf):

(VIIIa)

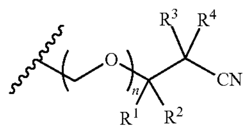

(VIIIb)

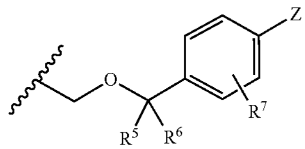

(VIIIc)

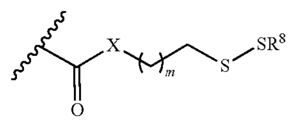

(VIIId)

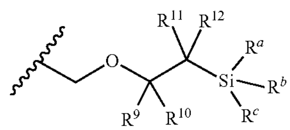

(VIIIe)

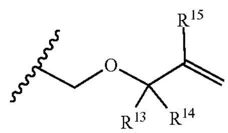

-continued (VIIIf)

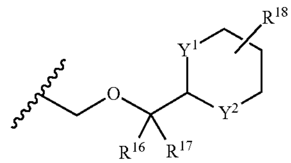

wherein n=0 or 1; m=0 to 20; $R^1$, $R^2$, $R^3$, $R^4$, $R^5$, $R^6$, $R^a$, $R^b$ and $R^c$ are each independently selected from hydrogen, alkyl, alkenyl, aryl and heteroaryl; $R^7$ is selected from hydrogen, alkyl, halogen, —$OR^{19}$, —$NR^{20}R^{21}$ and —$SR^{22}$, wherein $R^{19}$, $R^{20}$, $R^{21}$ and $R^{22}$ are independently selected from hydrogen, alkyl, alkenyl, aryl and heteroaryl; $R^8$, $R^9$, $R^{10}$, $R^{11}$, $R^{12}$, $R^{13}$, $R^{14}$, $R^{15}$, $R^{16}$, $R^{17}$ and $R^{11}$ are independently selected from hydrogen, alkyl, alkenyl, aryl and heteroaryl; X is a heteroatom selected from O, S and NH; $Y^1$ and $Y^2$ are independently selected from S and Se; Z is a chemical moiety that is capable of being released under suitable conditions to trigger removal of the adjacent benzyl linker, and with the proviso that when n=0, $R^1$ and $R^2$ are both not hydrogen; (iii) removing the protecting group (PG) from the nucleoside having general formula (IX) to obtain a nucleoside having general formula (X):

(X)

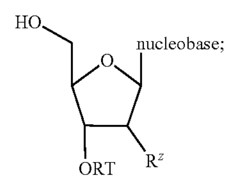

and (iv) converting the hydroxy group in the nucleotide having general formula (X) to triphosphate group to obtain a 3'-O-reversible terminator blocked nucleoside triphosphate.

The protecting group may be selected from the group consisting of dimethoxytrityl (DMT), tert-butyldimethylsilyl (TBS), 9-phenylxanthen-9-yl and 9-(p-tolyl)-xanthen-9-yl, tri-iso-propylsilyloxy-methyl (TOM), trimethylsilyl (TMS) and triisopropylsilyl (TIPS).

In various embodiments, step (ii) of introducing a removable terminating group (RT) to the nucleoside having general formula (VII) comprises introducing RT to the 3'-O position of the nucleoside or 3'-O-protection of the nucleoside. In various embodiments, step (iii) of removing the protecting group (PG) from the nucleoside having general formula (IX) comprises removing PG from the 5'-O position of the nucleoside or 5'-O-deprotection of the nucleoside.

In various embodiments, step (iv) of converting the hydroxy group in the nucleotide having general formula (X) to triphosphate group comprises adding 2-chloro-1,3,2-benzodioxaphosphorin-4-one, followed by pyrophosphate solution, iodine in pyridine/water and finally with water.

EXAMPLES

Figures 1A, 1B:
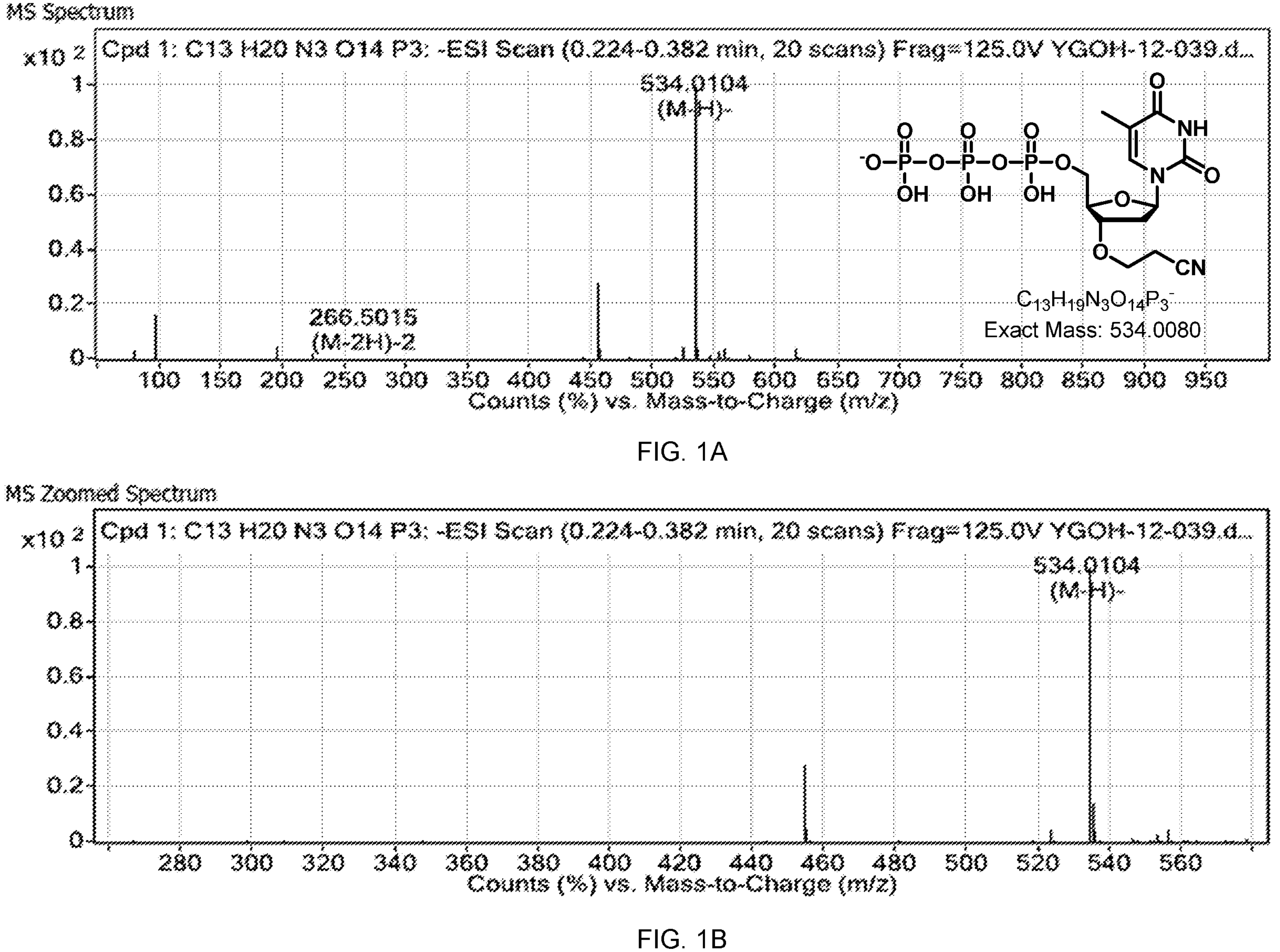
FIG. 1A is a graph showing the overall full mass spectrum of CE-dTTP reversible terminator (1).
FIG. 1B is a graph showing a section of the spectrum zoomed into the m/z range of from about 260 to about 580.

Example embodiments of the disclosure will be better understood and readily apparent to one of ordinary skill in the art from the following examples, tables and if applicable, in conjunction with the figures. It should be appreciated that other modifications related to structural, and chemical changes may be made without deviating from the scope of the invention. Example embodiments are not necessarily mutually exclusive as some may be combined with one or more embodiments to form new example embodiments. The example embodiments should not be construed as limiting the scope of the disclosure.

Example 1: Nucleoside Triphosphate Reversible Terminators

The chemical structures of seven examples of nucleoside triphosphate reversible terminators designed in accordance with various embodiments disclosed herein are shown in Scheme 4 below (see Examples (1) to (7) in the scheme). These nucleoside triphosphate reversible terminators (1) to (7) are blocked at the 3'-O position respectively by removable terminating groups (RT) namely 2-cyanoethyl ether (herein termed "CE"), 2-(tert-butyldisulfanyl)ethyl carbonate or disulfide carbonate (herein termed "DT"), 2-(trimethylsilyl)ethoxymethyl (herein termed "SEM"), (allyloxy)methyl (herein termed "AL" or "ALM"), 4-nitrobenzyloxymethyl (herein termed "PNBA"), dithianemethyl acetal (herein termed "DMA") and (2-cyanoethoxy)methyl (herein termed "CEM").

Scheme 4. Seven examples of nucleoside triphospate reversible terminators designed in accordance with various embodiments disclosed herein, shown alongside 7 comparative examples.

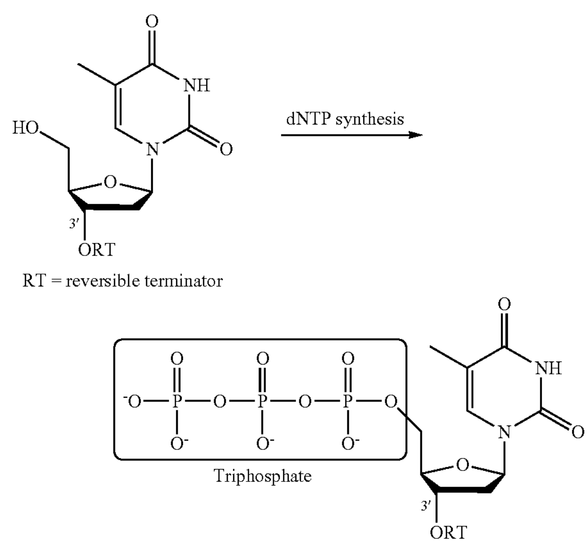

RT = reversible terminator

Triphosphate 14 examples

Reversible Terminators Examples (1) to (7)

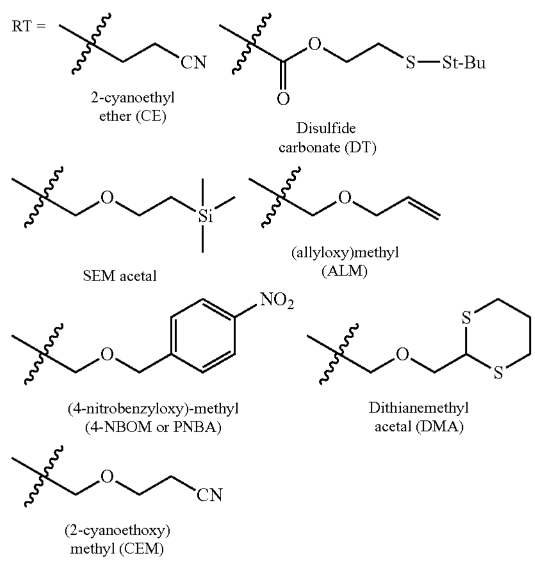

RT =

2-cyanoethyl ether (CE)

Disulfide carbonate (DT)

SEM acetal (allyloxy)methyl (ALM)

(4-nitrobenzyloxy)-methyl (4-NBOM or PNBA)

Dithianemethyl acetal (DMA)

(2-cyanoethoxy) methyl (CEM)

-continued

Reversible Terminators (Comparative Examples)

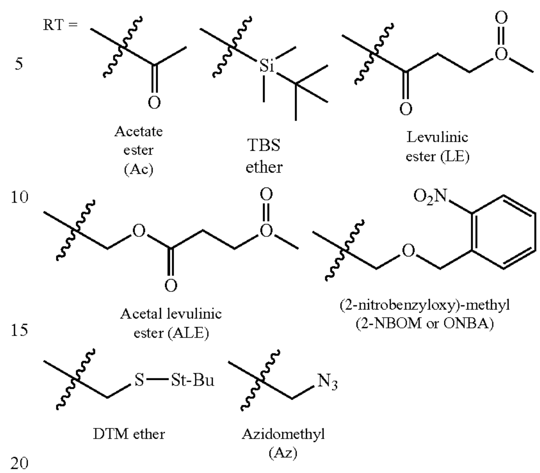

RT =

Acetate ester (Ac)

TBS ether

Levulinic ester (LE)

Acetal levulinic ester (ALE)

(2-nitrobenzyloxy)-methyl (2-NBOM or ONBA)

DTM ether

Azidomethyl (Az)

For comparative purposes, a total of seven other nucleoside triphosphate reversible terminators that are blocked at the 3'-position was also synthesized and analysed alongside Examples (1) to (7). The comparative examples are blocked at the 3'-O position respectively by acetate ester (herein termed "Ac"), tert-butyldimethylsilyl ether (herein termed "TBS"), levulinic ester (herein termed "LE"), acetal levulinyl ester (herein termed "ALE"), 2-nitrobenzyloxy-methyl (herein termed "ONBA"), disulfide methyl ether (herein termed "DTM") and azidomethyl (herein termed "Az").

Advantageously, the nucleoside triphosphate reversible terminators designed in accordance with various embodiments disclosed herein are recognized by template independent polymerases and cleavage of the removable terminating/blocking groups can be performed under a wide range of reaction conditions. The cleavage of the removable terminating/blocking groups enables a process elongating the nucleic acid sequence through a series of iteration cycles, thereby showing that these nucleoside triphosphate reversible terminators are successful in enzymatic synthesis of nucleic acids.

In the following examples, the results demonstrated the utility of these nucleoside triphosphate reversible terminators in single base addition to single-stranded nucleotide sequence catalysed by commercial/engineered template-independent terminal deoxynucleotidyl transferase (TdT) enzyme as the polymerase (Scheme 5).

Scheme 5. Seven examples of nucleoside triphosphate reversible terminators designed in accordance with various embodiments disclosed herein that were succesfully used in enzymatic synthesis of oligonucleotides

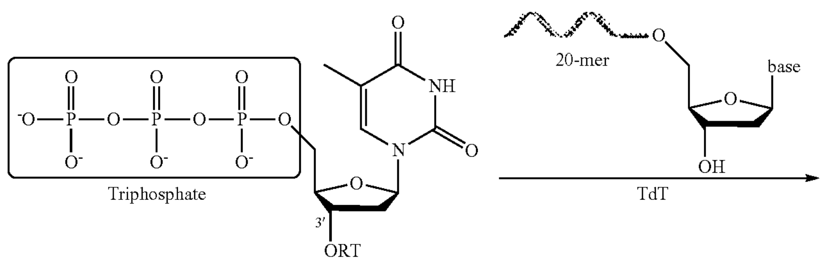

Triphosphate

-continued

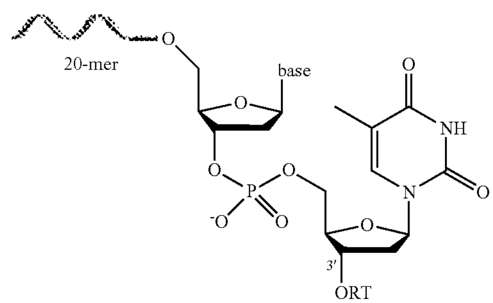

Reversible Terminators Examples (1) to (7)

RT =

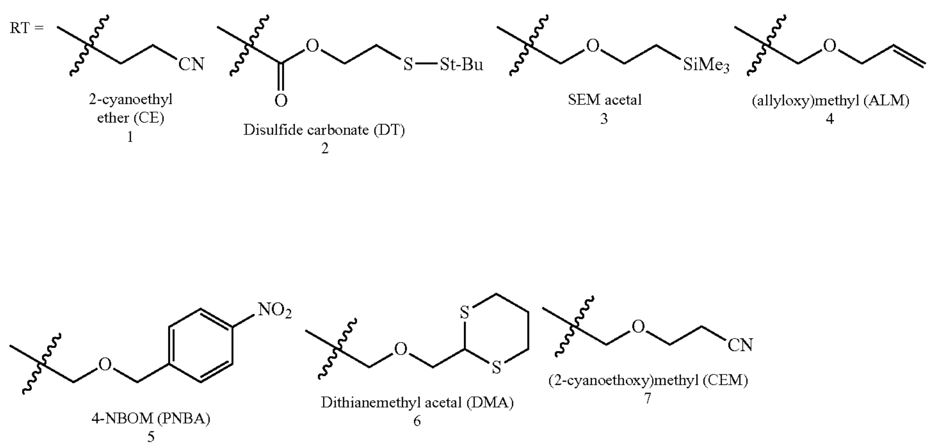

2-cyanoethyl ether (CE)
1

Disulfide carbonate (DT)
2

SEM acetal
3

(allyloxy)methyl (ALM)
4

4-NBOM (PNBA)
5

Dithianemethyl acetal (DMA)
6

(2-cyanoethoxy)methyl (CEM)
7

On the other hand, synthesis of single-stranded nucleotide sequence was not successful or inferior with the seven comparative examples (as listed in Scheme 4) under mild reaction conditions (e.g. substantially aqueous conditions).

Accordingly, it will be appreciated by a person skilled in the art that the design of the nucleoside triphosphate reversible terminators in accordance with various embodiments disclosed herein requires careful architecture to work. Such designs are not easily conceived and are not merely obvious modification of existing protecting groups for the purpose of synthesizing single-stranded nucleotide sequence. It will also be appreciated that it is not easy to be able to arrive at alternative novel protecting/terminating groups that work with polymerases such as TdT under mild reaction conditions (e.g. substantially aqueous conditions).

Example 2: Synthesis of Nucleoside Triphosphate Reversible Terminators

The respective synthesis procedures for 2-cyanoethyl ether (CE)-dTTP reversible terminator (1), disulfide carbonate (DT)-dTTP reversible terminator (2), 2-(trimethylsilyl) ethoxymethyl (SEM)-dTTP reversible terminator (3), (allyloxy)methyl (ALM)-dTTP reversible terminator (4), 4-nitrobenzyloxy-methyl (PNBA)-dTTP reversible terminator (5), dithianemethyl acetal (DMA)-dTTP reversible terminator (6) and (2-cyanoethoxy)methyl (CEM)-dTTP reversible terminator (7) are provided in detail below.

Materials and Methods

All reactions were carried out under an argon atmosphere with dry solvents under anhydrous conditions. Water, ethyl acetate (EtOAc), methylene chloride ($CH_2Cl_2$), and petroleum ether were purchased at the highest commercial quality and used without further purification. Reagents were purchased at the highest commercial quality and used without further purification. Yields refer to chromatographically and spectroscopically ($^1H$ NMR) homogeneous materials. Reactions were monitored by thin-layer chromatography (TLC) carried out on 0.25 mm E. Merck silica gel plates (60F-254) using UV light as visualizing agent and a solution of potassium permanganate and heat as developing agents. E. Merck silica gel (60, particle size 0.040-0.063 mm) was used for flash-column chromatography. Dioxane and dimethylformamide (DMF) were freshly taken from the solvent purification system (SPS) machine. Pyridine was refluxed over calcium hydride ($CaH_2$) for 2 h before being distilled at atmospheric pressure. Tributylamine was distilled under vacuum over $CaH_2$ at 120° C. (without molecular sieves). NMR spectra were recorded on a Bruker DRX-400 (400 MHz) instrument and calibrated using residual non deuterated solvent as an internal reference. IR spectra were recorded on a Perkin-Elmer Spectrum One FTIR spectrometer with diamond ATR accessory. High-resolution mass spectra (HRMS) were recorded on an Agilent ESI TOF (time-of-flight) mass spectrometer at 3.5 kV emitter voltage.

Synthesis of 2-Cyanoethyl Ether (CE)-dTTP Reversible Terminator (1)

Scheme 6 shows the reaction scheme for the synthesis of CE-dTTP nucleoside triphosphate reversible terminator (1).

Scheme 6. Synthesis of CE-dTTP reversible terminator (1)

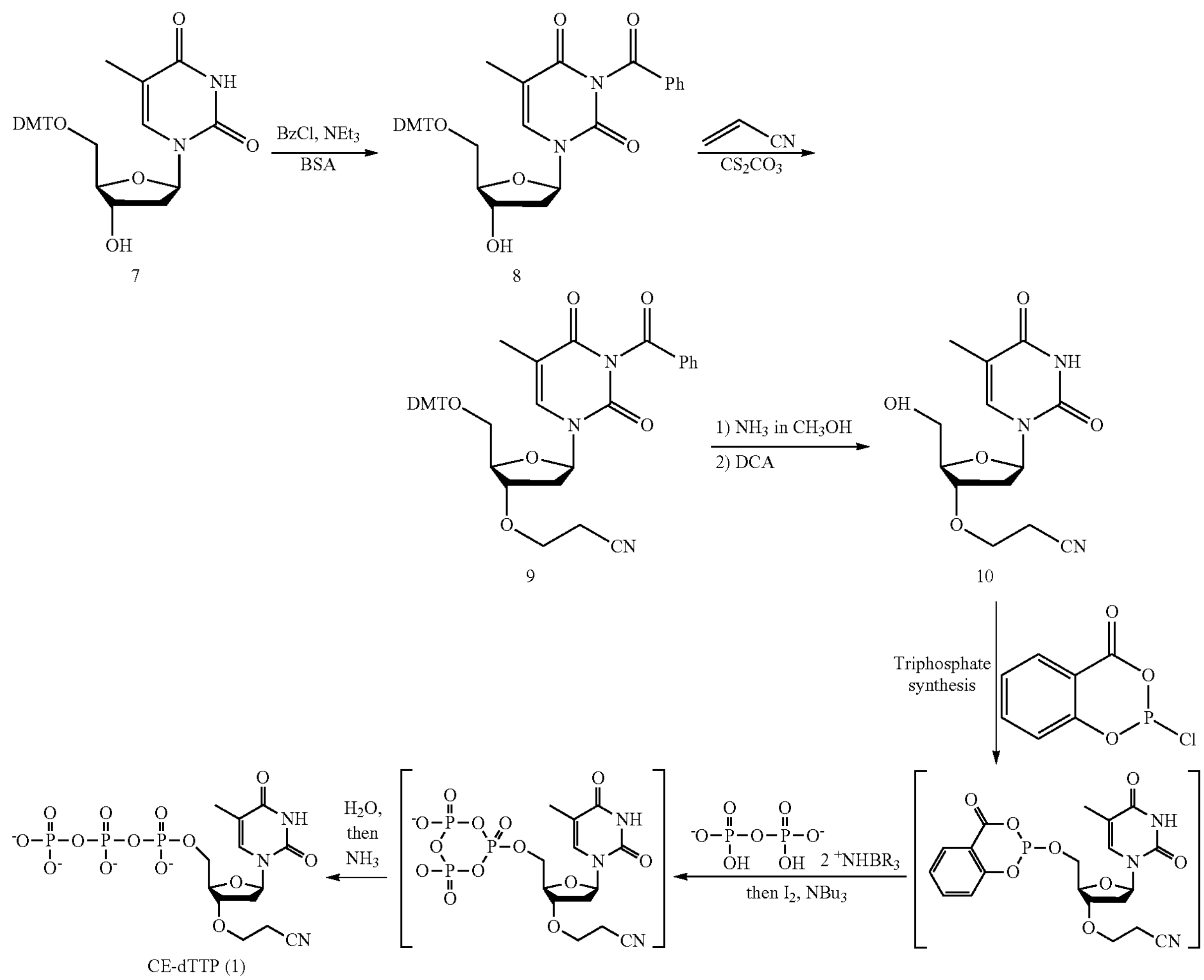

7

8

9

10

CE-dTTP (1)

5'-O-dimethoxytrityl-N3-benzoylthymidine (8)

To a solution of 5'-O-(dimethoxytrityl)thymidine (7) (506 mg, 0.93 mmol) in $CH_3CN$ (15 mL) was added N,O-Bis (trimethylsilyl)acetamide (BSA, 456 µL, 1.86 mmol) and the solution was heated at 90° C. for 1 h. After cooling down to 25° C., triethylamine (258 µL, 1.86 mmol) and benzoyl chloride (130 µL, 1.30 mmol) were added and the medium was stirred for 16 h before tetra-n-butylammonium fluoride (TBAF, 1 M in THF, 2.8 mL, 2.8 mmol) was added and stirring was continued for 1 h. After concentration under vacuum, the residue was dissolved in ethyl acetate (AcOEt) and washed with sat. $NaHCO_3$ and water. The organic layer was dried over $Na_2SO_4$, concentrated and the crude product was purified by silica gel chromatography (5%, 10% then 20% of AcOEt in $CH_2Cl_2$) to afford 5'-O-dimethoxytrityl-N3-benzoylthymidine (8) as a white solid (513 mg, 85%).

5'-O-dimethoxytrityl-3'-O-(2-cyanoethyl)-$N_3$-benzoylthymidine (9)

To a suspension of 5'-O-dimethoxytrityl-N3-benzoylthymidine (8) (500 mg, 0.77 mmol) in t-BuOH (7 mL) were added acrylonitrile (1 mL, 15.2 mmol) and $Cs_2CO_3$ (300 mg, 0.92 mmol). After 16 h at 25° C., the medium was filtered over Celite®, the filtrate was concentrated and $^1H$ and $^{13}C$ NMR NMR spectra showed pure 5'-O-dimethoxytrityl-3'-O-(2-cyanoethyl)-$N_3$-benzoylthymidine (9) which was directly used in the next step.

3'-O-(2-cyanoethyl)-thymidine (10)

Crude 5'-O-dimethoxytrityl-3'-O-(2-cyanoethyl)-N3-benzoylthymidine (9) was suspended in ammonia (7 M in MeOH, 8 mL) and deionized water (2 mL). The initial heterogeneous solution homogenized over time and after 3 h the medium was concentrated under vacuum. The residue was dissolved in $CH_2Cl_2$, washed with deionized water and the organic layer was concentrated before $CH_2Cl_2$ (10 mL) and dichloroacetic acid (600 µL, 7.26 mmol) were added. After 15 min, the deep orange solution was concentrated and the residue was purified by silica gel chromatography ($CH_2Cl_2$/AcOEt 1/1, then $CH_2Cl_2$/$CH_3OH$ 95/5) to provide 3'-O-(2-cyanoethyl)-thymidine (10) as a white foam (141 mg, 62% over three steps).

2-cyanoethyl ether (CE)-dTTP nucleoside precursor (10) was then converted to nucleoside triphosphate (1) via Ludwig-Eckstein triphosphate synthesis (Scheme 10).

The CE-dTTP reversible terminator (1) was characterized by HRMS. HRMS (ESI−): m/z calcd for $C_{13}H_{19}N_3O_{14}P_3$ $[M-H]^-$ 534.0080, found 534.0104. The mass spectrum of (1) is shown in FIG. 1.

Synthesis of Disulfide Carbonate (DT)-dTTP Reversible Terminator (2)

Scheme 7 shows the reaction scheme for the synthesis of DT-dTTP nucleoside precursor (14).

Scheme 7. Synthesis of DT-dTTP nucleoside precursor (14)

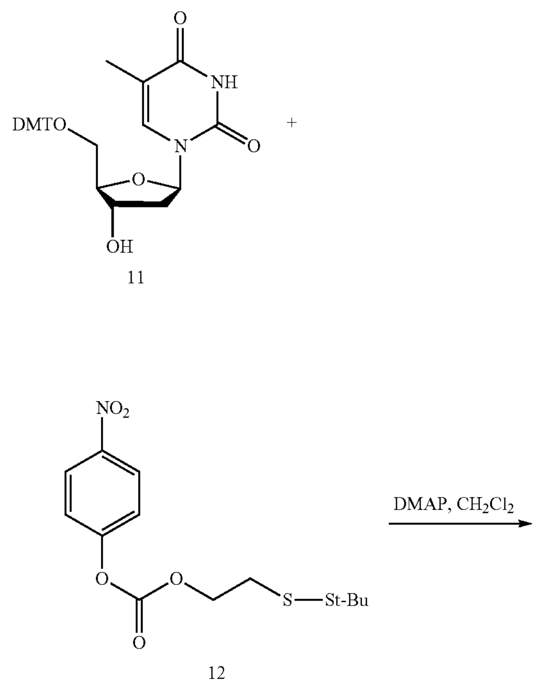

11

12

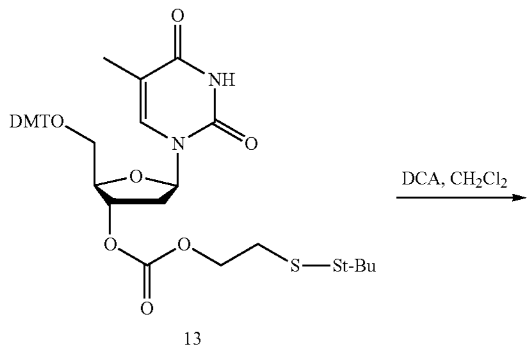

13

-continued

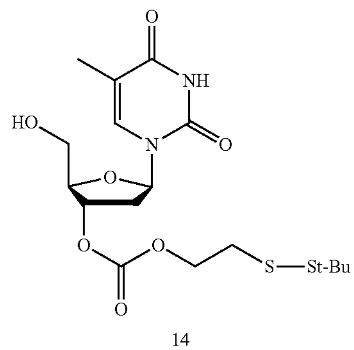

14

Carbonate (13):

To a solution of 2-(tert-butyldisulfanyl)ethyl-(4-nitrophenyl)-carbonate (12) (156 mg, 0.47 mmol) in $CH_2Cl_2$ (9 mL) were added 5'-O-(4,4'-Dimethoxytrityl)thymidine (11) (284 mg, 0.52 mmol) and DMAP (57 mg, 0.47 mmol) at 25° C. After 16 h, washings with sat. $NaHCO_3$ and water, most of the yellow color (i.e., nitrophenol) went in the aq. layer. Purification on silica (petroleum ether/ethyl acetate: 7/3 then 1/1) provided 319 mg of the desired carbonate (92% yield).

Figure 2A:
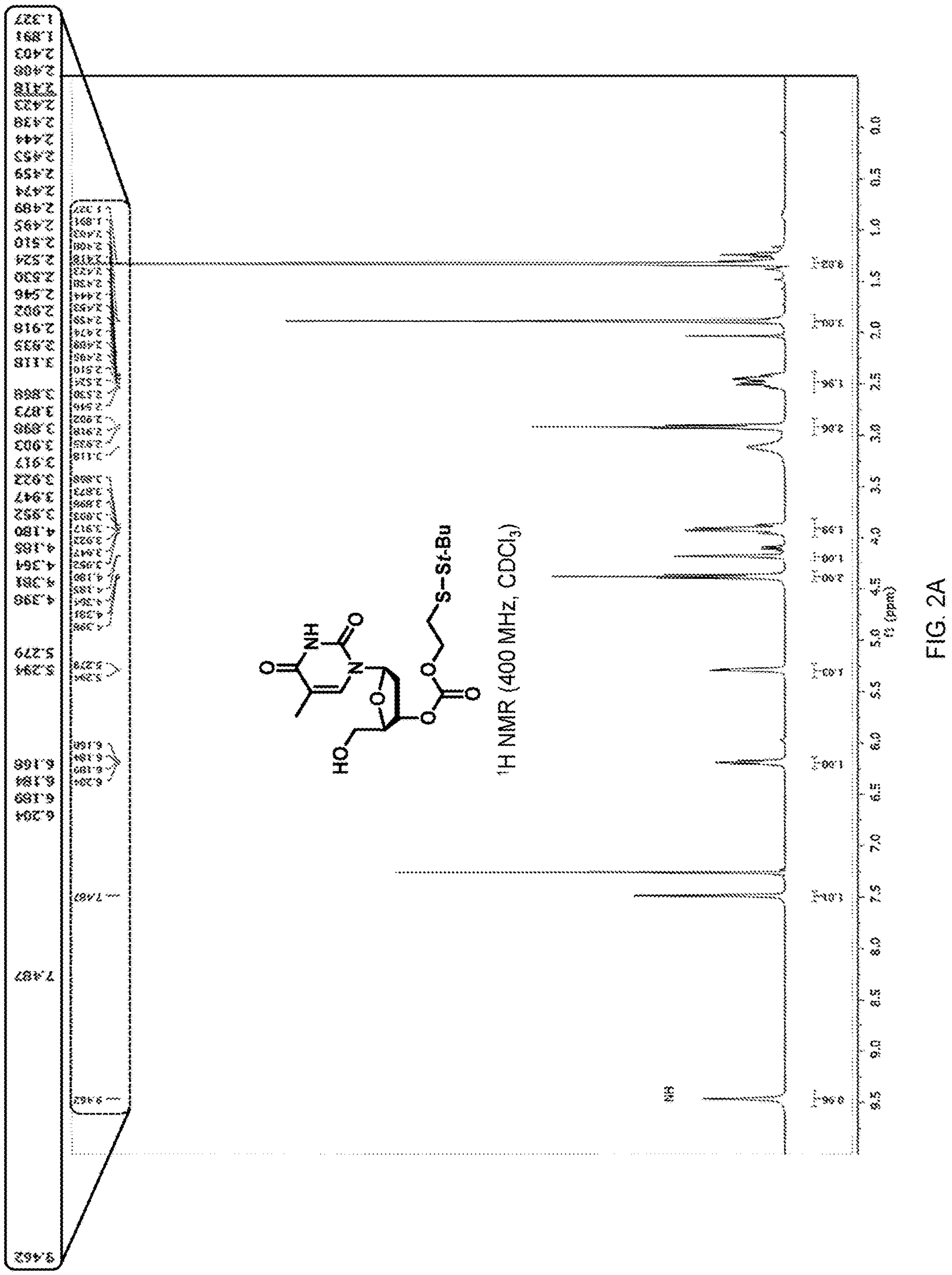
FIG. 2A is a graph showing $^{1}H$ NMR spectrum of DT-dTTP nucleoside precursor (14).
Figure 2B:
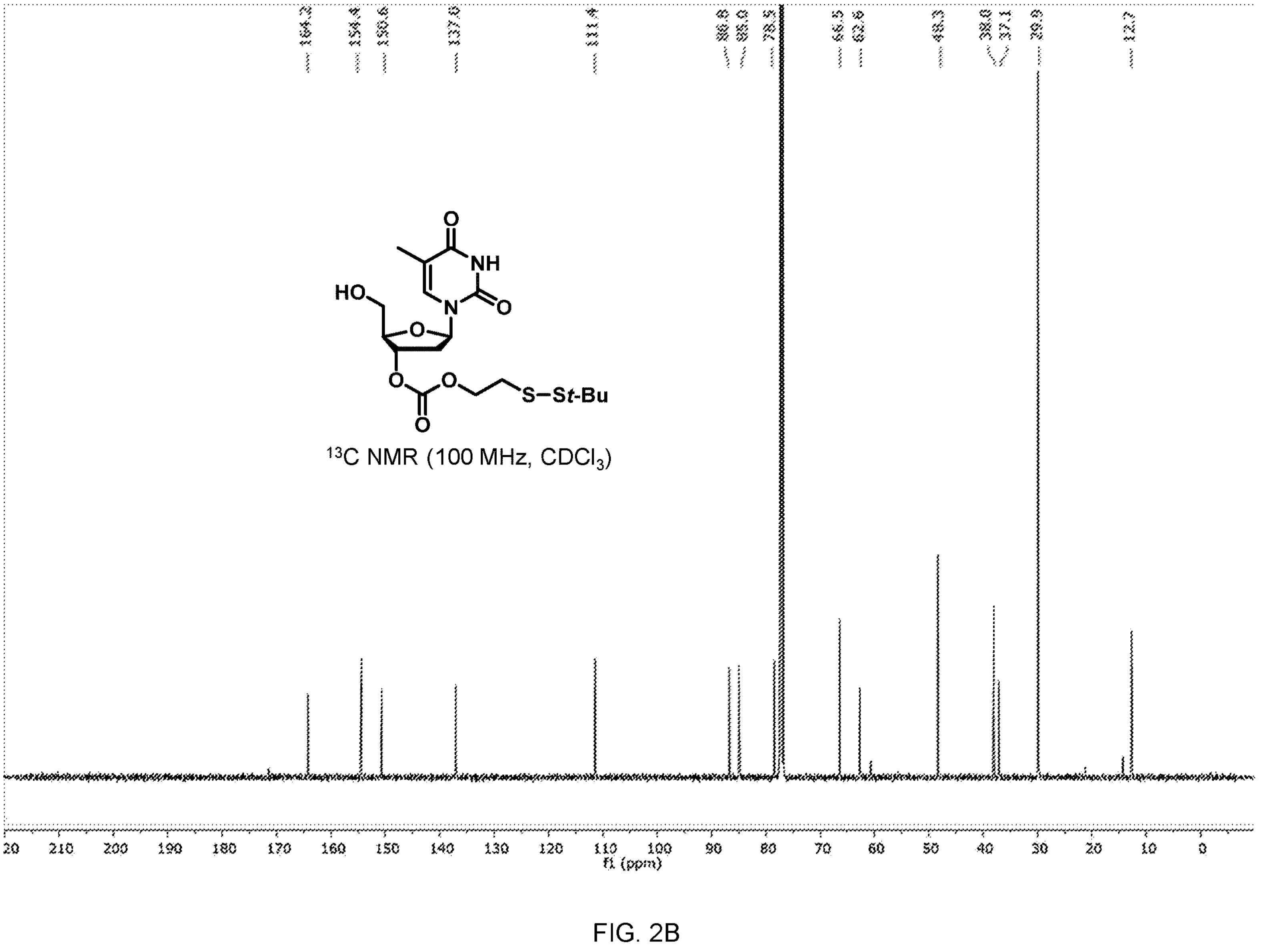
FIG. 2B is a graph showing $^{13}C$ NMR spectrum of DT-dTTP nucleoside precursor (14).

Carbonate (14):

To a solution of the above carbonate (401 mg, 0.54 mmol) in $CH_2Cl_2$ (12 mL) was added DCA (250 μL, 2.8 mmol) and after 1 h, the TLC showed a clean DMT deprotection. After 2.5 h, the reaction mixture was concentrated and loaded on silica gel for purification (petroleum ether/ethyl acetate: 7/3, 1/1 then 3/7) to give 199 mg of a white foam (85% yield). The $^1H$ NMR and $^{13}C$ NMR spectra of (14) are provided in FIGS. 2A and 2B respectively.

The disulfide carbonate (DT)-dTTP nucleoside precursor (14) was then converted to nucleoside triphosphate (2) via Ludwig-Eckstein triphosphate synthesis (Scheme 10).

Figures 2C, 2D:
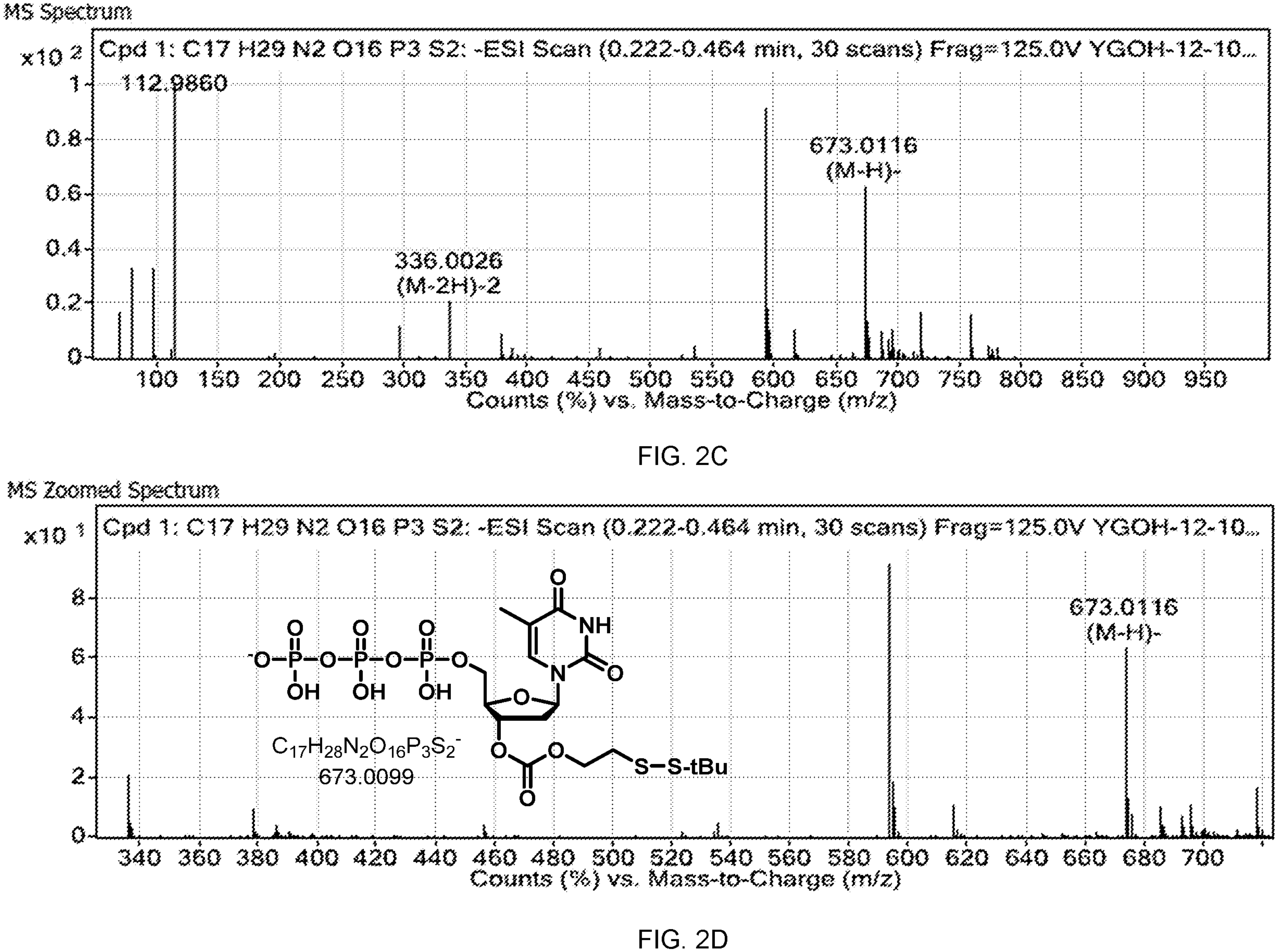
FIG. 2C is a graph showing the overall full mass spectrum of DT-dTTP reversible terminator (2).
FIG. 2D is a graph showing a section of the spectrum zoomed into the m/z range of from about 330 to about 720.

The DT-dTTP reversible terminator (2) was characterized by HRMS, the mass spectrum of (2) is shown in FIGS. 2C and 2D. HRMS (ESI−): m/z calcd for $C_{17}H_{28}N_2O_{16}P_3S_2$ $[M-H]^-$ 673.0099, found 673.0116.

Synthesis of 2-(Trimethylsilyl)Ethoxymethyl (SEM)-dTTP Reversible Terminator (3)

Scheme 8 shows the reaction scheme for the synthesis of SEM-dTTP nucleoside precursor (17).

Scheme 8. Synthesis of SEM-dTTP nucleoside precursor (17)

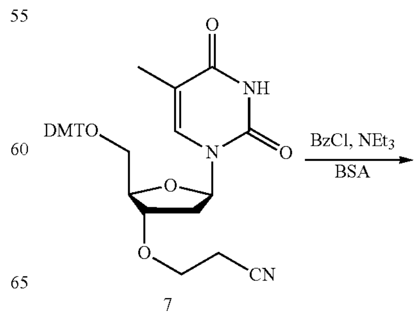

7

-continued

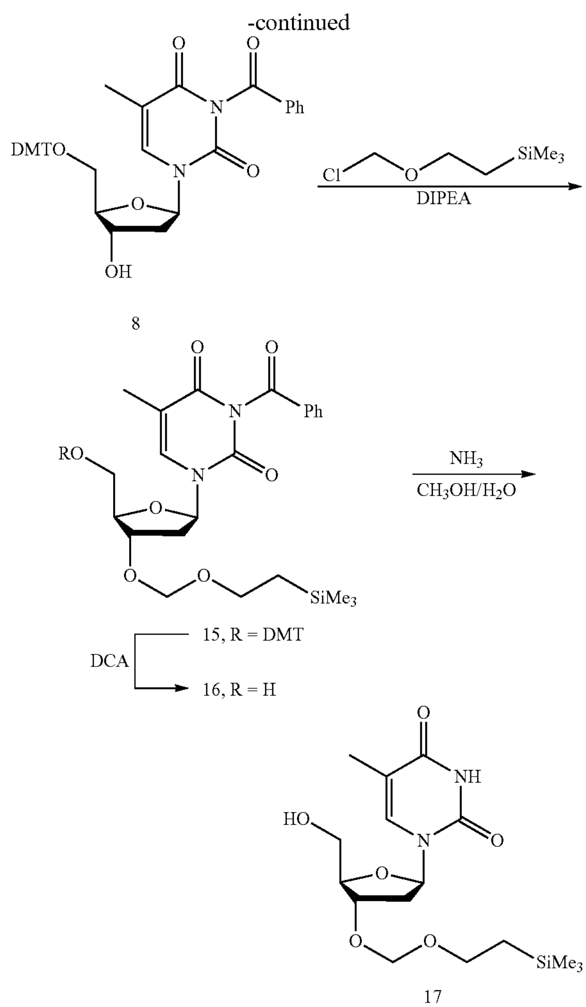

8

17

5'-O-dimethoxytrityl-N3-benzoylthymidine (8)

To a solution of 5'-O-(dimethoxytrityl)thymidine (7) (506 mg, 0.93 mmol) in $CH_3CN$ (15 mL) was added N,O-Bis (trimethylsilyl)acetamide (BSA, 456 μL, 1.86 mmol) and the solution was heated at 90° C. for 1 h. After cooling down to 25° C., triethylamine (258 μL, 1.86 mmol) and benzoyl chloride (130 μL, 1.30 mmol) were added and the medium was stirred for 16 h before tetra-n-butylammonium fluoride (TBAF, 1 M in THF, 2.8 mL, 2.8 mmol) was added and stirring was continued for 1 h. After concentration under vacuum, the residue was dissolved in ethyl acetate (AcOEt) and washed with sat. $NaHCO_3$ and water. The organic layer was dried over $Na_2SO_4$, concentrated and the crude product was purified by silica gel chromatography (5%, 10% then 20% of AcOEt in $CH_2Cl_2$) to afford 5'-O-dimethoxytrityl-N3-benzoylthymidine (8) as a white solid (513 mg, 85%).

Acetal (16):

To a solution of 5'-O-dimethoxytrityl-N3-benzoylthymidine (8) (200 mg, 0.308 mmol) in $CH_2Cl_2$ (3 mL) were added N,N-Diisopropylethylamine (DIPEA, 161 μL, 0.924 mmol) and 2-(Trimethylsilyl)ethoxymethyl chloride (72 μL, 0.616 mmol). After 16 h at 25° C., more 2-(trimethylsilyl) ethoxymethyl chloride (36 μL, 0.308 mmol) was added and the medium was stirred further for 24 h. The solution was then diluted with $CH_2Cl_2$, washed with aq. $NaHCO_3$ (sat.) and the organic layer was dried over $Na_2SO_4$. Half of the $CH_2Cl_2$ was removed under reduced pressure and to the resulting solution of acetal (15) was added dichloroacetic acid (DCA, 203 μL, 2.47 mmol). After 1 h at 25° C., the medium was concentrated and the residue was purified by silica gel chromatography (gradient $CH_2Cl_2$/AcOEt 97.5/2.5 to 80/20) to provide acetal (16) as a white foam (83 mg, 57% over two steps).

Acetal (17):

To a suspension of acetal (16) (83 mg, 0.174 mmol) in $CH_3OH$ (1.93 mL) was added ammonia (7M in $CH_3OH$, 2 mL, 14 mmol) and the medium was stirred at 25° C. for 16 h. The volatiles were evaporated under vacuum and the residue was purified by silica gel chromatography (gradient $CH_2Cl_2/CH_3OH$ 100/0 to 97.5/2.5) to provide acetal (17) as a colorless oil (48 mg, 74%).

The 2-(trimethylsilyl)ethoxymethyl (SEM)-dTTP nucleoside precursor (17) was then converted to nucleoside triphosphate (3) via Ludwig-Eckstein triphosphate synthesis (Scheme 10).

Synthesis of (Allyloxy)Methyl (ALM)-dTTP Reversible Terminator (4), 4-Nitrobenzyloxy-Methyl (PNBA)-dTTP Reversible Terminator (5), Dithianemethyl Acetal (DMA)-dTTP Reversible Terminator (6) and (2-Cyanoethoxy)Methyl (CEM)-dTTP Reversible Terminator (7)

Scheme 9 shows the reaction scheme for the synthesis of ALM-dTTP nucleoside precursor (22a), PNBA-dTTP nucleoside precursor (22b), DMA-dTTP nucleoside precursor (22c) and CEM-dTTP nucleoside precursor (22d) respectively.

Scheme 9. Synthesis of ALM-dTTP, PNBA, PNBA-dTTP, DMA-dTTP, and CEM-dTTP nucleoside precursors (22a-d)

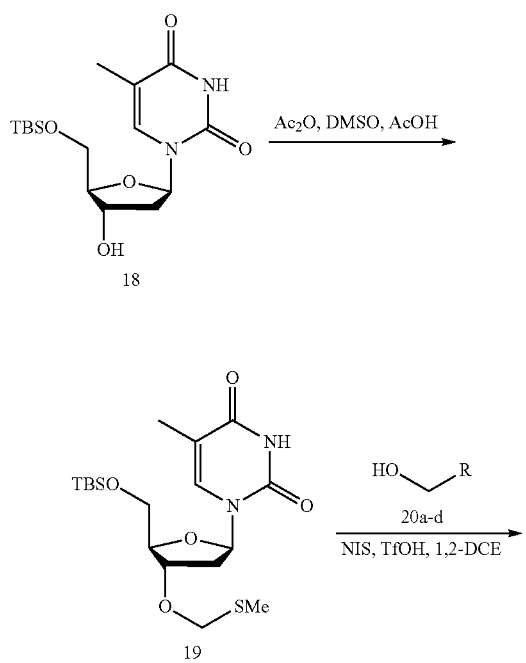

18

19

-continued

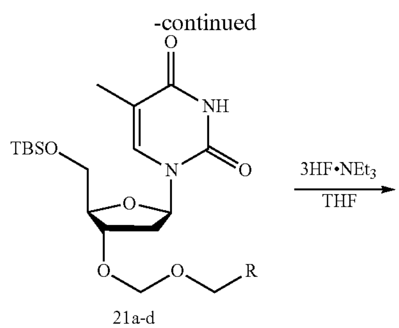

21a-d

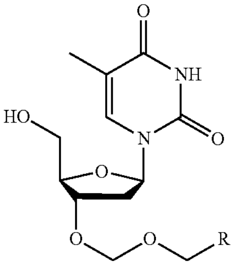

22a-d

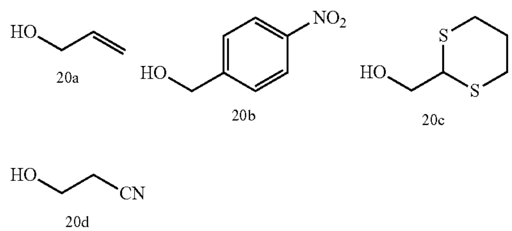

20a

20b

20c

20d

3'-O-(Methylthiomethyl)-5'-O-(tert-butyldimethylsilyl)thymidine (19)

To a solution of 5'-O-(tertbutyldimethylsilyl) thymidine (18) (4.0 g, 11.2 mmol) in DMSO (20 mL) were added AcOH (10 mL) and $Ac_2O$ (30 mL) at 25° C. After 48 h, sat. $NaHCO_3$ and ethyl acetate were added and the aqueous layer was extracted with ethyl acetate. The combined organic layers were washed with water, dried over $Na_2SO_4$ and after filtration and concentration, the residue was purified on silica gel (petroleum ether/ethyl acetate 9/1, 7/3 then 65/35), giving 4.63 g of thioether (19) at a colorless gum (99%).

Procedure for the Synthesis of Acetals (21a-d):

To a suspension of dried thioether (19) (1 eq.) and freshly activated 4 Å molecular sieve (~0.5-1 g/mmol of substrate) at 0° C. were added alcohol 20a, 20b, 20c or 20d (1.1-1.6 eq.), NIS (1.1 eq.) and trifluoromethanesulfonic acid (0.05-0.1 eq.) and the solution was stirred for 1 h. The medium was quenched with 1 M sodium sulfite followed by slow addition of $NaHCO_3$ and the organic layer was dried over $Na_2SO_4$. After filtration and concentration under vacuum, the residue was purified on silica gel (petroleum ether/ethyl acetate) to provide the corresponding acetal 21a, 21b, 21c, 21d (63%, 42%, 10%, and 38%, respectively) and 22d (20%).

Procedure for the Synthesis of Acetals (22a-d):

To a solution of acetals 21a, 21b, 21c or 21d in THF (0.05 M) was added triethylamine trihydrofluoride (5 eq.) and the resulting solution was stirred in a plastic container for 4 days. The medium was then concentrated under vacuum and the residue was purified on silica gel ($CH_2Cl_2/CH_3OH$) to provide the corresponding acetal 22a, 22b, 22c and 22d (89%, 65%, 68%, and 72%, respectively).

The (allyloxy)methyl (ALM)-dTTP nucleoside precursor (22a), 4-nitrobenzyloxy-methyl (PNBA)-dTTP nucleoside precursor (22b), dithianemethyl acetal (DMA)-dTTP nucleoside precursor (22c) and (2-cyanoethoxy)methyl (CEM)-dTTP nucleoside precursor (22d) were then respectively converted to nucleoside triphosphates (4), (5), (6) and (7) via Ludwig-Eckstein triphosphate synthesis (Scheme 10).

Figures 3A, 3B:
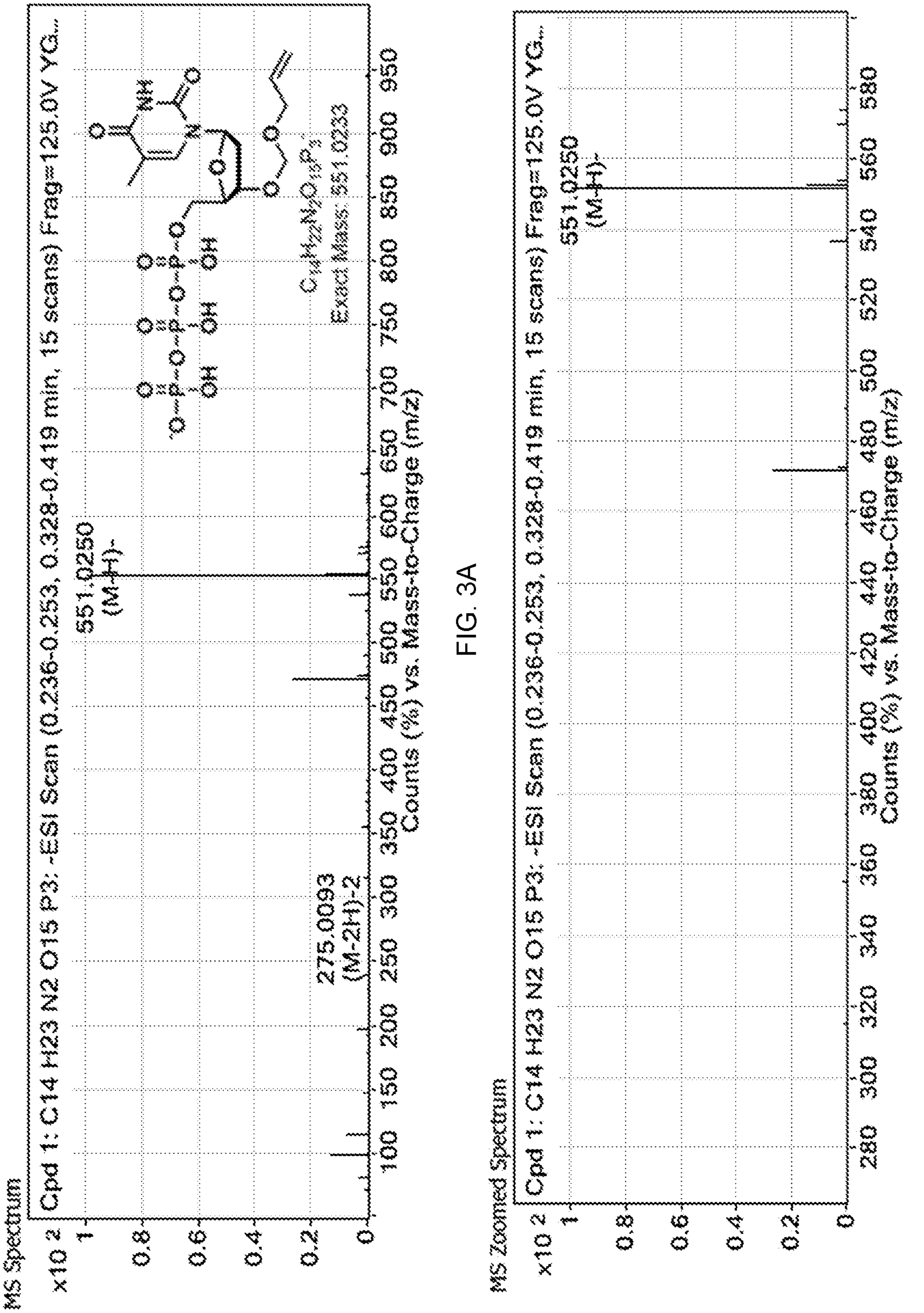
FIG. 3A is a graph showing the overall full mass spectrum of AL/ALM-dTTP reversible terminator (4).
FIG. 3B is a graph showing a section of the spectrum zoomed into the m/z range of from about 260 to about 600.

The ALM-dTTP reversible terminator (4) was characterized by HRMS. HRMS (ESI−): m/z calcd for $C_{14}H_{22}N2015P_3$ $[M-H]^-$ 551.0233, found 551.0250. The mass spectrum of (4) is shown in FIG. 3.

Figures 4A, 4B:
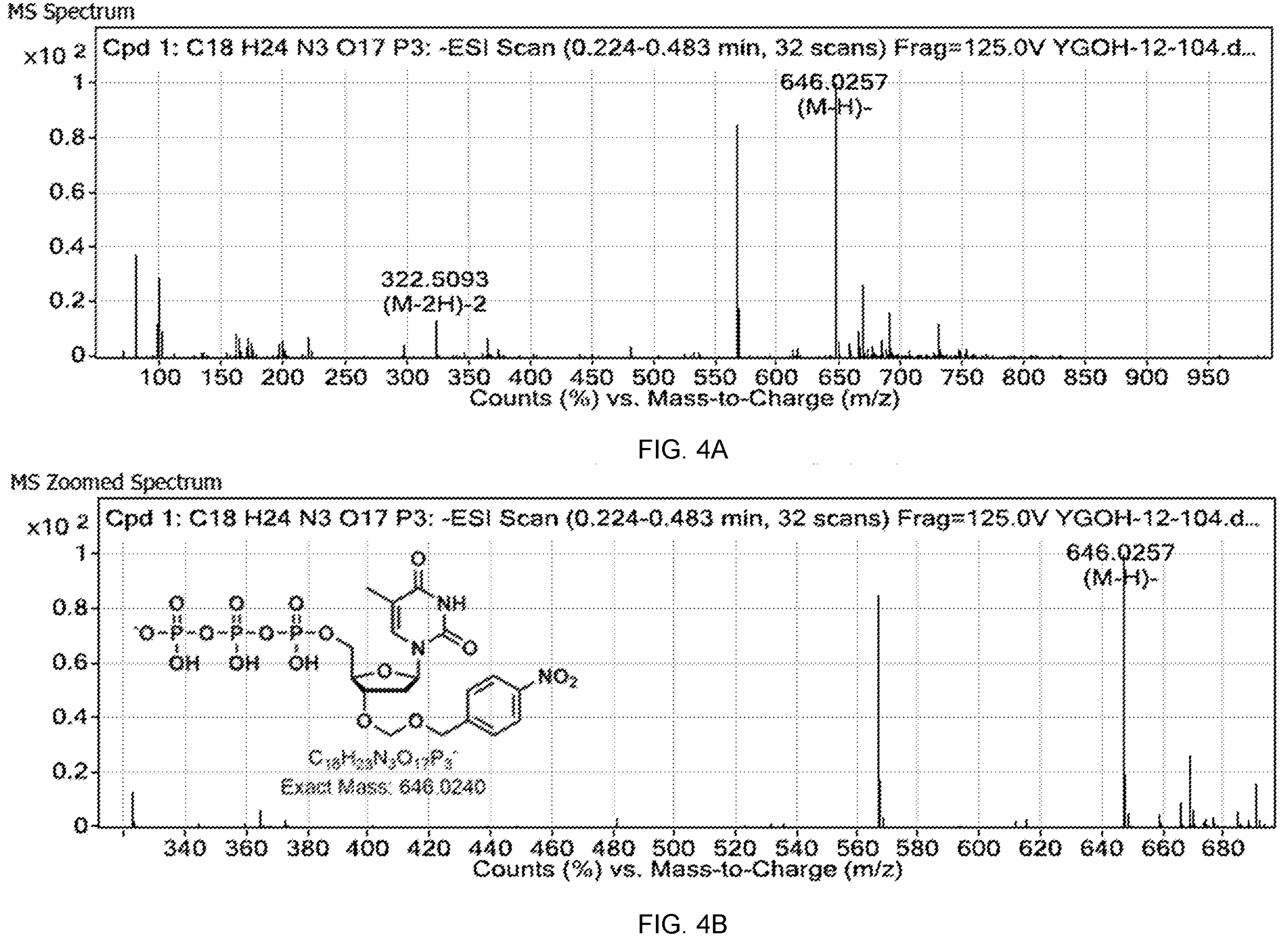
FIG. 4A is a graph showing the overall full mass spectrum of PNBA-dTTP reversible terminator (5).
FIG. 4B is a graph showing a section of the spectrum zoomed into the m/z range of from about 320 to about 700.

The PNBA-dTTP reversible terminator (5) was characterized by HRMS. HRMS (ESI−): m/z calcd for $C_{18}H_{23}N3017P_3$ $[M-H]^-$ 646.0240, found 646.0257. The mass spectrum of (5) is shown in FIG. 4.

Synthesis of Nucleoside Triphosphate Reversible Terminators (1-7) Respectively from Nucleosides (10), (14), (17) and (22a-d)

Scheme 10 shows the general reaction scheme for the synthesis of nucleoside triphosphates from their corresponding nucleosides/precursors. The nucleoside triphosphate reversible terminators were prepared from the 5'-hydroxy precursors using a method developed by Ludwig and Ecktein (*J. Org. Chem.* 1989, 54, 631-635) and modified by Hollenstein, M. et al. (*J. Vis. Exp.* 2014, 86, e51385), the contents of which are fully incorporated by reference.

Scheme 10. Synthesis of nucleoside triphosphates from their corresponding precursors via Ludwig-Ecktein triphosphate synthesis

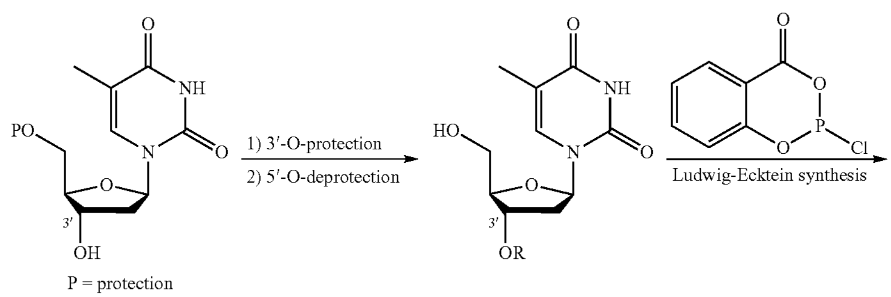

-continued

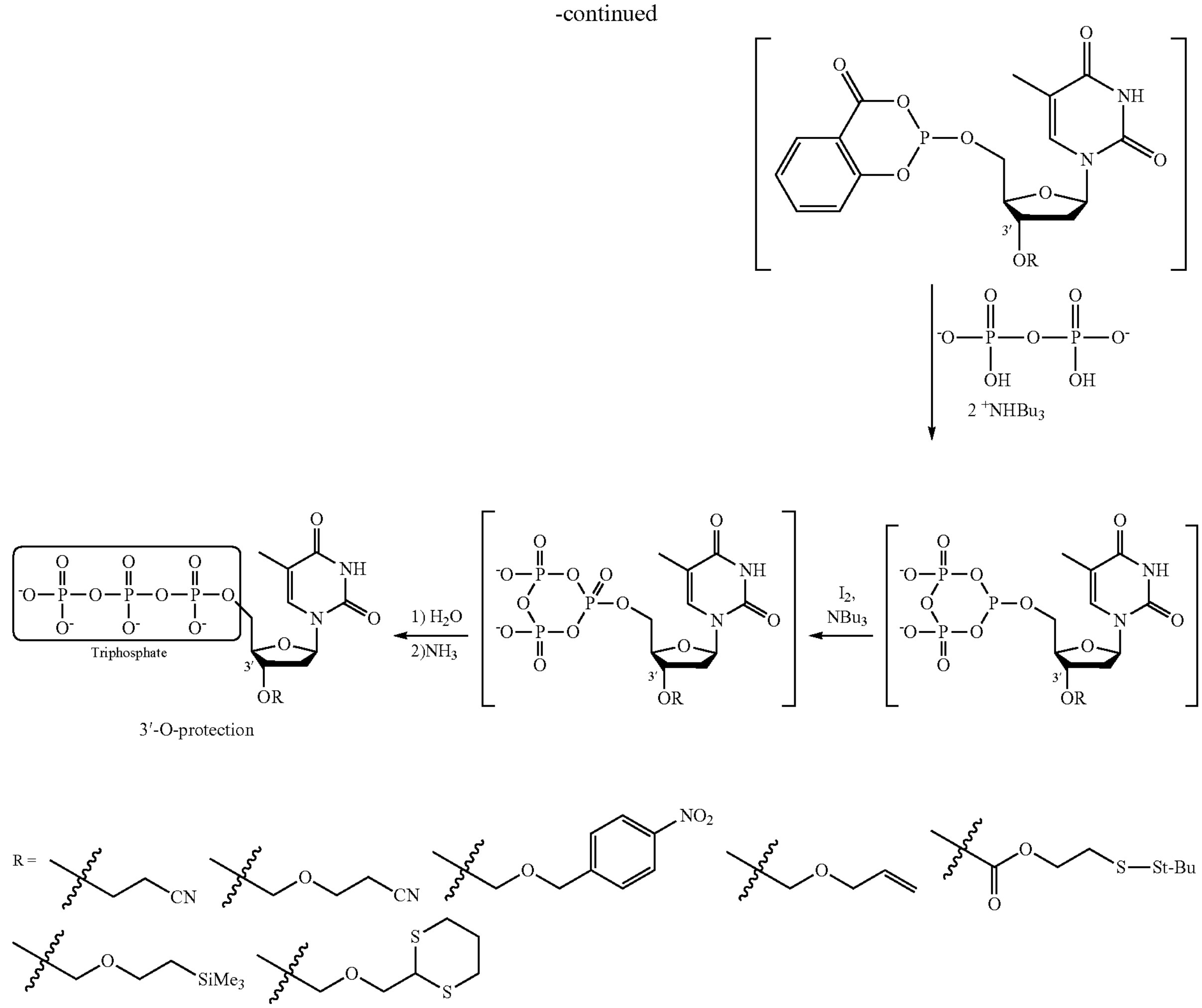

Nucleoside (10), (14), (17) or (22a-d) (dried under vacuum for 16 h, ~0.2 mmol) was dissolved in a minimum of dry pyridine (0.4 mL). Then, dry dioxane (0.8 mL) and 2-chloro-1,3,2-benzodioxaphosphorin-4-one (~0.24 mmol) were added and the reaction was stirred at 25° C. for 45 min. A pyrophosphate solution was prepared by mixing tributylammonium pyrophosphate (dried under vacuum for 16 h, ~0.26 mmol) in dry DMF (0.35 mL) with freshly distilled tributylamine (~0.50 mmol). The cloudy and heterogenous solution obtained was added to the reaction mixture (a white precipitate appears but quickly disappeared to a yellow solution) and stirred at 25° C. for 45 min. A solution of iodine (~0.32 mmol) in pyridine/$H_2O$ (100 μL/20 μL) was added and the resulting dark solution was stirred at 25° C. for 30 min before a 10% aqueous solution of $Na_2S_2O_3$ was added to quench the excess of iodine. The volatiles were evaporated under reduced pressure ($NBu_3$ and DMF could not be removed), water (3 ml) was added and the mixture was allowed to stand at 25° C. for 1 h to hydrolyze the cyclic triphosphate moiety (observation of a white precipitate). The aqueous solution was washed with $CH_2Cl_2$ before being concentrated at 35° C. under vacuum. Methanol was added to the residue to lead to a precipitate which was sonicated and centrifuged to remove the methanol. This operation was repeated two times and the final residue was dried under vacuum. Purification by reverse-phase HPLC using TBAB and $CH_3CN$ as mobile phase afforded the desired nucleoside triphosphates (1) to (7).

Example 3: Deprotection of Reversible Terminators

The deprotection mechanisms for removing the removable terminating groups from the 3'-position of the reversible terminators are described as follows. Advantageously, the nucleoside triphosphate reversible terminators designed in accordance with various embodiments disclosed herein possess unique features such that they can be removed under mild reaction conditions. In particular, the removal of the removable terminating groups can be performed in aqueous conditions.

Deprotection of 2-cyanoethyl ether (CE) and/or (2-cyanoethoxy)methyl (CEM)

The deprotection of the CE and/or CEM groups can be performed in basic conditions at temperatures ranging from 25° C. to 80° C., as shown in Scheme 11. For example, aqueous solutions of ammonia ($NH_4OH$) can be used to successfully remove the CE group.

Scheme 11. Deprotection of CE-dTTP reversible terminator (1) and CEM-dTTP reversible terminator (7)

CE deprotection

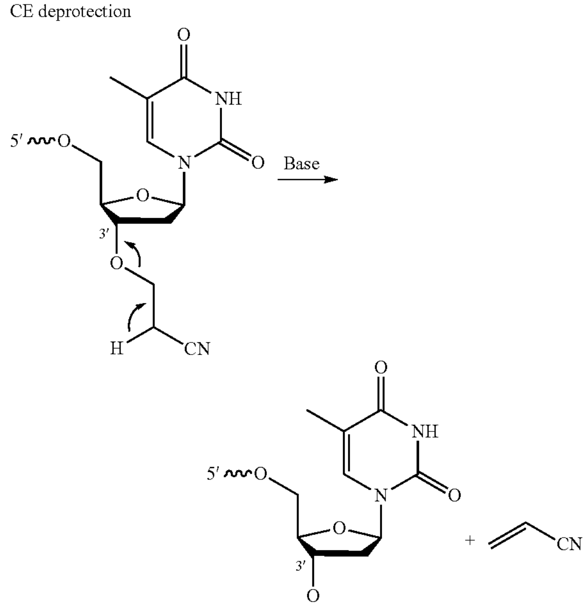

CEM deprotection

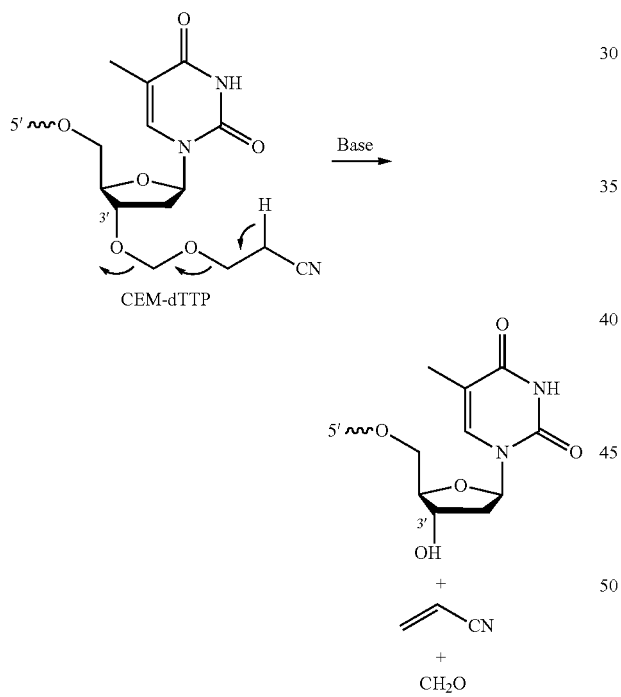

Deprotection of Disulfide Carbonate (DT) or Carbamate

The deprotection of disulfide carbonate or carbamate group can be performed in a reductive environment at 25° C., as shown in Scheme 12. For example, aqueous solutions of dithiothreitol (DTT) or tris(2-carboxyethyl)phosphine) (TCEP) can be used to successfully remove the disulfide carbonate or carbamate group.

In particular, the disulfide bond (or disulfide self-immolative linker) in disulfide carbonate or carbamate can be cleaved under aqueous reductive conditions and subsequent cyclization of the resulting thiol can restore the 3'-hydroxy of the nucleotide. An important aspect of this mechanism is that the 5-membered ring released is an unreactive species unable to react with the nucleobases of the nucleotide sequence or oligonucleotide.

Scheme 12. Deprotection of disulfide carbonate or carbamate, for e.g. DT-dTTP reversible terminator (2)

Disulfide self-immolative linker deprotection releasing an unreactive cyclic by-product

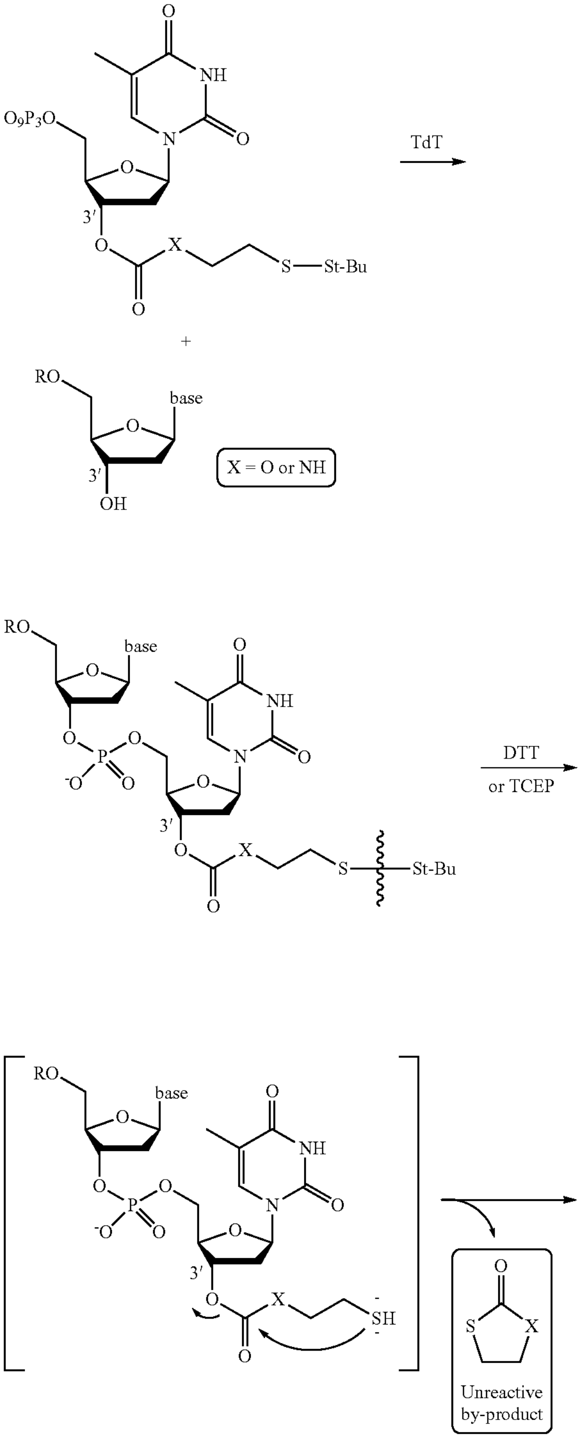

-continued

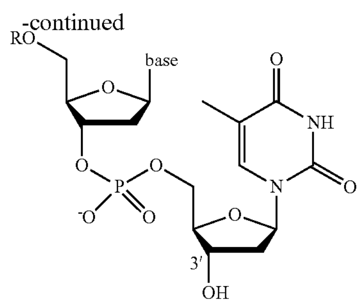

Deprotection of 2-(Trimethylsilyl)Ethoxymethyl (SEM)

The deprotection of the SEM group can be performed in a mildly basic environment or in aqueous solutions of fluoride sources like tetra-n-butylammonium fluoride (TBAF) or potassium fluoride (KF).

Deprotection of (Allyloxy)Methyl (ALM)

The deprotection of the ALM group can be performed in the presence of transition metal(s), as shown in Scheme 13. Examples of transition metals include but are not limited to palladium, ruthenium, rhodium and platinum salts.

Scheme 13. Deprotection of ALM-dTTP reversible terminator (4)

ALM deprotection

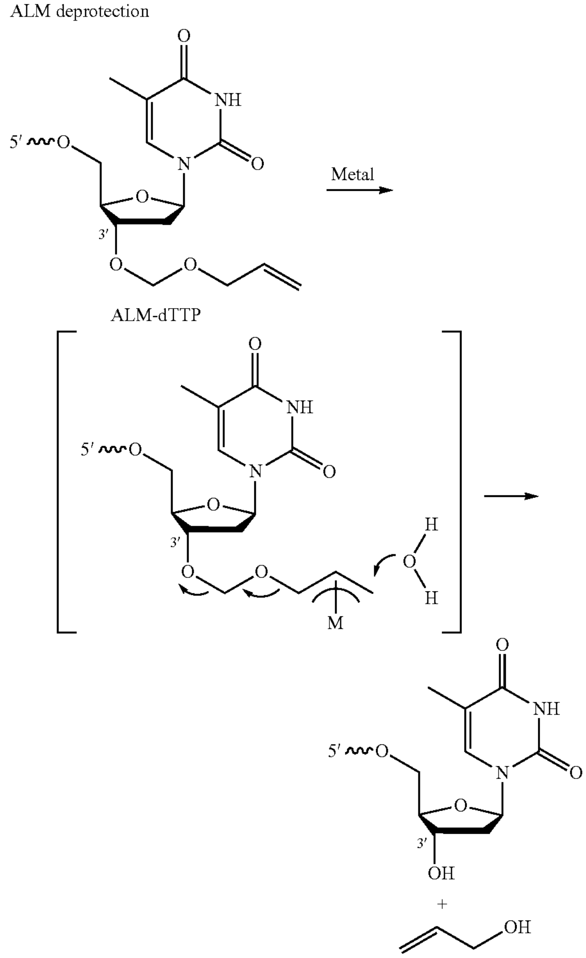

Deprotection of 4-Nitrobenzyloxy-Methyl (PNBA)

The deprotection of the PNBA group can be performed in a reductive environment followed by an exposure to acidic conditions, as shown in Scheme 14. Alternatively, the nitro group can be reduced in the presence of nitroreductase (NTR) enzyme or electrochemical conditions.

Scheme 14. Deprotection of PNBA-dTTP reversible terminator (5)

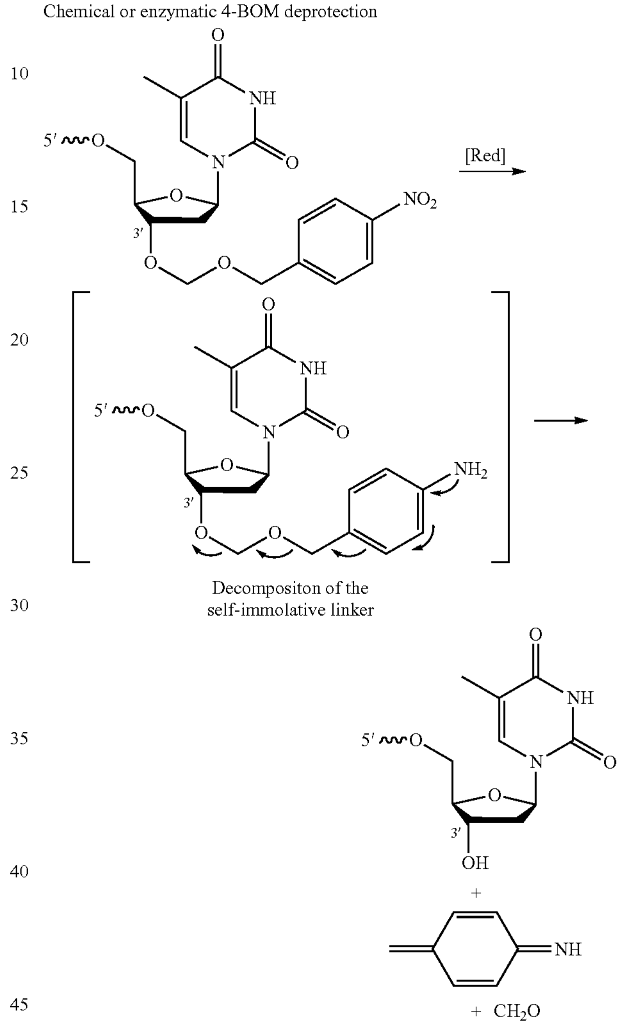

Deprotection of Dithianemethyl Acetal (DMA)

The deprotection of the DMA group can be performed in a mild oxidative environment at 25° C. like in aqueous solutions of $NaIO_4$, iodine, oxone or peroxides (e.g., $H_2O_2$). The deprotection of the DMA group can also be performed in sodium periodate, followed by subjecting to mild basic conditions at a pH of about 8, in the presence of a base. Examples of the base include but are not limited to potassium carbonate ($K_2CO_3$) and aniline ($PhNH_2$).

Example 4: Incorporation of Reversible Terminators into Nucleic Acids

A series of screening experiments were designed and conducted to test the recognition of the reversible terminators nucleoside triphosphate reversible terminators designed in accordance with various embodiments disclosed herein by template-independent polymerase and the efficiency of the incorporation of such reversible terminators into the nucleic acid chain.

In these experiments, the template-independent polymerase used is recombinant or engineered template-independent terminal deoxynucleotidyl transferase (TdT) enzyme and the initiator used is a single-stranded oligonucleotide sequence.

Materials Used in Screening Experiments

FAM-20-mer: [FAM]TGTAGTGTCTTGTTCTGTGA (SEQ. ID NO. 1)

rTdT: recombinant terminal deoxynucleotidyl transferase (TdT)

eTdT: engineered terminal deoxynucleotidyl transferase (TdT)

RT-dTTP: reversibly terminated deoxythymidine triphosphate

Terminal deoxynucleotidyl transferase (TdT) is an enzyme that catalyzes the addition of mononucleotides from dTTPs to the terminal 3'-OH of a DNA initiating sequence, accompanied by the release of inorganic pyrophosphate. The enzyme thus provides a unique method for the base by base enzymatic incorporation.

Reversibly terminated deoxynucleotidyl triphosphates (RT-dNTPs) provided building blocks to be used in TdT catalyzed enzymatic nucleotide synthesis.

Two screening methods were used to evaluate the RT-dNTPs' incorporation capabilities with TdT and termination activity. One method is tailing experiment design and the other is laddering experiment design.

Figure 5:
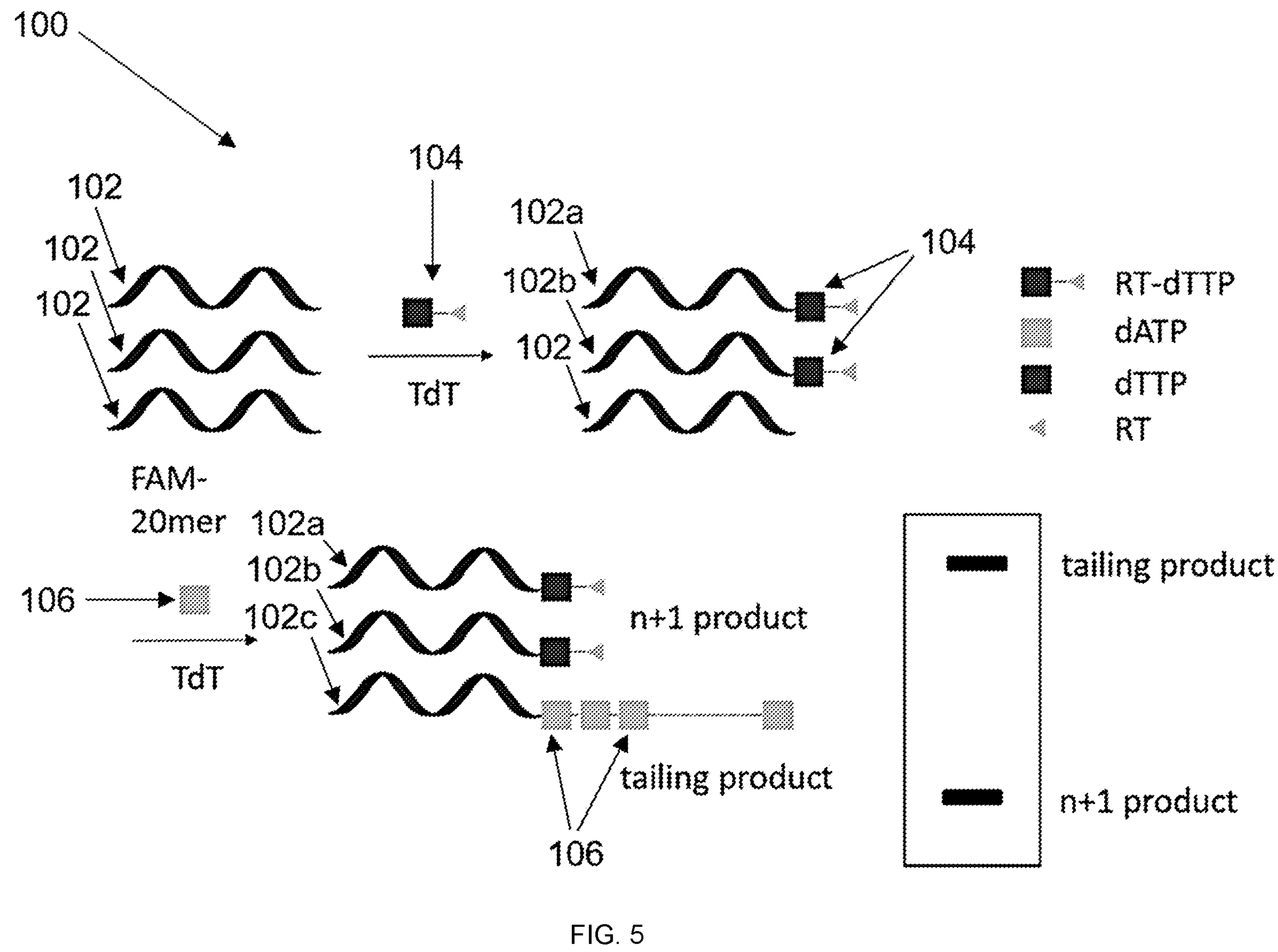
FIG. 5 is a schematic diagram 100 for illustrating a tailing experiment design developed for evaluating the incorporation and termination activities of the nucleoside triphosphate reversible terminators (RT-dTTPs) designed in accordance with various embodiments disclosed herein.

Example 5: Evaluating RT-dNTP(s)'s Incorporation and Termination Activities Using Tailing Experiment Design In this experimental design (FIG. 5), single-stranded deoxyoligonucleotides (20 nt) 102 with FAM tagged on 5' end reacts with RT-dNTP 104 using TdT as the catalyst, and produce 21-mer (102a and 102b).

As the incorporation is not 100%, the unreacted FAM tagged oligo will further react with natural deoxynucleotidyl triphosphates (dATP) 106, and produces tailing products 102c. The 21-mer (102a and 102b) and tailing products (102c) can be separated by polyacrylamide gel electrophoresis.

Experimental Protocol for Tailing Experimental Design

Incorporation of RT-dNTP to the 3' Termini of Single-Stranded DNA Primers (FAM-20-Mer):

1. Set up the following reactions

| | |
|---|---|
| TdT 5 × Buffer | 4.0 μL |
| Primer (FAM-20-mer) | 2 pmole (1 μL of 2 μM) |
| RT-dTTP (10 mM) | 8 nmol (0.8 μL of 10 mM) |
| rTdT | 10-20 units (0.5 μL of original solution) |
| Water to a final volume of | 20 μL |

2. Incubate the solution at 37° C. for 60 min
3. Purification
   Desalt with Zymo column Oligo Clean & Concentrator D4061 (following manufacturer's protocol) to obtain 15 μL aqueous solution and concentrate on speedvac to dry Elongation of Nucleotide with Natural dATP:

4. Set up the following reactions

| | |
|---|---|
| TdT 5 × Buffer | 4.0 μL |
| Dry sample from step 3 | 2 pmol (0 μL) |
| dATP (10 mM) | 8 nmol (0.8 μL of 10 mM) |
| rTdT | 10-20 units (0.5 μL of original solution) |
| Water to a final volume of | 20 μL |

5. Incubate at 37° C. for 60 min
6. Stop the reaction by heating at 70° C. for 10 min
7. Purification
   Desalt with Zymo column Oligo Clean & Concentrator D4061 (following manufacturer's protocol) to obtain 15 μL aqueous solution and concentrate on speedvac to dry
8. Denaturing PAGE (20% urea PAGE, 200V for 90 min)
   Preheat 1×TBE buffer at 65° C.
   Set up gel in gel tank, flush wells, pre-run 20% urea polyacrylamide gel at 200V for 30 min
   Prepare loading sample (dry sample+2.5 μL 1×TBE, 0.5 μL loading buffer), preheat sample at 95° C. for 10 min
   Flush each well 3 times to remove urea in wells, load sample, and run for 90 min
   Image under UV light without post staining. If post staining is needed, SYBR Gold is used.

Evaluation Studies Using Tailing Experimental Design

In evaluating the RT-dTTP(s)'s incorporation and termination activities using tailing experiment design, two types of TdTs are used for the evaluation studies: recombinant TdT (rTdT) purchased from Promega and engineered TdT (eTdT).

Screening of RT-dTTPs with rTdT as Enzyme

DT-dTTP reversible terminator (2), SEM-dTTP reversible terminator (3), AL-dTTP reversible terminator (4), PNBA-dTTP reversible terminator (5) and DMA-dTTP reversible terminator (6) were tested alongside comparative examples namely, TBS-dTTP, ALE-dTTP, ONBA-dTTP and DTM-dTTP.

Figure 6A:
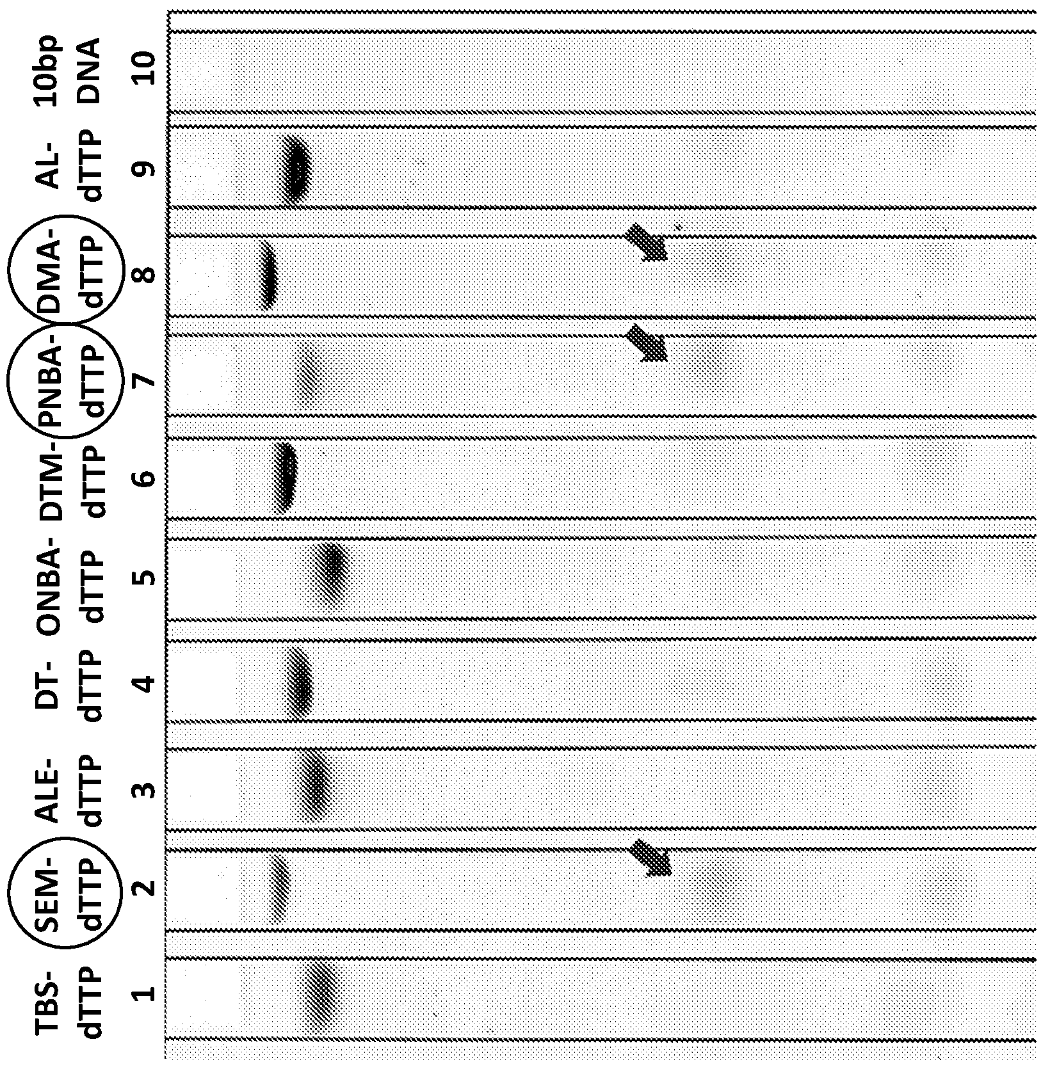
FIG. 6A shows polyacrylamide gel electrophoresis (PAGE) patterns of DT-dTTP reversible terminator (2), SEM-dTTP reversible terminator (3), AL-dTTP reversible terminator (4), PNBA-dTTP reversible terminator (5) and DMA-dTTP reversible terminator (6), tested alongside comparative examples namely, TBS-dTTP, ALE-dTTP, ONBA-dTTP and DTM-dTTP using the tailing experiment design (with recombinant TdT as enzyme).
Figure 6B:
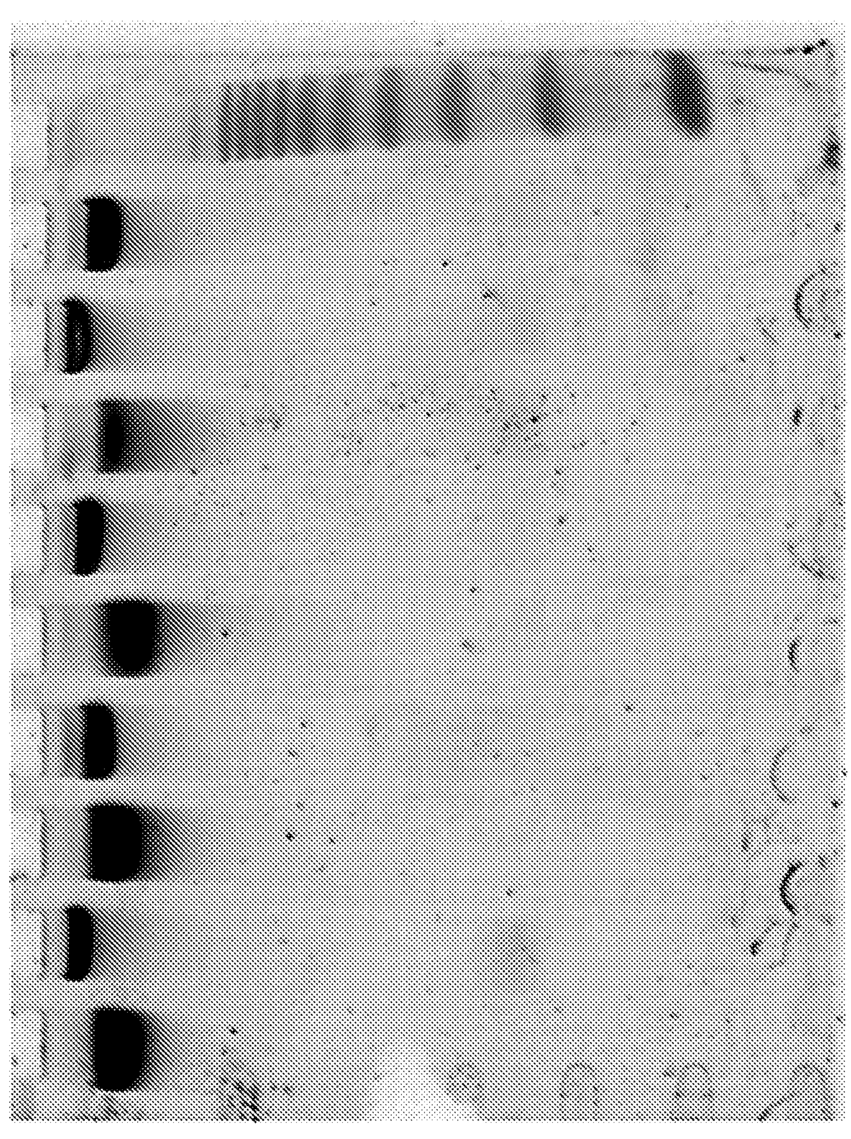
FIG. 6B shows the polyacrylamide gel electrophoresis (PAGE) patterns post stained with SYBR Gold).

The results obtained from screening RT-dTTPs with rTdT as enzyme are shown in FIG. 6A (FAM only) and FIG. 6B (which was post stained with SYBR Gold). As shown in FIG. 6A, when using rTdT as the enzyme, SEM-dTTP, PNBA-dTTP and DMA-dTTP gave 21-mer products, which indicated that these RT-dTTPs designed in accordance with various embodiments disclosed herein have been successfully incorporated into the original FAM-20-mer.

Figure 7A:
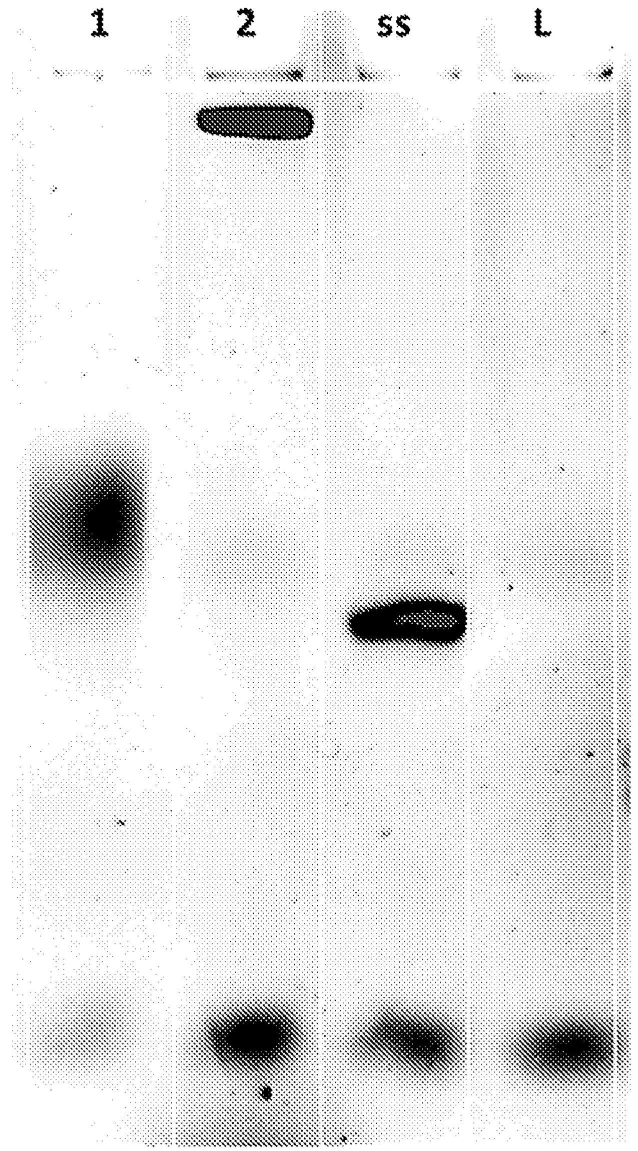
FIG. 7A shows polyacrylamide gel electrophoresis (PAGE) patterns of DT-dTTP reversible terminator (2) using the tailing experiment design (with recombinant TdT as enzyme).
Figure 7B:
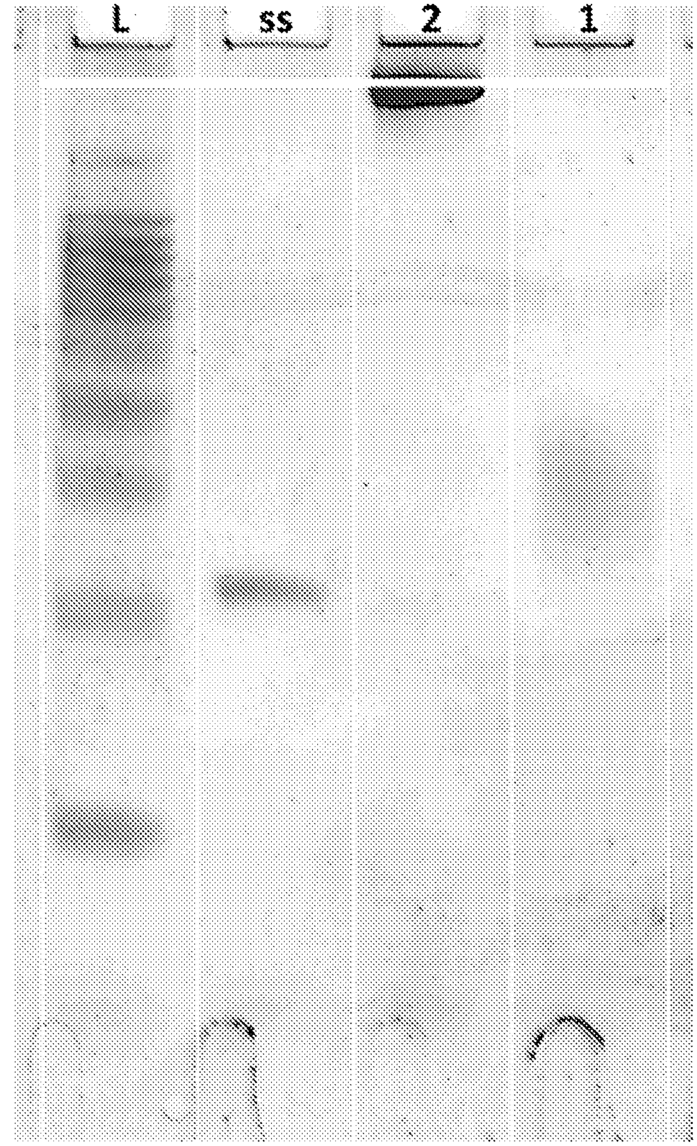
FIG. 7B shows the polyacrylamide gel electrophoresis (PAGE) patterns post stained with SYBR Gold. Lane 1 denotes reaction 1: FAM-20-mer+DT-dTTP/desalting+dATP/desalting; Lane 2 denotes reaction 2: FAM-20-mer+dATP/desalting; Lane ss denotes FAM-20-mer; and Lane L denotes 10 bp DNA ladder.

DT-dTTP showed particularly good yield of 21-mer, as can be seen from FIG. 7.

Screening of RT-dTTPs with eTdT as Enzyme

DT-dTTP reversible terminator (2), SEM-dTTP reversible terminator (3), AL-dTTP reversible terminator (4), PNBA-dTTP reversible terminator (5) and DMA-dTTP reversible terminator (6) were tested alongside comparative examples namely, TBS-dTTP, ALE-dTTP, ONBA-dTTP, DTM-dTTP and Ac-dTTP.

Figure 8A:
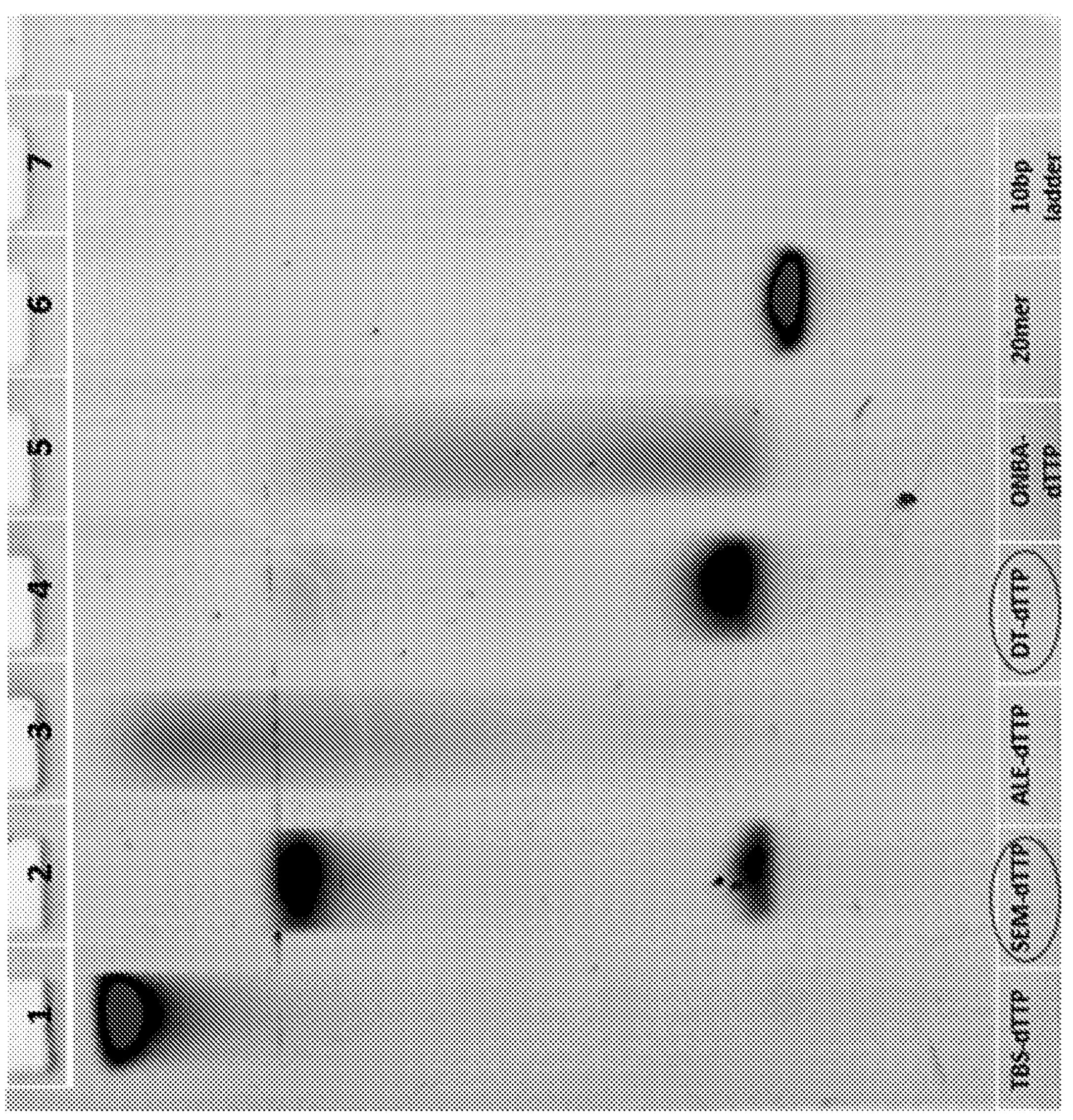
FIG. 8A and FIG. 8B show polyacrylamide gel electrophoresis (PAGE) patterns of DT-dTTP reversible terminator (2), SEM-dTTP reversible terminator (3), AL-dTTP reversible terminator (4), PNBA-dTTP reversible terminator (5) and DMA-dTTP reversible terminator (6), tested alongside comparative examples namely, TBS-dTTP, ALE-dTTP, ONBA-dTTP, DTM-dTTP and Ac-dTTP using the tailing experiment design (with engineered TdT as enzyme).
Figure 8B:
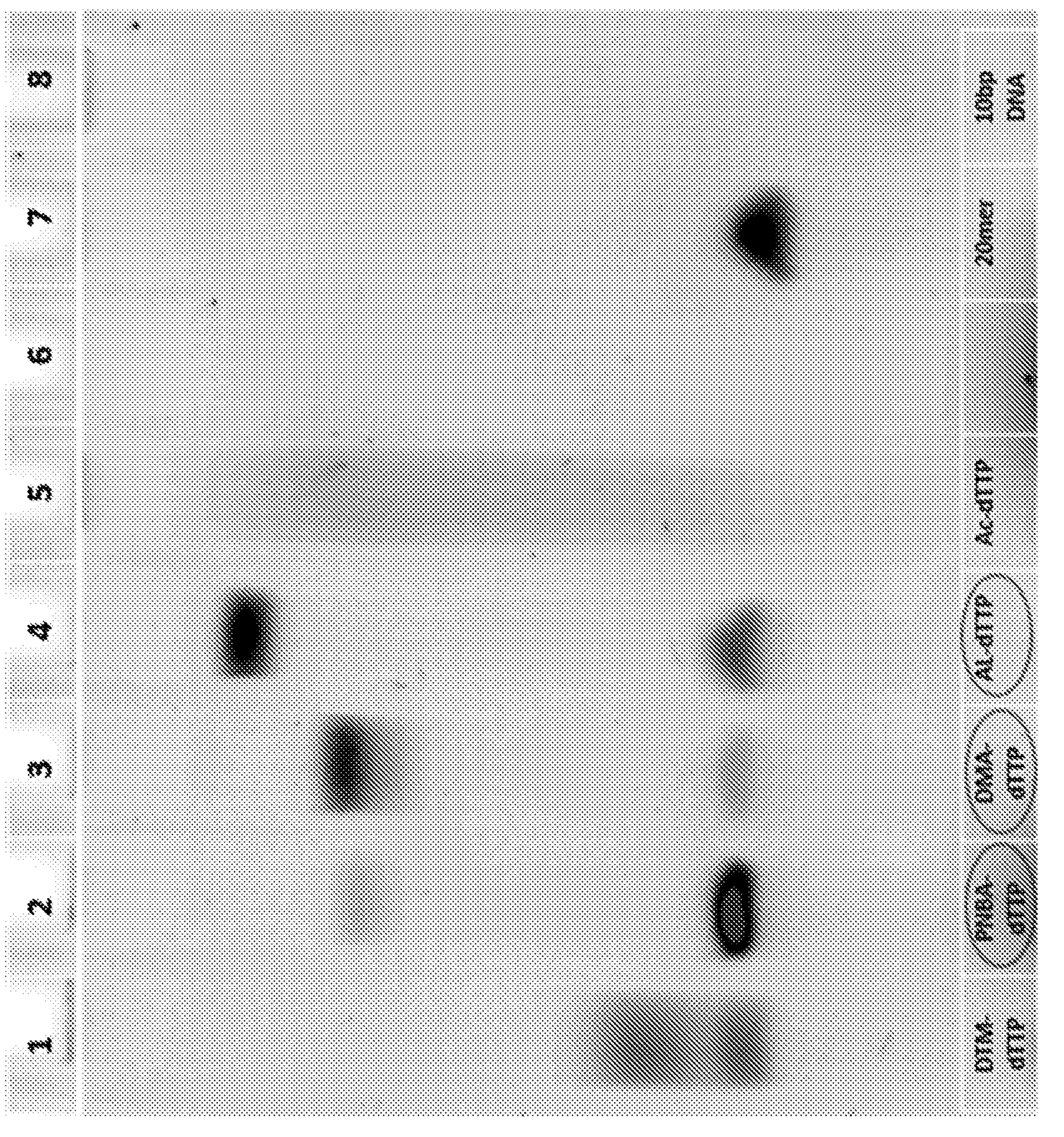
Figure 9A:
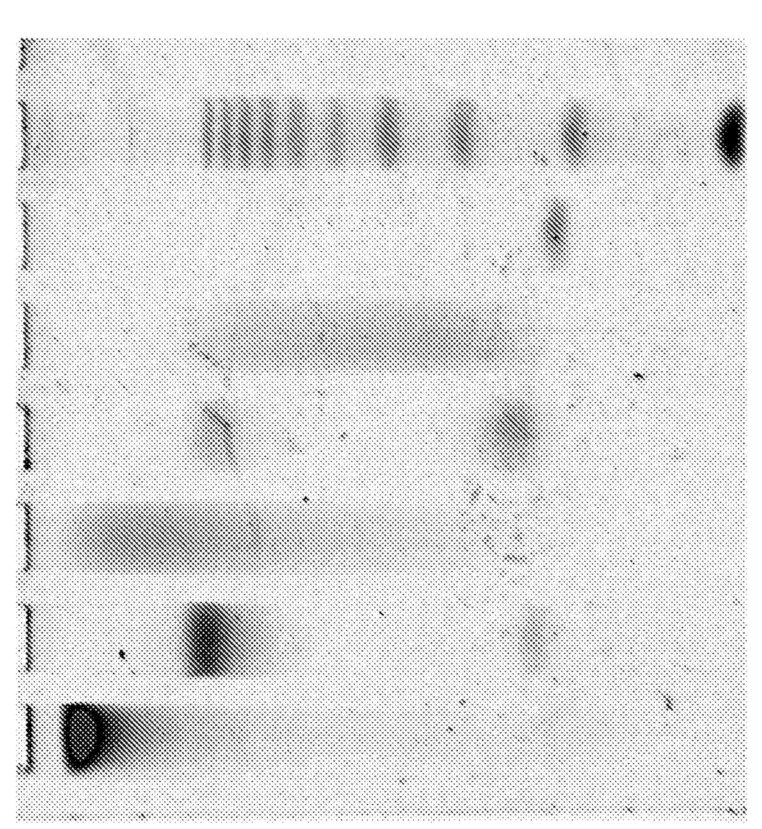
FIG. 9A and FIG. 9B show the polyacrylamide gel electrophoresis (PAGE) patterns of FIG. 8A and FIG. 8B respectively post stained with SYBR Gold. The conditions are as follows: 15% Urea PAGE, 150V, 7A, 53 minutes taken for blue dye to reach edge.
Figure 9B:
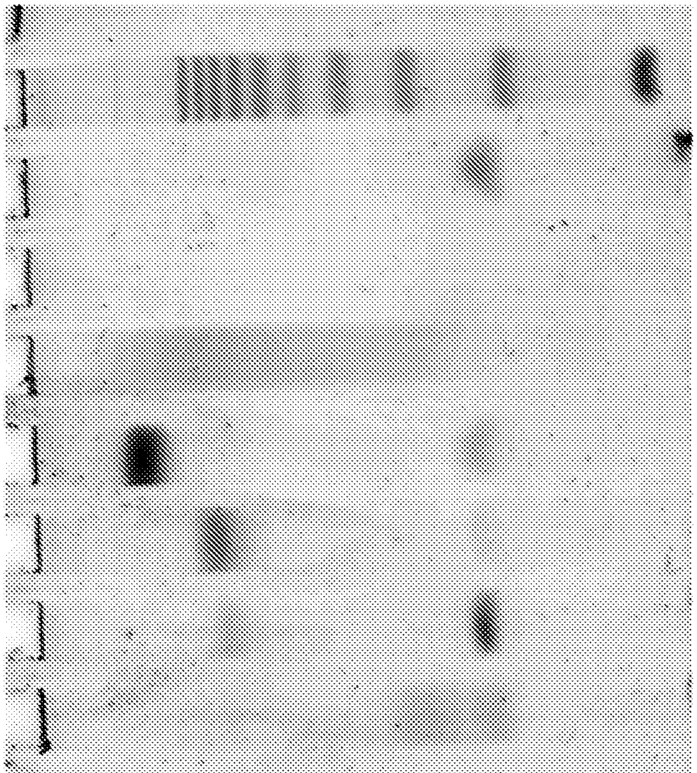

The results obtained from screening RT-dTTPs with eTdT as enzyme are shown in FIG. 8A and FIG. 8B (FAM only). The results post stained with SYBR Gold are shown in FIG. 9A and FIG. 9B.

As shown in FIG. 8A and FIG. 8B, when using eTdT as the enzyme, SEM-dTTP, DT-dTTP, PNBA-dTTP, DMAdTTP and AL-dTTP gave 21-mer products, which indicated that these RT-dTTPs designed in accordance with various embodiments disclosed herein have been successfully incorporated into the original FAM-20-mer.

Summary of Results

As can be seen from the reactions above, it can be concluded that SEM-dTTP, DT-dTTP, PNBA-dTTP, DMA-dTTP and AL-dTTP can be successfully incorporated in single stranded oligonucleotide via the catalysis of TdT and also terminate further base incorporation.

Screening of RT-dTTPs Using rTdT Vs. eTdT

Figure 10A:
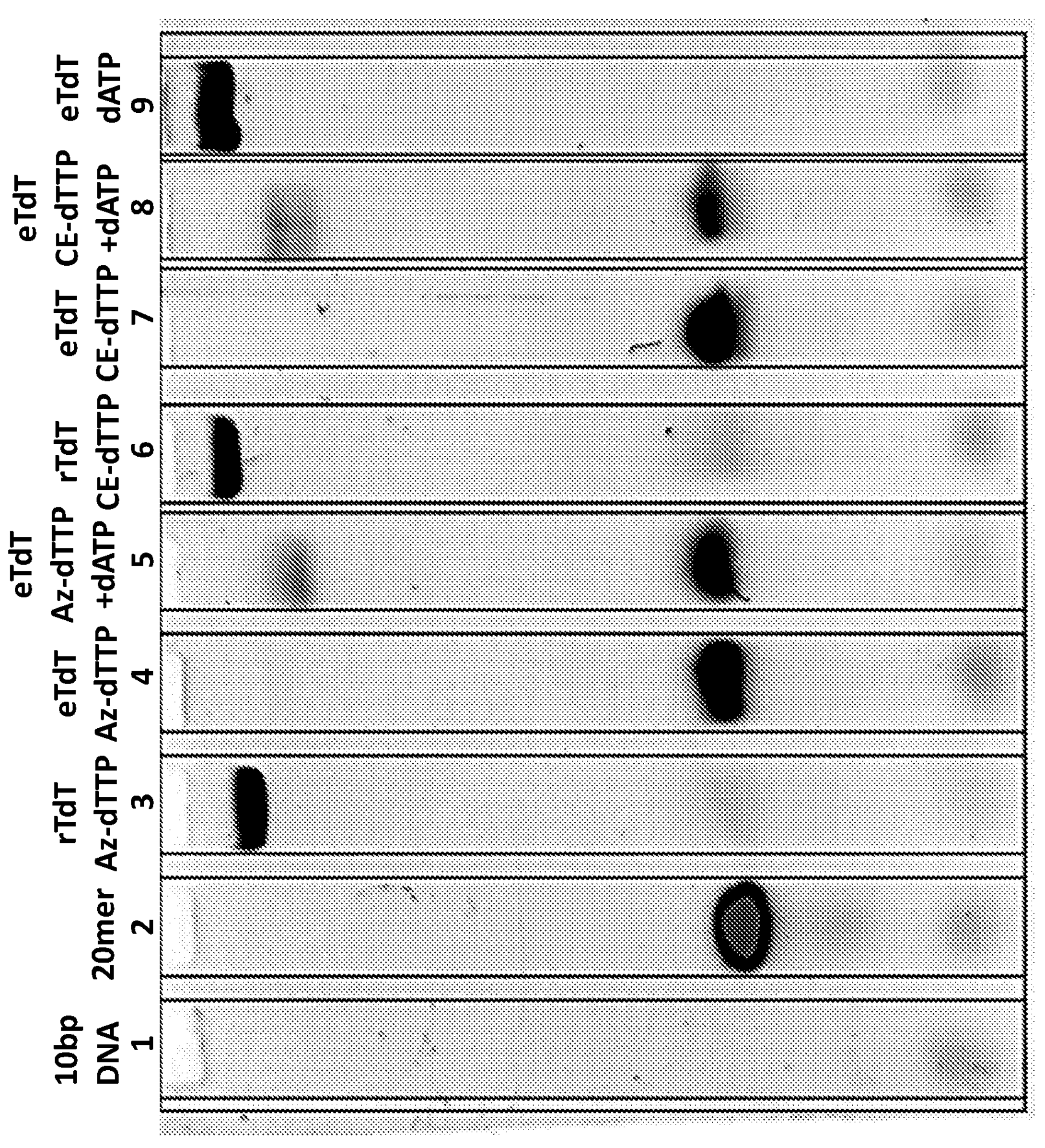
FIG. 10A shows the polyacrylamide gel electrophoresis (PAGE) patterns of CE-dTTP reversible terminator (1) and Az-dTTP (with engineered TdT as enzyme) versus CE-dTTP reversible terminator (1) and Az-dTTP (with recombinant TdT as enzyme).
Figure 10B:
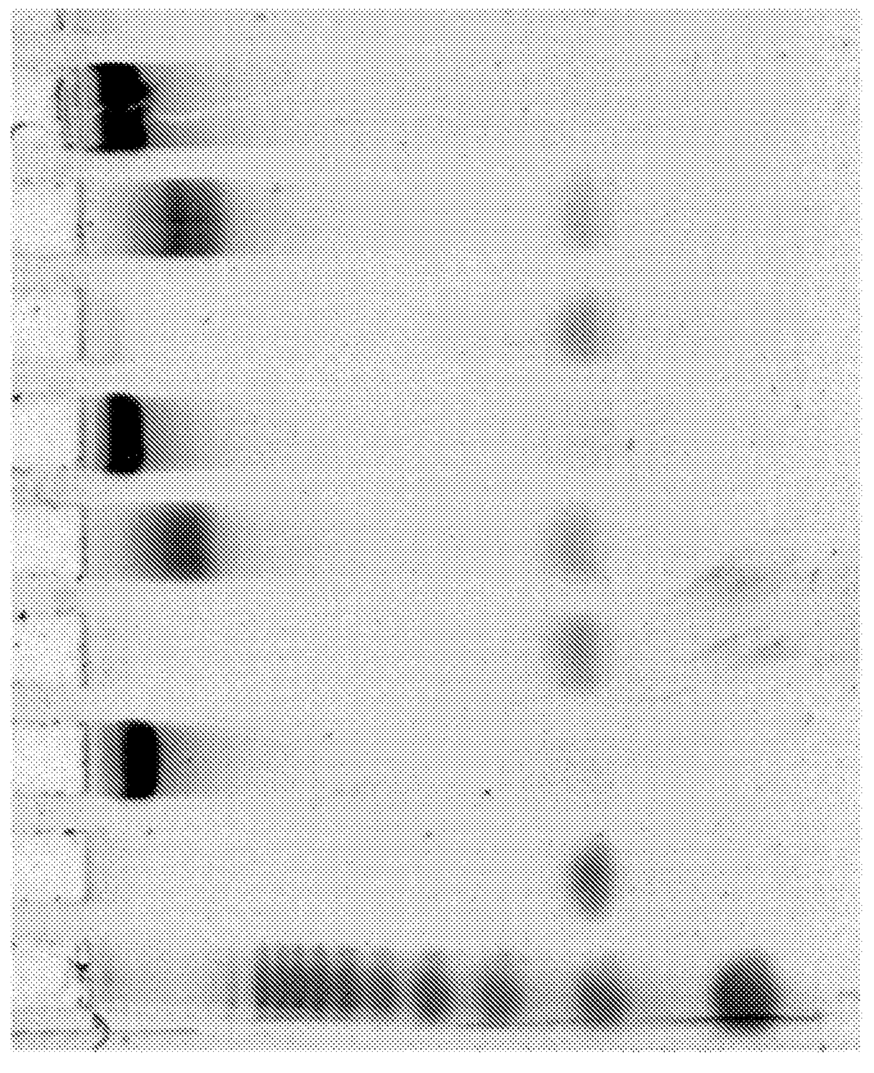
FIG. 10B shows the polyacrylamide gel electrophoresis (PAGE) patterns post stained with SYBR Gold.

Using Az-dTTP and CE-dTTP, the catalytic activity of rTdT was compared with that of eTdT as shown in FIG. 10A (FAM only) and FIG. 10B (post stained with SYBR Gold). The results shown in FIG. 10 indicated that the engineered eTdT has much high incorporation yield than rTdT.

Example 6: Evaluating RT-dNTP(s)'s Incorporation and Termination Activities Using Laddering Experiment Design The laddering experiment design is to differentiate the ratio between natural dNTP and RT-dNTP. If RT-dNTP can be successfully incorporated and terminated the reaction, the results of the enzymatic synthesis will be a mixture of incorporation products.

Experimental Protocol for Laddering Experimental Design

Laddering Experiment Design:

| |
|---|
| Rxn 1 - 5'-FAM-20-mer + 100% dATP |
| Rxn 2 - 5'-FAM-20-mer + 25% dATP + 75% RT-dTTP |
| Rxn 3 - 5'-FAM-20-mer + 2.5% dATP + 97.5% RT-dTTP |
| Rxn 4 - 5'-FAM-20-mer + 0.25% dATP + 99.75% RT-dTTP |
| Rxn 5 - 5'-FAM-20-mer + 100% RT-dTTP |
| Rxn 6 - 5'-FAM-20-mer + 100% RT-dTTP (no TdT) |

Incorporation of RT-dTTP to the 3' Termini of Single-Stranded DNA Primers:

1. Set up the following reactions

| | |
|---|---|
| Promega TdT 5 × Buffer | 4 μL |
| Primer (FAM-20mer) | 2 pmol (μL of 2 μM) |
| dATP (10 mM) | X % of 8 nmol (0.8 μL of 10 mM) |
| RT-dTTP (10 mM) | (100-X) % of 8 nmol (0.8 μL of 10 mM) |
| rTdT | 10-20 units (0.5 μL of original solution) |
| Water to a final volume of | 20 μL |

2. Incubate at 37° C. for 60 min
3. Stop the reaction by heating at 70° C. for 10 min
4. Purification
   Desalt with Zymo column Oligo Clean & Concentrator D4061 (following manufacturer's protocol) to obtain 15 μL aqueous solution and concentrate on speedvac to dry
5. Denaturing PAGE (20% urea PAGE, 200V for 90 min)
   Preheat 1×TBE buffer at 65° C.
   Set up gel in gel tank, flush wells, pre-run 20% urea polyacrylamide gel at 200V for 30 min
   Prepare loading sample (dry sample+2.5 μL 1×TBE, 0.5 μL loading buffer), preheat sample at 95° C. for 10 min
   Flush each well 3 times to remove urea in wells, load sample, and run for 90 min
   Image under UV light without post staining. If post staining is needed, SYBR Gold is used.

Evaluation of Studies Using Laddering Experimental Design

Figure 11:
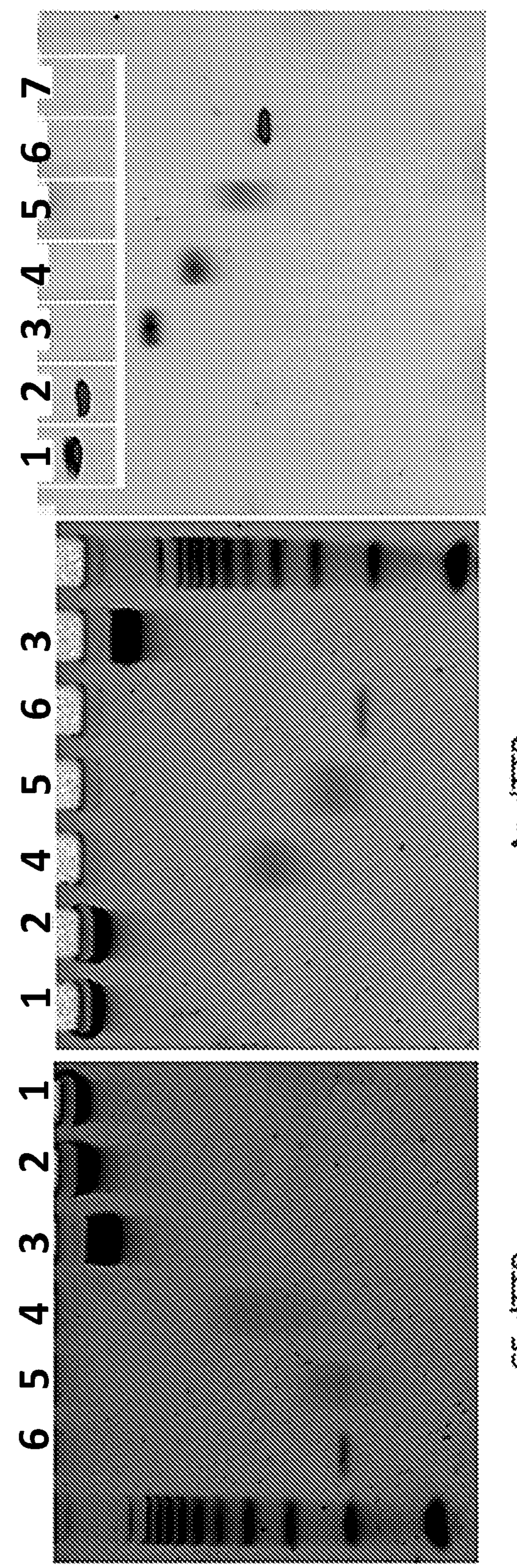
FIG. 11 shows polyacrylamide gel electrophoresis (PAGE) patterns of CE-dTTP reversible terminator (1) and DT-dTTP reversible terminator (2), tested alongside comparative example Az-dTTP using the laddering experiment design.

From the laddering experiments as shown in FIG. 11, it is shown clearly that CE-dTTP and DT-dTTP can terminate the reaction as well as Az-dTTP.

Example 7: Evaluation of Reversibility of Reversible Terminators

Figure 12:
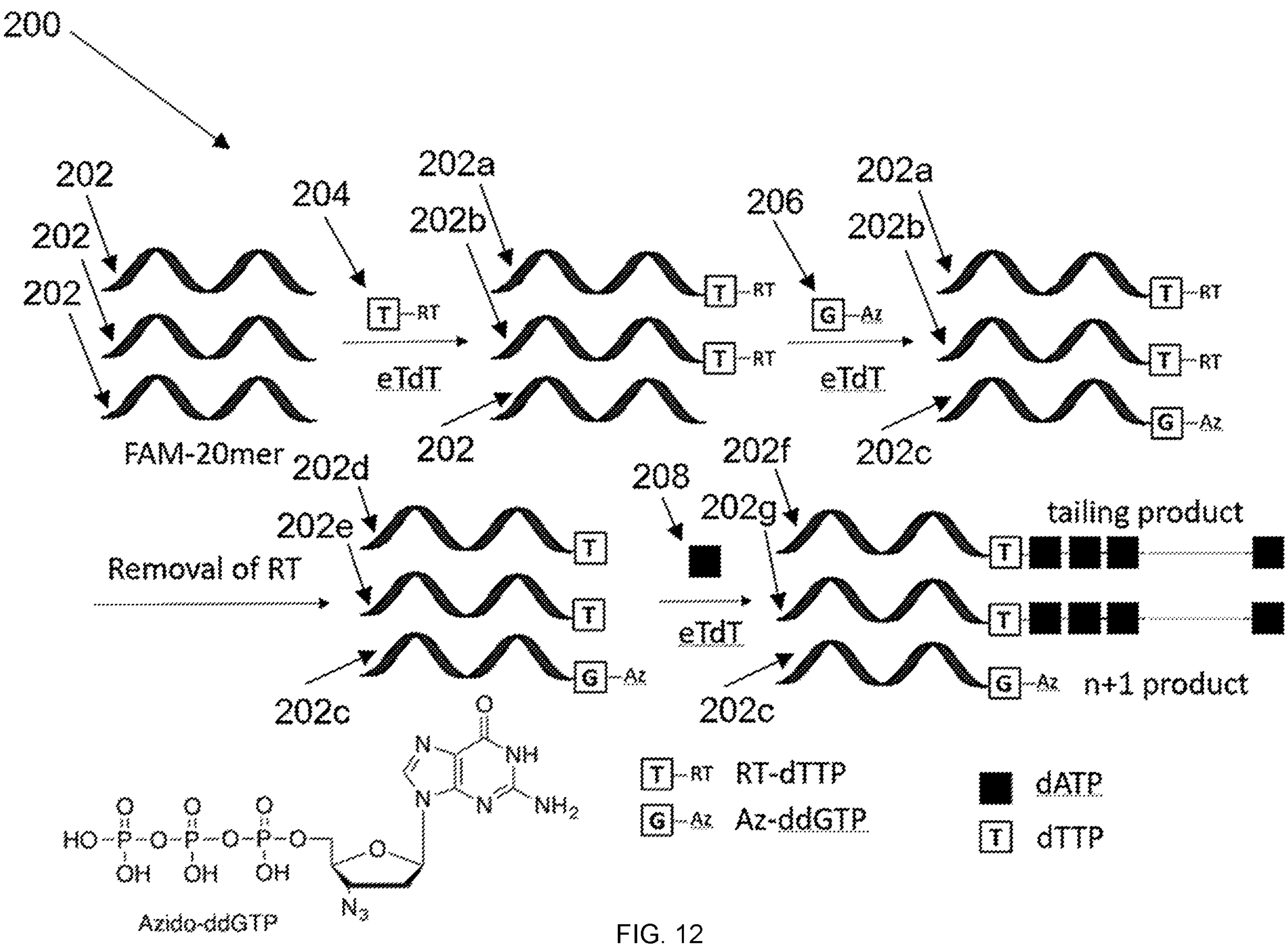
FIG. 12 is a schematic diagram 200 for illustrating an experimental design developed for evaluating the reversibility of the nucleoside triphosphate reversible terminators (RT-dTTPs) designed in accordance with various embodiments disclosed herein.

Once RT-dTTP is incorporated to the single-stranded oligonucleotide, the reversible terminator needs to be removed to enable the next base incorporation. To evaluate the reversibility of reversibly terminators, as shown in FIG. 12, RT-dTTPs 204 are first incorporated to single-stranded oligonucleotides (FAM-20-mer) 202 by eTdT. The reaction will produce a mixture of products which includes the reversibly terminated 21-mer (202a and 202b) and unreacted original 20-mer 202. Then azido-ddGTP 206 will be added to 3'-termini of the unreacted 20-mer 202. As 3' termini become a dideoxynucleotide 202c, the azido oligonucleotide will not be able to further react with any dTTP via TdT. Then reversibly terminator will be removed in certain conditions, and further incorporated with natural dTTP 208 via TdT. If there are tailing products (202f and 202 g), it indicates that reversibly terminator has been successfully removed.

Experimental Protocol for Evaluating CE's Reversibility

Incorporation of CE-dTTP to the 3' Termini of Single-Stranded DNA Primers (FAM-20-Mer):

1. Set Up the Following Reactions

| | |
|---|---|
| TdT 5 × Buffer | 4.0 μL |
| Primer (FAM-20-mer) | 2 pmol (1 μL of 2 μM) |
| RT-dTTP (10 mM) | 8 nmol (0.8 μL of 10 mM) |
| eTdT | 10-20 units (0.5 μL of original solution) |
| Water to a final volume of | 20 μL |

2. Incubate the solution at 37° C. for 60 min
3. Purification
   Desalt with Zymo column Oligo Clean & Concentrator D4061 (following protocol) to obtain 15 μL aqueous solution and concentrate on speedvac to dry Removal of CE:

4. Add 85 μL of 30% $NH_4OH$ and heat at 80° C. for 1 h
5. Purification
   Desalt with Zymo column Oligo Clean & Concentrator D4061 (following protocol) to obtain 15 μL aqueous solution and concentrate on speedvac to dry Elongation of Nucleotide with Natural dATP:

6. Set up the following reactions

| | |
|---|---|
| TdT 5 × Buffer | 4.0 μL |
| Dry sample from step 3 | 2 pmol (0 μL) |
| dATP (10 mM) | 8 nmol (0.8 μL of 10 mM) |
| rTdT | 10-20 units (0.5 μL of original solution) |
| Water to a final volume of | 20 μL |

7. Incubate at 37° C. for 60 min
8. Stop the reaction by heating at 70° C. for 10 min
9. Purification
   Desalt with Zymo column Oligo Clean & Concentrator D4061 (following protocol) to obtain 15 μL aqueous solution and concentrate on speedvac to dry
10. Denaturing PAGE (20% urea PAGE, 200V for 90 min)
   Preheat 1×TBE buffer at 65° C.
   Set up gel in gel tank, flush wells, pre-run 20% urea polyacrylamide gel at 200V for 30 min
   Prepare loading sample (dry sample+2.5 μL 1×TBE, 0.5 μL loading buffer), preheat sample at 95° C. for 10 min
   Flush each well 3 times to remove urea in wells, load sample, and run for 90 min
   Image under UV light without post staining. If post staining is needed, SYBR Gold is used.

Experimental Protocol for Evaluating DT's Reversibility

Incorporation of DT-dTTP to the 3' Termini of Single-Stranded DNA Primers (FAM-20-Mer):

1. Set up the following reactions

| | |
|---|---|
| TdT 5 × Buffer | 4.0 μL |
| Primer (FAM-20-mer) | 2 pmol (1 μL of 2 μM) |
| DT-dTTP (10 mM) | 8 nmol (0.8 μL of 10 mM) |
| eTdT | 10-20 units (0.5 μL of original solution) |
| Water to a final volume of | 20 μL |

2. Incubate the solution at 37° C. for 60 min
3. Purification
   Desalt with Zymo column Oligo Clean & Concentrator D4061 (following protocol) to obtain 15 μL aqueous solution and concentrate on speedvac to dry Removal of DT:

4. Add 0.1 M DTT solution for 1 h
5. Purification
   Desalt with Zymo column Oligo Clean & Concentrator D4061 (following protocol) to obtain 15 μL aqueous solution and concentrate on speedvac to dry Elongation of Nucleotide with Natural dATP:

6. Set up the following reactions

| | |
|---|---|
| TdT 5 × Buffer | 4.0 μL |
| Dry sample from step 3 | 2 pmol (0 μL) |

-continued

| | |
|---|---|
| dATP (10 mM) | 8 nmol (0.8 μL of 10 mM) |
| rTdT | 10-20 units (0.5 μL of original solution) |
| Water to a final volume of | 20 μL |

7. Incubate at 37° C. for 60 min
8. Stop the reaction by heating at 70° C. for 10 min
9. Purification
   Desalt with Zymo column Oligo Clean & Concentrator D4061 (following manufacturer's protocol) to obtain 15 μL aqueous solution and concentrate on speedvac to dry
10. Denaturing PAGE (20% urea PAGE, 200V for 90 min)
   Preheat 1×TBE buffer at 65° C.
   Set up gel in gel tank, flush wells, pre-run 20% urea polyacrylamide gel at 200V for 30 min
   Prepare loading sample (dry sample+2.5 μL 1×TBE, 0.5 μL loading buffer), preheat sample at 95° C. for 10 min
   Flush each well 3 times to remove urea in wells, load sample, and run for 90 min
   Image under UV light without post staining. If post staining is needed, SYBR Gold is used.

Reversibility Results of Reversible Terminators

In this experiment, CE-dTTP and DT-dTTP were used as the reversible terminations for evaluation.

Figure 13:
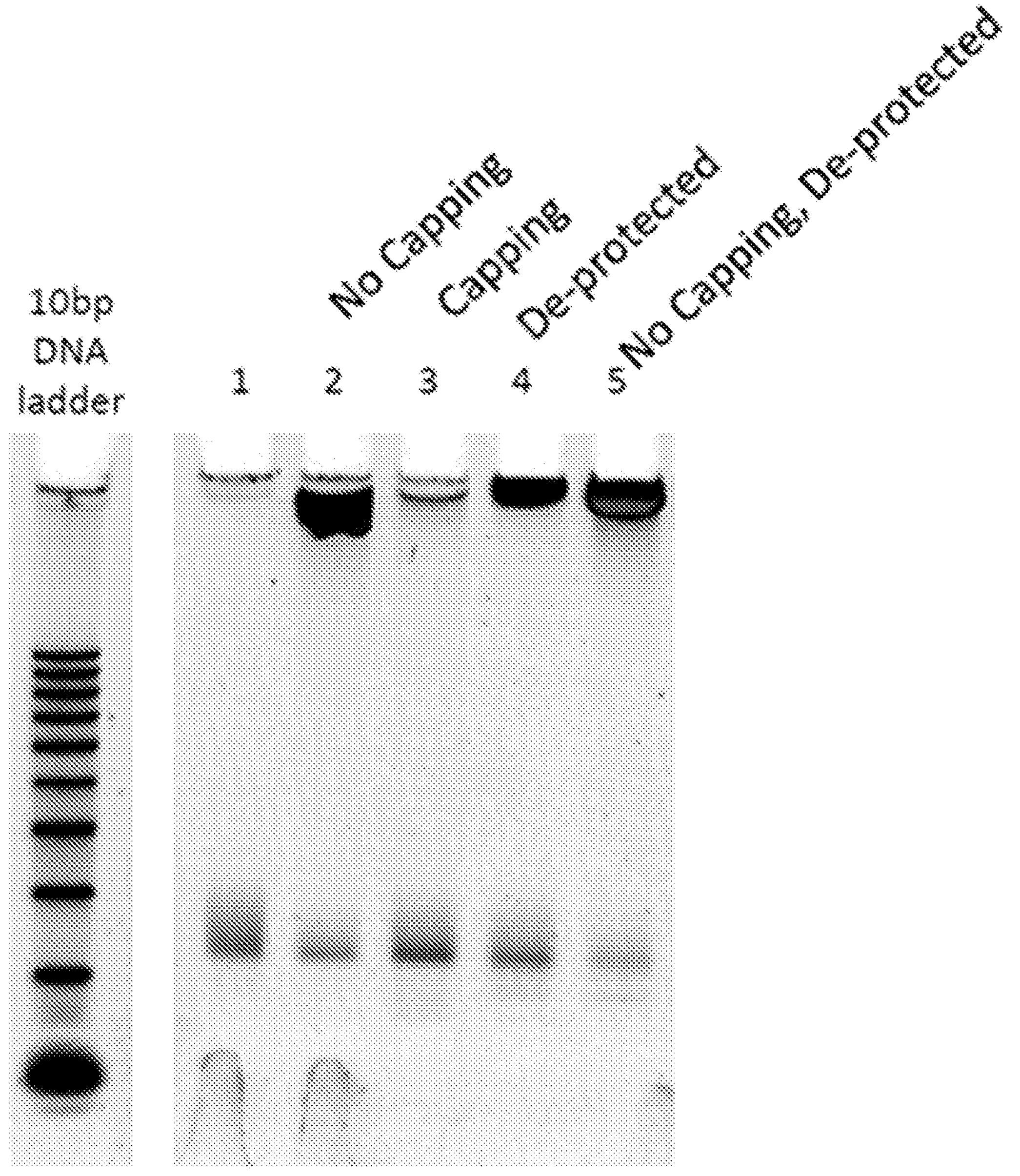
FIG. 13 shows polyacrylamide gel electrophoresis (PAGE) patterns of CE-dTTP reversible terminator (1) obtained from the reversibility screening experiments. Lane 1 denotes incorporation: reaction 1-5'-FAM-20 mer+CE-dTTP; Lane 2 denotes incorporation+elongation: reaction 2-5'-FAM-20 mer+25+CE-dTTP+dATP; Lane 3 denotes incorporation+capping+elongation: 5'-FAM-20 mer+CE-dTTP+Az-ddGTP+dATP; Lane 4 denotes incorporation+capping+deprotection+elongation: reaction 4-5'-FAM-20 mer+CE-dTTP+Az-ddGTP+deprotection+dATP; Lane 5 denotes incorporation+deprotection+elongation: reaction 5-5'-FAM-20 mer+CE-dTTP+deprotection+dATP.
Figure 14:
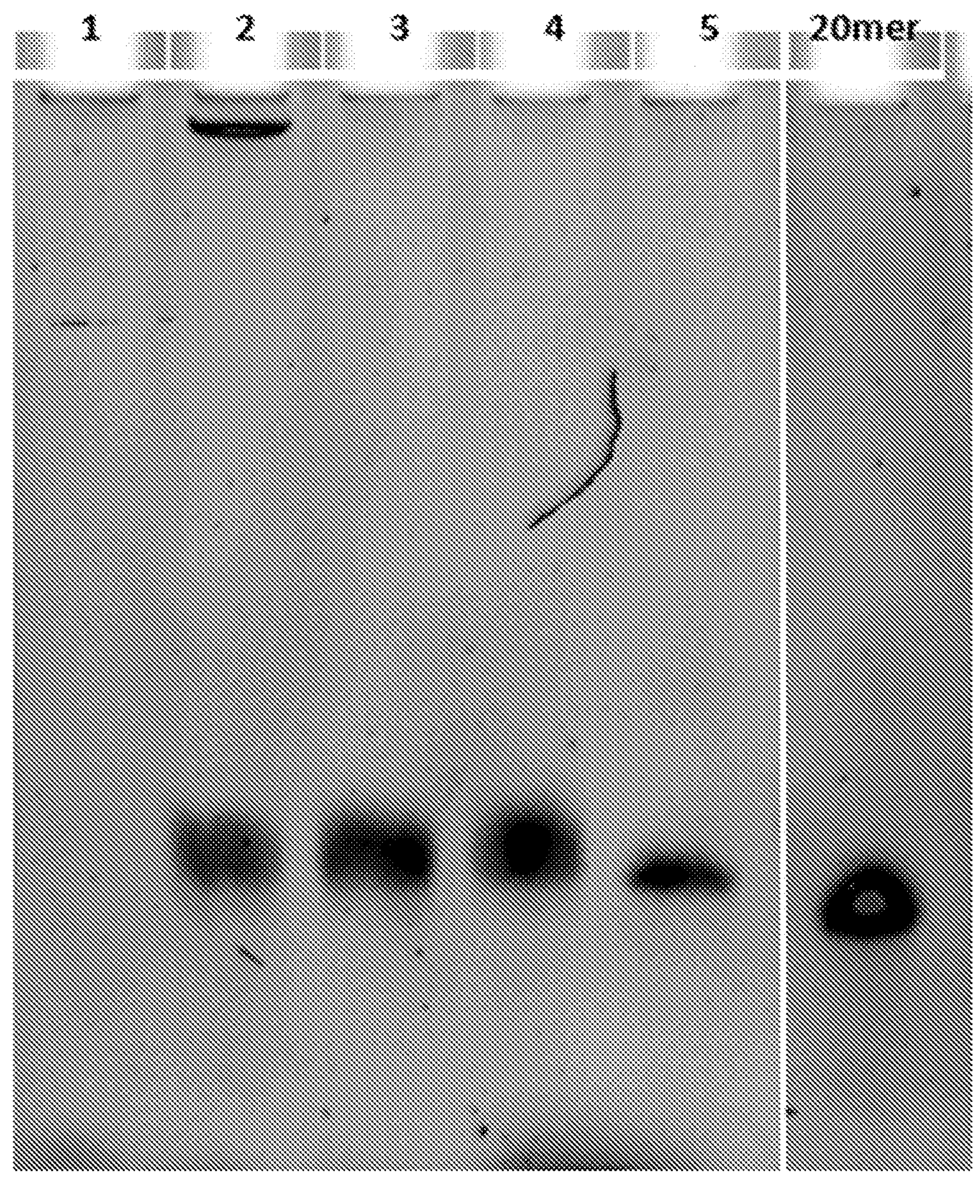
FIG. 14 shows polyacrylamide gel electrophoresis (PAGE) patterns of CE-dTTP reversible terminator (1) obtained from the reversibility screening experiments. Lane 1 is loaded with 10 bp ladder; Lane 2 (reverse) is loaded with FAM-20-mer+CE-dTTP+Az-ddGTP+CE deprotection+dATP; Lane 3 (non reverse) is loaded with FAM-20-mer+CE-dTTP+Az-ddGTP+dATP; Lane 4 (no tailing) is loaded with FAM-20-mer+CE-dTTP+Az-ddGTP; and Lane 5 (no CE-dTTP) is loaded with FAM-20-mer+Az-ddGTP+CE deprotection+dATP.
Figure 15:
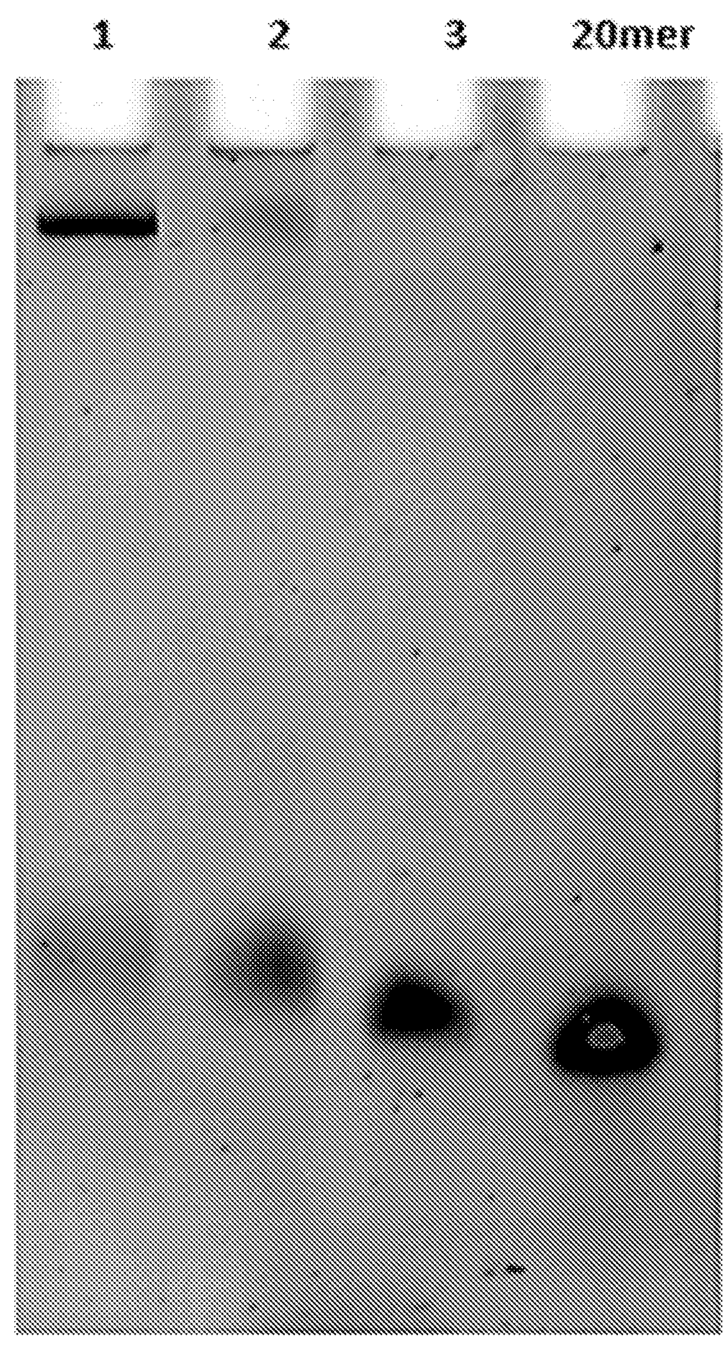
FIG. 15 shows polyacrylamide gel electrophoresis (PAGE) patterns of DT-dTTP reversible terminator (2) obtained from the reversibility screening experiments. Lane 1 (reverse) is loaded with FAM-20-mer+DT-dTTP+Az-ddGTP+DT deprotection+dATP; Lane 2 (non reverse) is loaded with FAM-20-mer+DT-dTTP+Az-ddGTP+dATP; Lane 3 (no DT-dTTP) is loaded with FAM-20-mer+Az-ddGTP+DT deprotection+dATP; and Lane 4 is loaded with FAM-20-mer.

As shown in FIG. 13 and FIG. 14, removal of CE was successful and 3'-OH was retrieved. FIG. 13 shows that 3'-CE can be deprotected and the retrieved 3'-OH can further react with dATP. As shown in FIG. 15, removal of DT was also successful. In summary, both CE and DT are successfully removed, and the resulted oligonucleotides are able to incorporate with natural dTTP after deprotection of CE or DT.

Accordingly, it is shown that the method of synthesizing single-stranded nucleotide sequence is effective and the reversible terminators nucleoside triphosphate reversible terminators designed in accordance with various embodiments disclosed herein were successfully incorporated into single-stranded nucleotide sequences using recombinant or engineered template-independent terminal deoxynucleotidyl transferase (TdT) enzyme.

It will be appreciated by a person skilled in the art that other variations and/or modifications may be made to the embodiments disclosed herein without departing from the spirit or scope of the disclosure as broadly described. For example, in the description herein, features of different exemplary embodiments may be mixed, combined, interchanged, incorporated, adopted, modified, included etc. or the like across different exemplary embodiments. The present embodiments are, therefore, to be considered in all respects to be illustrative and not restrictive.

The invention claimed is:

1. A method of synthesizing a single-stranded nucleotide sequence, the method comprising:

(i) adding a blocked nucleoside triphosphate to an initiator nucleotide sequence and incorporating a corresponding blocked nucleotide thereto in the presence of a polymerase, wherein the blocked nucleoside triphosphate has one of the general formulae (III) and (VI):

(III)

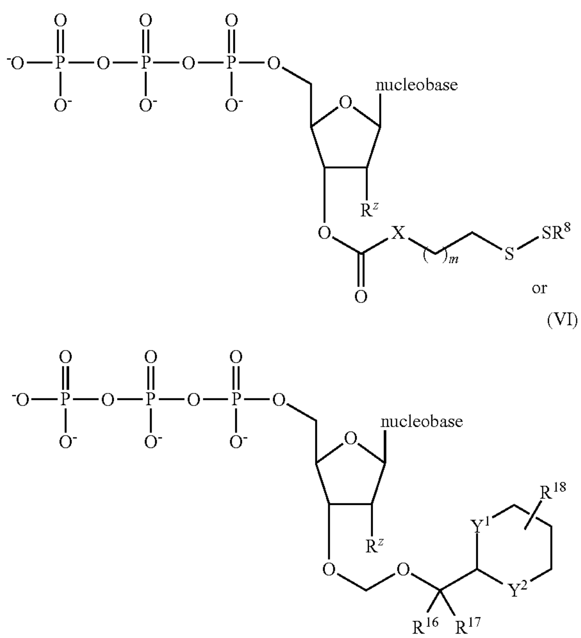

or (VI)

wherein m=0 to 20;

$R^z$ is H or OH;

$R^8$, $R^{16}$, $R^{17}$ and $R^{18}$ are independently selected from hydrogen, alkyl, alkenyl, aryl or heteroaryl;

X is a heteroatom selected from O, S or NH; and $Y^1$ and $Y^2$ are independently selected from S or Se.

2. The method of claim 1, further comprising:

(ii) removing a removable terminating group from the incorporated blocked nucleotide to obtain a corresponding nucleotide that is unblocked at the 3'-O position.

3. The method of claim 2, further comprising:

(iii) adding a blocked nucleoside triphosphate of any one of the general formulae (III) and (VI) to the 3'-O position of the unblocked nucleotide obtained in (ii) in the presence of the polymerase; and (iv) optionally repeating (ii) and/or (iii) one or more times until the single-stranded nucleotide sequence of a desired length is obtained.

4. The method of claim 1, wherein the polymerase is a template independent polymerase.

5. The method of claim 2, wherein (ii) of removing the removable terminating group is adapted to be carried out in aqueous conditions.

6. The method of claim 3, wherein each of (i) to (iv) of the method is adapted to be carried out in aqueous conditions.

7. The method of claim 1, wherein the nucleobase is selected from the group consisting of adenine (A), cytosine (C), guanine (G), thymine (T), uracil (U), uric acid, isocytosine, isoguanine, 2-aminopurine, 2,6-diaminopurine, 5-fluorouracil, 5-bromouracil, 5-chlorouracil, 5-iodouracil, hypoxanthine, xanthine, acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N-6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N-6-isopentenyladenine, uracil-5-oxy acetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil and 3-(3-amino-3-N-2-carboxypropyl) uracil.

8. The method of claim 1, wherein the method is devoid of the formation of side products that are reactive to the nucleobases of the nucleotide sequence.

9. The method of claim 1, wherein the single-stranded nucleotide sequence comprises a single-stranded deoxynucleotide sequence.

10. The method of claim 1, wherein the initiator nucleotide sequence comprises a single-stranded deoxynucleotide sequence or part thereof.

11. The method of claim 1, wherein the blocked nucleoside triphosphate comprises a deoxyribonucleoside triphosphate.

12. The method of claim 1, wherein the blocked nucleoside triphosphate is selected from the following:

(4A)

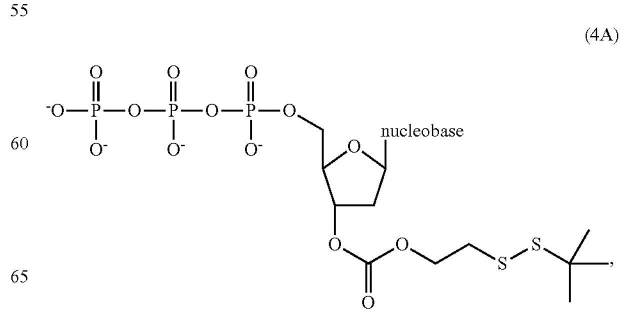

,

-continued (4B)

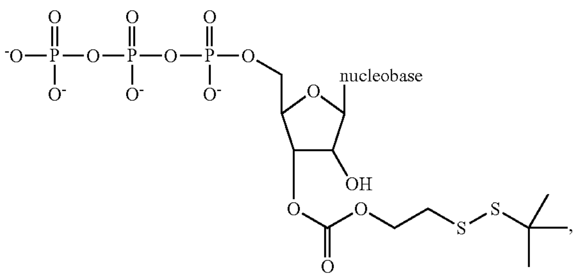

(5A)

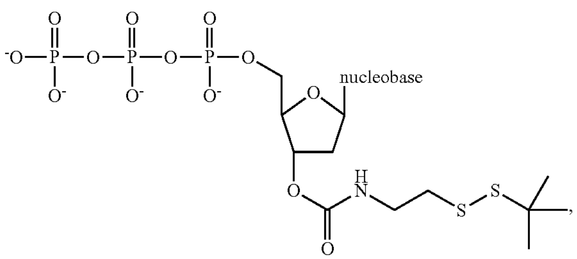

(5B)

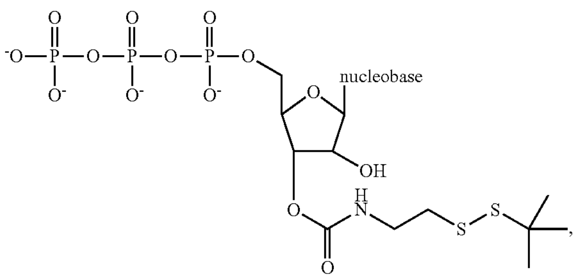

(8A)

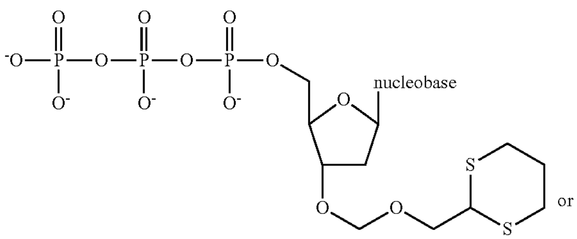

or (8B)

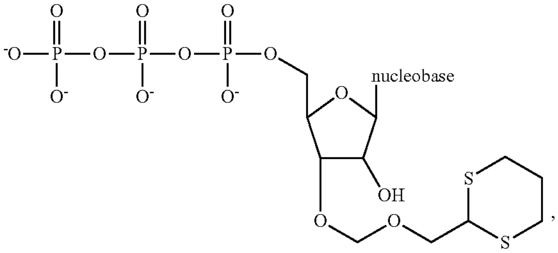

wherein nucleobase is selected from the group consisting of adenine (A), cytosine (C), guanine (G), uracil (U) and thymine (T).

13. The method of claim 3, wherein (i) and/or (iii) comprises forming a phosphodiester linkage between the initiator nucleotide sequence and the blocked nucleoside triphosphate.

14. The method of claim 3, wherein (i) and/or (iii) comprises release of a pyrophosphate.

15. A blocked nucleoside triphosphate for the method of claim 1, the blocked nucleoside triphosphate having any one of the general formulae (III) and (VI):

(III)

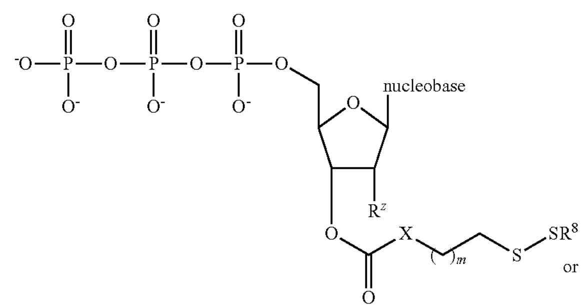

or (VI)

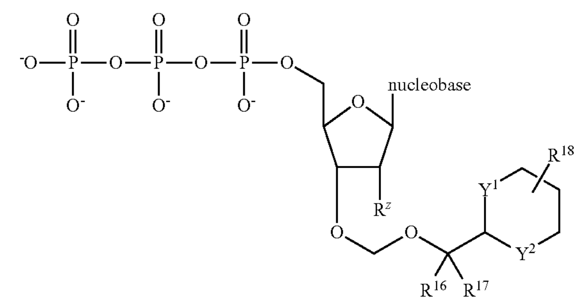

wherein m=0 to 20;

$R^z$ is H or OH;

$R^8$, $R^{16}$, $R^{17}$ and $R^{18}$ are independently selected from hydrogen, alkyl, alkenyl, aryl or heteroaryl;

X is a heteroatom selected from O, S or NH; and $Y^1$ and $Y^2$ are independently selected from S or Se.

16. The blocked nucleoside triphosphate according to claim 15, wherein the formulae is selected from the following:

(4A)

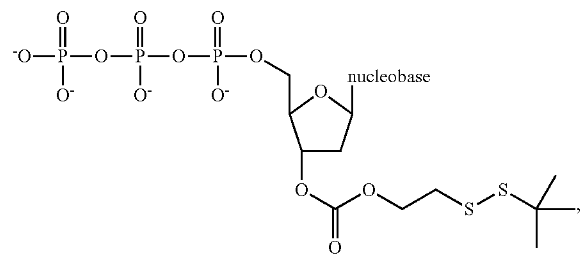

-continued (4B)

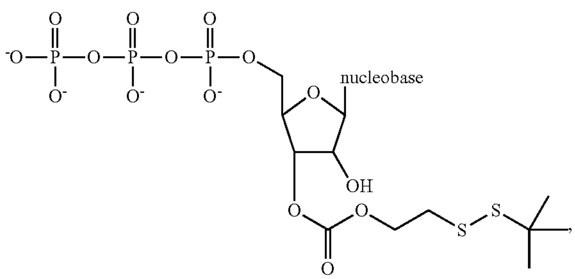

(5A)

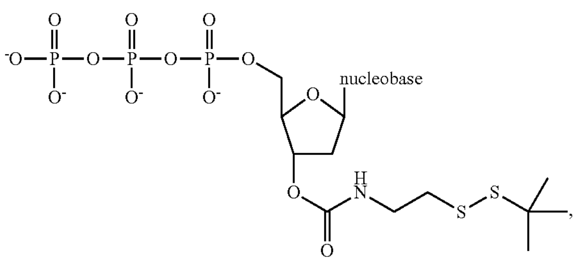

(5B)

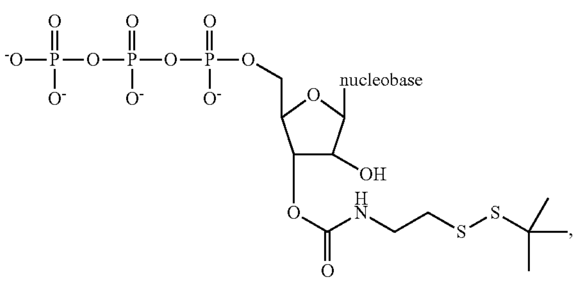

-continued (8A)

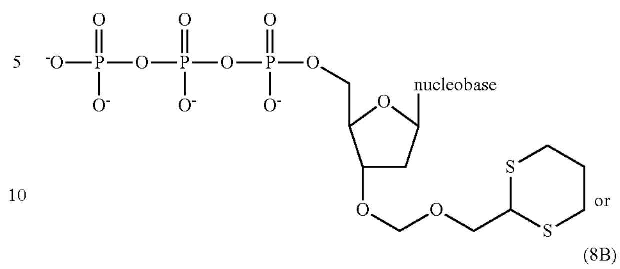

or (8B)

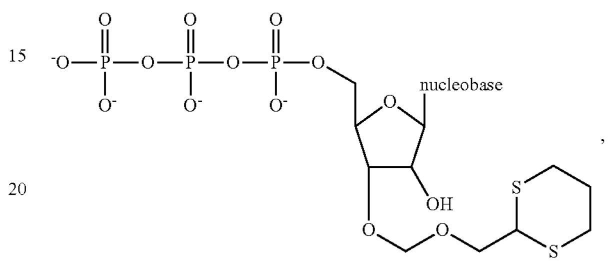

, wherein nucleobase is selected from the group consisting of adenine (A), cytosine (C), guanine (G), uracil (U) and thymine (T).

17. The method of claim 1, wherein the polymerase comprises terminal deoxynucleotidyl transferase (TdT) and/or polymerase theta (POLQ).

18. The method of claim 11, wherein the deoxyribonucleoside triphosphate is selected from the group consisting of deoxyadenosine triphosphate, deoxycytidine triphosphate, deoxyguanosine triphosphate and deoxythymidine triphosphate.

* * * * *

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
```

-continued

<222> LOCATION: (1)..(1)
<223> OTHER INFORMATION: fluorescein tag (FAM)

<400> SEQUENCE: 1
tgtagtgtct tgttctgtga 20